(12) United States Patent
Fukase et al.

(10) Patent No.: US 8,298,513 B2
(45) Date of Patent: Oct. 30, 2012

(54) HEXATRIENE-β-CARBONYL COMPOUND

(75) Inventors: Koichi Fukase, Osaka (JP); Katsunori Tanaka, Osaka (JP); Yasuyoshi Watanabe, Hyogo (JP); Tsuyoshi Tahara, Hyogo (JP); Koki Hasegawa, Hyogo (JP)

(73) Assignees: Osaka University, Osaka (JP); Riken, Saitama (JP)

( * ) Notice: Subject to any disclaimer, the term of this patent is extended or adjusted under 35 U.S.C. 154(b) by 318 days.

(21) Appl. No.: 12/525,599

(22) PCT Filed: Feb. 5, 2008

(86) PCT No.: PCT/JP2008/051871
§ 371 (c)(1),
(2), (4) Date: Aug. 3, 2009

(87) PCT Pub. No.: WO2008/096760
PCT Pub. Date: Aug. 14, 2008

(65) Prior Publication Data
US 2010/0008857 A1    Jan. 14, 2010

(30) Foreign Application Priority Data

Feb. 5, 2007  (JP) ................................. 2007-025489

(51) Int. Cl.
*A61K 49/00*  (2006.01)
(52) U.S. Cl. ........................................ 424/9.1
(58) Field of Classification Search ............ 424/9.1
See application file for complete search history.

(56) References Cited

FOREIGN PATENT DOCUMENTS

| JP | 2003-160547 | 6/2003 |
| JP | 2004-528275 | 9/2004 |
| JP | 2006-510577 | 3/2006 |
| WO | 02/46147 | 6/2002 |

OTHER PUBLICATIONS

Tanaka et al. Journal of Organic Chemistry, moiety66, 3099-3110, p. 3099, col. B, Scheme 1.*
Tanaka et al. Journal of Organic Chemistry (2001), 66(9), 3099-3110.*
Tanaka, et al., "Synthesis of a New Phospholipase $A_2$ Inhibitor of an Aldehyde Terpenoid and its Possible Inhibitory Mechanism", Tetrahedron Letters 39, 1998, p. 1185-1188.
Tanaka, et al., "The Inhibitory Mechanism of Bovine Pancreatic Phospholipase $A_2$ by Aldehyde Terpenoids", Tetrahedron 55, 1999, p. 1657-1686.
Tanaka, et al., "The Inhibitory Mechanism of Phospholipase $A_2$ by Aldehyde Terpenoids", J. of Synth. Org. Chem. Japan, vol. 57, 1999, p. 876-887.
Tanaka, et al., "Significant Acceleration of 6π-Azaelectrocyclization Resulting from a Remarkable Substituent Effect and Formal Synthesis of the Ocular Age Pigment A2-E by a New Method for Substituted Pyridine Synthesis", J. Org. Chem., vol. 66, No. 9, 2001, p. 3099-3110.
Tanaka, et al., A Submicrogram-Scale Protocol for Biomolecule-Based PET Imaging by Rapid 6π7π-Azaelectrocyclization: Visualization of Sialic Acid Dependent Circulatory Residence of Glycoproteins, Angew. Chem. Int. Ed., vol. 47, pp. 102-105, 2008.
Tanaka, et al., "Noninvasive Imaging of Dendrimer-Type N-Glycan Clusters: In Vivo Dynamics Dependence on Oligosaccharide Structure", Angew. Chem. Int. Ed., vol. 49, pp. 8195-8200, 2010. Tanaka, et al., "A Combined 6π-Azaelectrocyclization/Staudinger Approach to Protein and Cell Engineering: noninvasive Tumor Targeting by N-Glycan-Engineered Lymphocytes", Journal of Carbohydrate Chemistry, vol. 29, pp. 118-132, 2010.
Tanaka, et al., "Electrocycliaztion-Based Labeling Allows Efficient in Vivo Imaging of Cellular Trafficking", Chem. Med. Chem., vol. 5, pp. 841-845, 2010.
Tanaka, et al., "Exploring a Unique Reactivity of 6π-Azaelectrocyclization to Enzyme Inhibition, Natural Products Synthesis, and Molecular Imaging: An approach to Chemical Biology by Synthetic Chemists", SYNLETT, No. 15, pp. 2115-2139, 2011.

* cited by examiner

Primary Examiner — Nizal Chandrakumar
(74) Attorney, Agent, or Firm — Hamre, Schumann, Mueller & Larson, P.C.

(57) ABSTRACT

A label with which labeling is easy when labeling a molecule, i.e., a label that has a high reaction rate upon labeling and that produces a high reaction yield, as well as a precursor for the production of the label are provided. This is achieved by a hexatriene-β-carbonyl compound represented by Formula (I), a hexatriene-β-carbonyl compound represented by Formula (II), a hexatriene-β-carbonyl compound represented by Formula (III) and a hexatriene-β-carbonyl compound represented by Formula (IV).

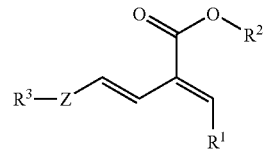

(I)

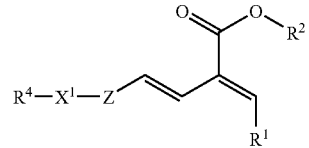

(II)

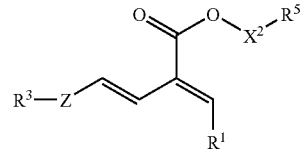

(III)

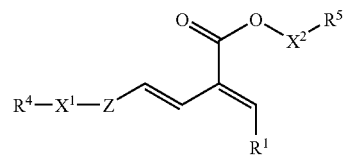

(IV)

(wherein $R^1$, $R^2$, $R^3$, $R^4$, $R^5$, $X^1$, $X^2$ and Z are as defined in the specification)

2 Claims, 5 Drawing Sheets

HEXATRIENE-β-CARBONYL COMPOUND

TECHNICAL FIELD

The present invention relates to a novel hexatriene-β-carbonyl compound.

BACKGROUND ART

Conventionally, PET (positron emission tomography) measurement, fluorescent imaging, MRI (magnetic resonance imaging), etc., have been used as methods to make a non-invasive diagnosis for a living body. In such methods, molecules that are present in a living body, such as those of proteins, antibodies, peptides and sugar chains, are labeled using, for example, radioactive labels, and such labels are detected to form an image of the distribution or the like of such molecules in a living body. Using the image thus formed, it is possible to diagnose a disease in the living body.

However, it is not easy with many of these methods to perform such a labeling procedure. In the case of, for example, PET measurement that uses a labeled compound that is labeled with $^{11}C$, which has a short half-life, it is necessary to perform the process from label production to PET measurement in a short period of time. Accordingly, it is necessary to install a cyclotron, an automated synthesizer and like devices in medical facilities where PET measurement is performed and to produce such a label for every PET measurement (see, for example, Patent Document 1). In addition, such methods are also problematic in that, e.g., the rate of reaction for labeling a biopolymer using a label is low and the reaction yield is low, thereby making it difficult to label unstable biomolecules.

It is known that a compound that has a hexatriene-β-keto structure undergoes cyclization due to an azaelectrocylic reaction with, for example, an amino group of a lysine residue (see, for example, Non-Patent Documents 1, 2 and 3). For example, a compound having a hexatriene-β-keto structure as represented by the formula below promptly reacts with the lysine residue of phospholipase $A_2$ ($PLA_2$), forms a Schiff base and then undergoes cyclization.

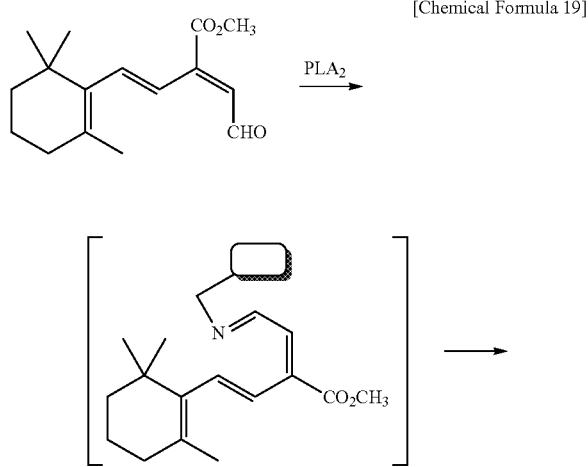

[Chemical Formula 19]

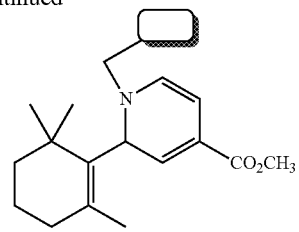

-continued

However, no compound that has the aforementioned hexatriene-β-keto structure and that is advantageous for use in the aforementioned labeling procedure is known.

Patent Document 1: JP 2005-154374A
Non-Patent Document 1: Tanaka et al., *Tetrahedron Lett.*, 1998, Vol. 39, pp. 1185-1188.
Non-Patent document 2: Tanaka et al., *Tetrahedron*, 1999, Vol. 55, pp. 1657-1686
Non-Patent document 3: Tanaka et al., *J. of Synth. Org. Chem. Japan*, 1999, Vol. 57, pp. 876-887

DISCLOSURE OF THE INVENTION

Problem to Be Solved by the Invention

Accordingly, an object of the present invention is to provide a label with which labeling is easy at the time of labeling a molecule, i.e., a label that has a high reaction rate upon labeling and that produces a high reaction yield, as well as a precursor for the production of the label.

Means for Solving Problem

The present invention provides a hexatriene-β-carbonyl compound represented by General Formula (I).

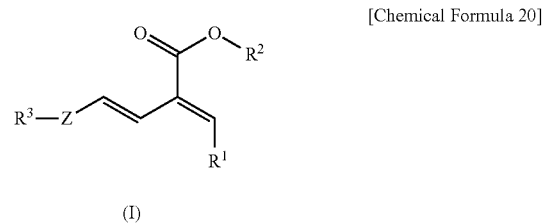

[Chemical Formula 20]

(I)

In the formula above, $R^1$ is a group represented by —$CH_2OH$, —$CH_2$—$OR^{11}$ or —CHO, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH, and [Chemical Formula 21]

Z is a group represented by the formula below:

[Chemical Formula 22]

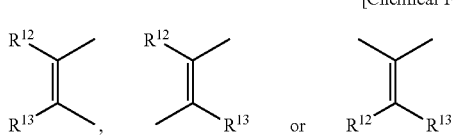

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^1$ is a hydrogen atom, a group represented by —OH, —$CO_2H$, —SH or —$NH_2$, or a protecting group for a group represented by —OH, —$CO_2H$, —SH or —$NH_2$, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, the present invention provides a hexatriene-β-carbonyl compound represented by General Formula (II).

[Chemical Formula 23]

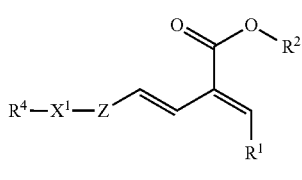

(II)

In the formula above, $R^1$ is a group represented by —$CH_2OH$, —$CH_2$—$OR^{11}$ or —CHO, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label, $X^1$ is a group represented by the formula -$L^1$-$A^1$-, the formula -$A^1$-$L^1$- or the formula below:

[Chemical Formula 24]

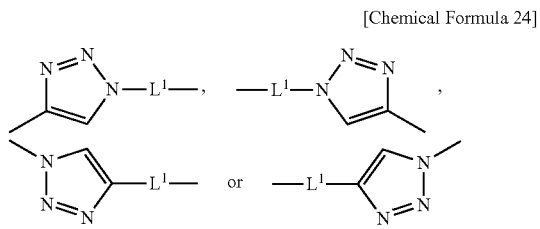

and Z is a group represented by the formula below:

[Chemical Formula 25]

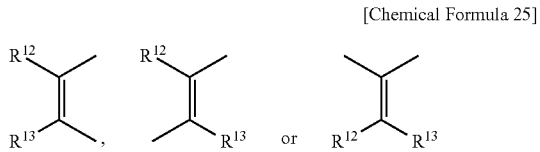

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

Moreover, the present invention provides a hexatriene-β-carbonyl compound represented by General Formula (III).

[Chemical Formula 26]

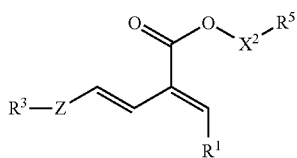

In the formula above, $R^1$ is a group represented by —$CH_2OH$, —$CH_2$—$OR^{11}$ or —CHO, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH, [Chemical Formula 27]

$R^5$ is a carbonyl group substituted with a substituent that functions as a label, $X^2$ is a group represented by the formula -$L^2$-$A^2$-$L^3$-, and Z is a group represented by:

[Chemical Formula 28]

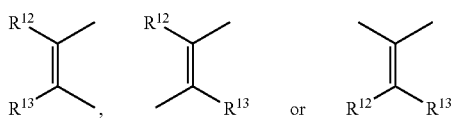

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_n$— (wherein n and m each independently represent an integer of 1 to 20), $A^2$ is a group represented by —O—, —$CO_2$—, —S— or —NH—, $L^3$ is a bond or a group represented by the formula $(CH_2)_n$— or —$(CH_2)_n$—O—$(CH_2)_m$— (wherein n and m each independently represent an integer of 1 to 20), $M^1$ is a hydrogen atom, a group represented by —OH, —$CO_2H$, —SH or —$NH_2$, or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, the present invention provides a hexatriene-β-carbonyl compound represented by General Formula (IV).

[Chemical Formula 29]

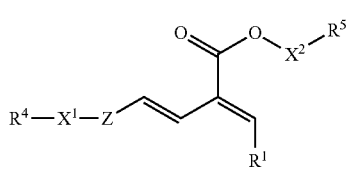

(IV)

In the formula above, $R^1$ is a group represented by —$CH_2OH$, —$CH_2$—$OR^{11}$ or —CHO, $R^4$ is a carbonyl group substituted with a substituent that functions as a label, $R^5$ is a carbonyl group substituted with a substituent that functions as a label, $X^1$ is a group represented by the formula -$L^1$-$A^1$-, the formula -$A^1$-$L^1$- or the formula below:

[Chemical Formula 30]

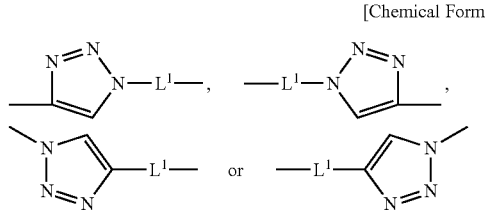

$X^2$ is a group represented by the formula -$L^2$-$A^2$-$L^3$-, and

Z is a group represented by the formula below:

[Chemical Formula 31]

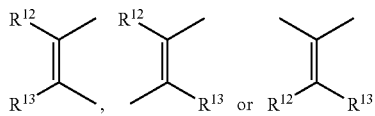

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$, the formula —($CH_2$)$_n$—CONH— or the formula —CONH—($CH_2$)$_n$— (wherein n and m each independently represent an integer of 1 to 20), $A^1$ is a group represented by —O—, —$CO_2$—, —S— or —NH—, $L^2$ is a bond or a group represented by —($CH_2$)$_n$—O—($CH_2$)$_m$— (wherein n and m each independently represent an integer of 1 to 20), $A^2$ is a group represented by —O—, —$CO_2$—, —S— or —NH—, $L^3$ is a bond or a group represented by the formula —($CH_2$)$_n$— or —($CH_2$)$_n$—O—($CH_2$)$_m$— (wherein n and m each independently represent an integer of 1 to 20), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Effects of the Invention

Use of the compound represented by Formula (II), the compound represented by Formula (III) and the compound represented by Formula (IV) of the present invention is advantageous in that molecules that are unstable and that it has been difficult to label can be labeled readily and promptly. In addition, the compound represented by Formula (III), the compound represented by Formula (IV) and the compound represented by Formula (IV) of the present invention are readily obtainable from the compound represented by Formula (I) of the present invention.

BEST MODE OF CARRYING OUT THE INVENTION

The present invention is directed to, as described above, a hexatriene-β-carbonyl compound represented by General Formula (I).

[Chemical Formula 32]

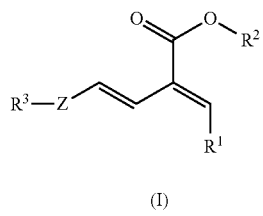

(I)

In the formula above, $R^1$ is a group represented by —$CH_2OH$, —$CH_2$—$OR^{11}$ or —CHO, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH, and [Chemical Formula 33]

Z is a group represented by the formula below:

[Chemical Formula 34]

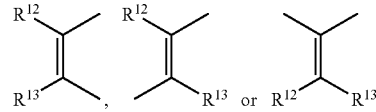

or a divalent group derived from an aromatic hydrocarbon or a divalent group derived from an aromatic hydrocarbon substituted with one or more substituents.

In the formulae above, $L^1$ is a bond or a group represented by the formula —($CH_2$)$_n$—, the formula —($CH_2$)$_n$—O—($CH_2$)$_m$—, the formula —($CH_2$)$_n$—CONH— or the formula —CONH—($CH_2$)$_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $L^2$ is a bond or a group represented by —($CH_2$)$_n$—O—($CH_2$)$_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^1$ is a hydrogen atom, a group represented by —OH, —$CO_2H$, —SH or —$NH_2$, or a protecting group for a group represented by —OH, —$CO_2H$, —SH or —$NH_2$, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

The present invention is directed to a hexatriene-β-carbonyl compound represented by General Formula (II).

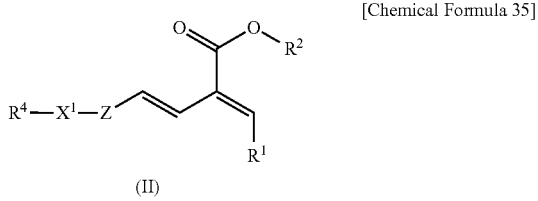

(II)

In the formula above, $R^1$ is a group represented by —$CH_2OH$, —$CH_2$—$OR^{11}$ or —CHO, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label, $X^1$ is a group represented by the formula -$L^1$-$A^1$-, the formula -$A^1$-$L^1$- or the formula below:

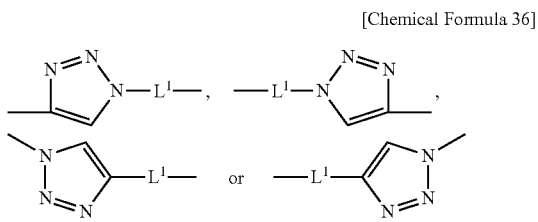

and Z is a group represented by the formula below:

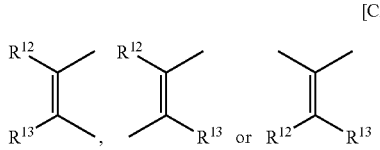

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The present invention is directed to a hexatriene-β-carbonyl compound represented by General Formula (III).

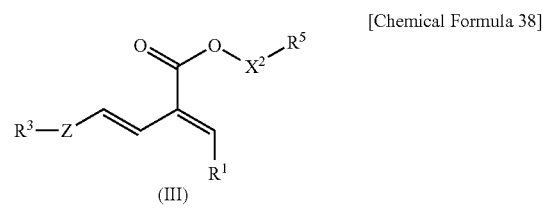

(III)

In the formula above, $R^1$ is a group represented by —$CH_2OH$, —$CH_2$—$OR^{11}$ or —CHO, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH,  [Chemical Formula 39]

$R^5$ is a carbonyl group substituted with a substituent that functions as a label, $X^2$ is a group represented by the formula -$L^2$-$A^2$-$L^3$-, and Z is a group represented by:

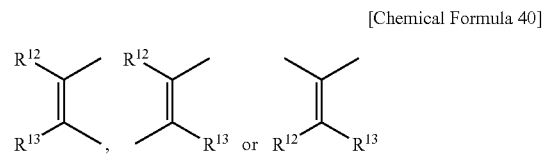

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —(CH$_2$)$_n$—CONH— or the formula —CONH—(CH$_2$)$_m$— (wherein n and m each independently represent an integer of 1 to 20, preferably an integer of 1 to 12 and more preferably an integer of 1 to 7), A$^1$ is a group represented by —O—, —CO$_2$—, —S— or —NH—, L$^2$ is a bond or a group represented by —(CH$_2$)$_n$—O—(CH$_2$)$_m$— (wherein n and m each independently represent an integer of 1 to 20, preferably an integer of 1 to 12 and more preferably an integer of 1 to 7), A$^2$ is a group represented by —O—, —CO$_2$—, —S— or —NH—, L$^3$ is a bond or a group represented by the formula —(CH$_2$)$_n$— or —(CH$_2$)$_n$—O—(CH$_2$)$_m$— (wherein n and m each independently represent an integer of 1 to 20, preferably an integer of 1 to 12 and more preferably an integer of 1 to 7), M$^1$ is a hydrogen atom, a group represented by —OH, —CO$_2$H, —SH or —NH$_2$, or a protecting group for a group represented by —OH, —CO$_2$H, —SH or —NH$_2$, R$^{11}$ is a protecting group for a hydroxyl group, R$^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and R$^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The present invention is directed to a hexatriene-β-carbonyl compound represented by General Formula (IV)

[Chemical Formula 41]

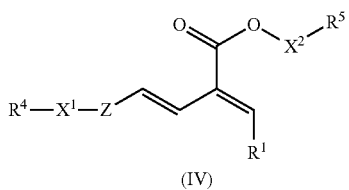

(IV)

In the formula above,

R$^1$ is a group represented by —CH$_2$OH, —CH$_2$—OR$^{11}$ or —CHO,

R$^4$ is a carbonyl group substituted with a substituent that functions as a label, R$^5$ is a carbonyl group substituted with a substituent that functions as a label, X$^1$ is a group represented by the formula -L$^1$-A$^1$-, the formula -A$^1$-L$^1$- or the formula below:

[Chemical Formula 42]

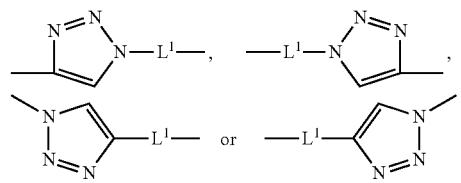

X$^2$ is a group represented by the formula -L$^2$-A$^2$-L$^3$-, and Z is a group represented by the formula below:

[Chemical Formula 43]

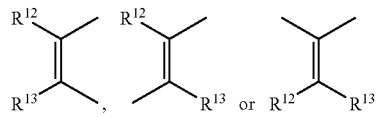

or a divalent group derived from an aromatic hydrocarbon or a divalent group derived from an aromatic hydrocarbon substituted with one or more substituents.

In the formulae above,

L$^1$ is a bond or a group represented by the formula —(CH$_2$)$_n$—, the formula —(CH$_2$)$_n$—O—(CH$_2$)$_m$—, the formula —(CH$_2$)$_n$—CONH— or the formula —CONH—(CH$_2$)$_n$— (wherein n and m each independently represent an integer of 1 to 20, preferably an integer of 1 to 12 and more preferably an integer of 1 to 7), A$^1$ is a group represented by —O—, —CO$_2$—, —S— or —NH—, L$^2$ is a bond or a group represented by —(CH$_2$)$_n$—O—(CH$_2$)$_m$— (wherein n and m each independently represent an integer of 1 to 20, preferably an integer of 1 to 12 and more preferably an integer of 1 to 7), A$^2$ is a group represented by —O—, —CO$_2$—, —S— or —NH—, L$^3$ is a bond or a group represented by the formula —(CH$_2$)$_n$— or —(CH$_2$)$_n$—O—(CH$_2$)$_m$— (wherein n and m each independently represent an integer of 1 to 20, preferably an integer of 1 to 12 and more preferably an integer of 1 to 7), R$^{11}$ is a protecting group for a hydroxyl group, R$^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and R$^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, it is preferable for the present invention that in Formula (I),

R$^1$ refers to a group represented by —CH$_2$OH, —CH$_2$—OSi(t-Bu)Ph$_2$ or —CHO, $R^2$ refers to a lower alkyl group or a group represented by the formula -$L^2$-$A^2$-M, $R^3$ refers to a hydrogen atom or a group represented by the formula -$L^1$-$A^1$-M, a group represented by the formula -$L^1$-$N_3$ or a group represented by the formula -$L^1$-C≡CH, and Z refers to a divalent group derived from an aromatic hydrocarbon; and, in the formulae above; and in the formulae above, $L^1$ is a bond or a group represented by —$(CH_2)_n$—CONH— or —CONH—$(CH_2)_n$— (wherein n represents an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20);

$A^2$ is a group represented by —O—, —$CO_2$—, —S— or —NH—, and

M refers to a hydrogen atom or an acyl group.

Moreover, it is preferable for the present invention that in Formula (II), $R^1$ refers to a group represented by —$CH_2OH$ or —CHO, $R^2$ refers to a lower alkyl group, $R^4$ refers to a group represented by the formula below:

[Chemical Formula 44]

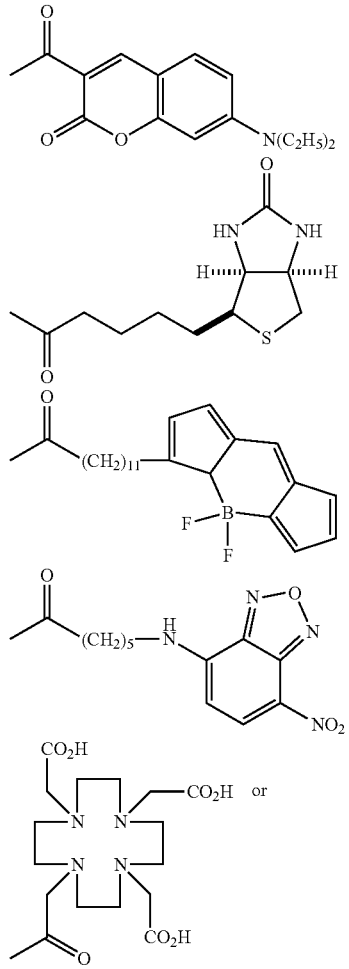

$X^1$ refers to a group represented by the formula -$L^1$-$A^1$-, a group represented by the formula -$A^1$-$L^1$- or a group represented by the formula below:

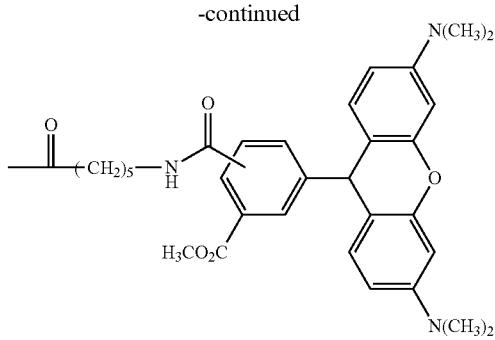

[Chemical Formula 45]

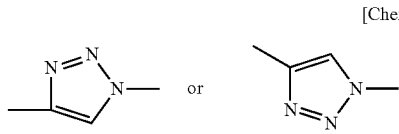

and Z refers to a divalent group derived from an aromatic hydrocarbon; and, in the formulae above, $L^1$ is a bond or a group represented by —$(CH_2)_n$—CONH— or —CONH—$(CH_2)_n$— (wherein n represents an integer of 1 to 20), and $A^1$ is a group represented by —O—, —$CO_2$—, —S— or —NH—.

Moreover, it is preferable for the present invention that in Formula (III), $R^1$ refers to a group represented by —$CH_2OH$, —$CH_2$—OSi(t-Bu)$Ph_2$ or —CHO, $R^3$ refers to a hydrogen atom or a group represented by the formula -$L^1$-$A^1$-M, a group represented by the formula -$L^1$-$N_3$ or a group represented by the formula -$L^1$-C≡CH, $R^5$ refers to a group represented by the formula below:

[Chemical Formula 46]

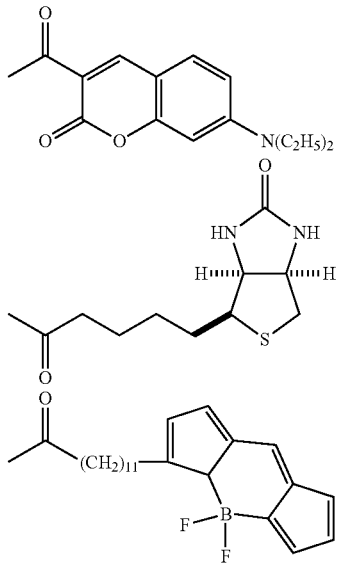

-continued

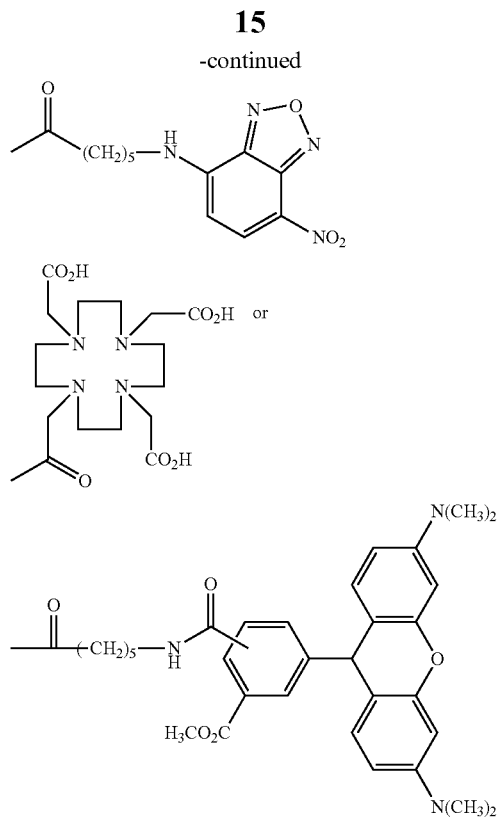

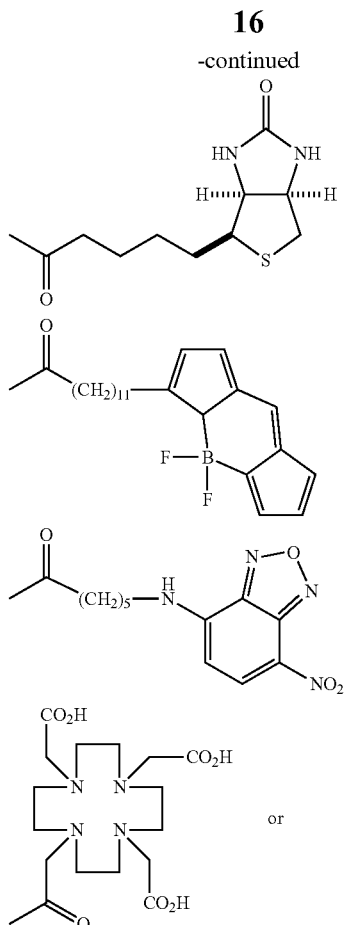

X² refers to a group represented by the formula -L²-A²-L³-, and

Z refers to a divalent group derived from an aromatic hydrocarbon; and, in the formulae above, L¹ is a bond or a group represented by —$(CH_2)_n$—CONH— or —CONH—$(CH_2)_n$— (wherein n represents an integer of 1 to 20), A¹ is a group represented by —O—, —$CO_2$—, —S— or —NH—, L² is a bond or a group represented by —$(CH_2)_n$—O—$(CH_2)_m$— (wherein n and m each independently represent an integer of 1 to 20), A² is a group represented by —O—, —$CO_2$—, —S— or —NH—, L³ is a bond, and M refers to a hydrogen atom or an acyl group.

Moreover, it is preferable for the present invention that in Formula (IV),

R¹ refers to a group represented by —$CH_2OH$, —$CH_2$—OSi(t-Bu)$Ph_2$ or —CHO,

R⁴ refers to a group represented by the formula below:

[Chemical Formula 47]

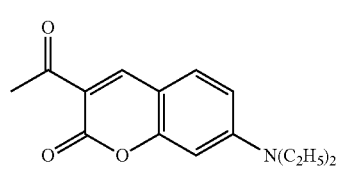

R⁵ refers to a group represented by the formula below:

[Chemical Formula 48]

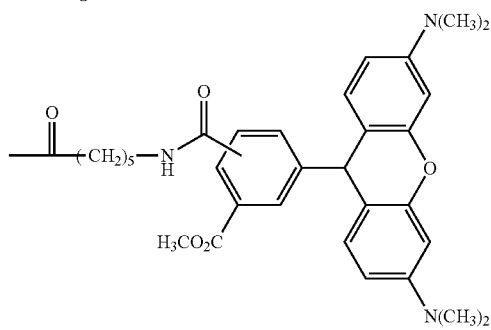

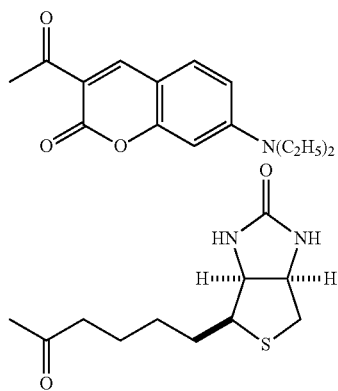

-continued

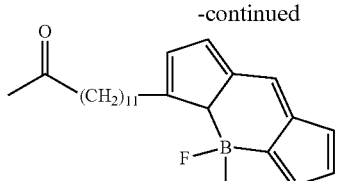

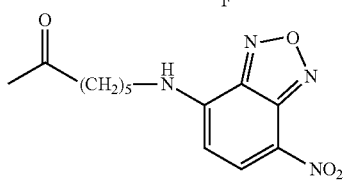

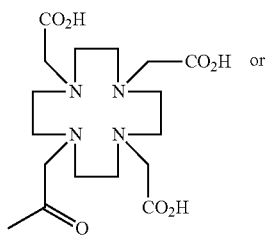

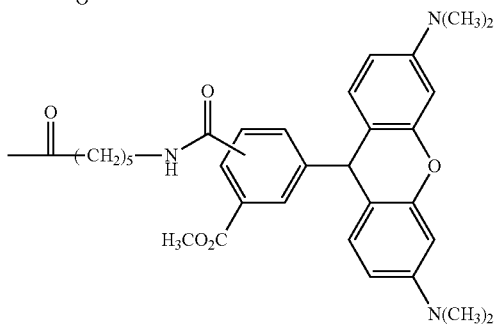

X¹ refers to a group represented by the formula -L¹-A¹-, a group represented by the formula -A¹-L¹- or a group represented by the formula below:

[Chemical Formula 49]

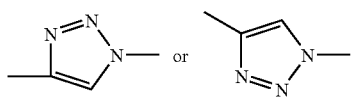

X² refers to a group represented by the formula -L²-A²-L³-, and

Z refers to a divalent group derived from an aromatic hydrocarbon; and, in the formulae above, L¹ is a bond or a group represented by —(CH$_2$)$_n$—CONH— or —CONH—(CH$_2$)$_n$— (wherein n represents an integer of 1 to 20), A¹ is a group represented by —O—, —CO$_2$—, —S— or —NH—, L² is a bond or a group represented by —(CH$_2$)$_n$—O—(CH$_2$)$_m$— (wherein n and m each independently represent an integer of 1 to 20), A² is a group represented by —O—, —CO$_2$—, —S— or —NH—, and L³ is a bond.

Moreover, the compound of the present invention represented by Formula (I) wherein R¹ is —CH$_2$OR¹¹ can be produced according to the following method. Specifically, the compound represented by Formula (I) wherein R¹ is —CH$_2$OR¹¹ can be obtained by treating a compound represented by General Formula (X):

[Chemical Formula 50]

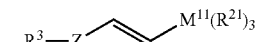
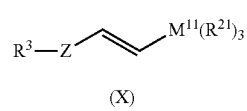

(X)

wherein,

R³ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -L¹-A¹-M¹, the formula -L¹-N$_3$ or the formula:

-L¹-C≡CH, [Chemical Formula 51]

Z is a group represented by the formula below:

[Chemical Formula 52]

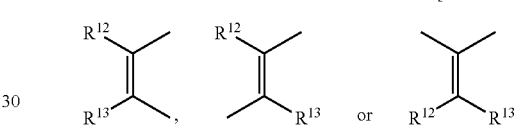

or a divalent group derived from an aromatic hydrocarbon or a divalent group derived from an aromatic hydrocarbon substituted with one or more substituents, M¹¹ is Zn, Sn, B, Al, Mg, Si, As, Cu or Zr, and R²¹ is a lower alkyl group, an aryl group, a heteroaryl group, a hydroxyl group, an alkoxy group or a halogen atom; and in the formulae above, L¹ is a bond or a group represented by the formula —(CH$_2$)$_n$—, the formula —(CH$_2$)$_n$—O—(CH$_2$)$_m$—, the formula —(CH$_2$)$_n$—CONH— or the formula —CONH—(CH$_2$)$_n$— (wherein n and m each independently represent an integer of 1 to 20, preferably an integer of 1 to 12 and more preferably an integer of 1 to 7), A¹ is a group represented by —O—, —CO$_2$—, —S— or —NH—, M¹ is a hydrogen atom, a group represented by —OH, —CO$_2$H, —SH or —NH$_2$, or a protecting group for a group represented by —OH, —CO$_2$H, —SH or —NH$_2$, R¹² is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and R¹³ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, with a compound represented by General Formula (XI):

[Chemical Formula 53]

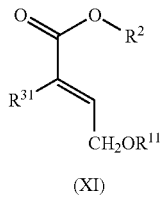

(XI)

wherein, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^{11}$ is a protecting group for a hydroxyl group, and $R^{31}$ is a halogen atom; and $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, and $M^2$ is a hydrogen atom or a protecting group for a group represented by —OH, —$CO_2H$, —SH or —$NH_2$.

Moreover, the compound of the present invention represented by Formula (I) wherein $R^1$ is a group represented by —$CH_2OH$ can be produced according to the following method. Specifically, the compound represented by Formula (I) wherein $R^1$ is —$CH_2OR^{11}$ can be obtained by eliminating $R^{11}$ of a compound represented by General Formula (I-1):

[Chemical Formula 54]

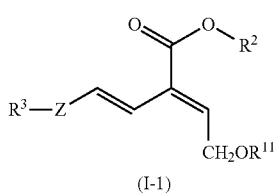

(I-1)

wherein, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH, and                    [Chemical Formula 55]

Z is a group represented by the formula below:

[Chemical Formula 56]

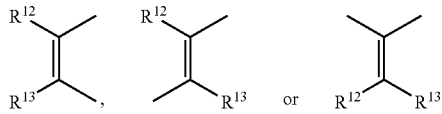

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^1$ is a hydrogen atom, a group represented by —OH, —$CO_2H$, —SH or —$NH_2$, or a protecting group for a group represented by —OH, —$CO_2H$, —SH or —$NH_2$, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(Lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, the compound of the present invention represented by Formula (I) wherein $R^1$ is a group represented by —CHO can be produced according to the following method. Specifically, the compound represented by Formula (I) wherein $R^1$ is a group represented by —$CH_2OH$ can be obtained by oxidizing a compound represented General Formula (I-2):

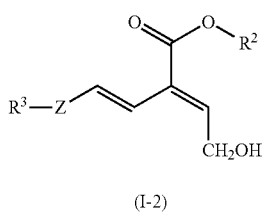

(I-2)

wherein, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula $-L^2-A^2-M^2$, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula $-L^1-A^1-M^1$, the formula $-L^1-N_3$ or the formula:

$-L^1-C\equiv CH$, and

Z is a group represented by the formula below:

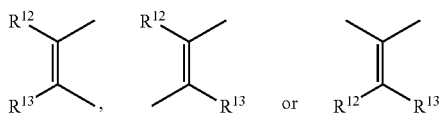

or a divalent group derived from an aromatic hydrocarbon or a divalent group derived from an aromatic hydrocarbon substituted with one or more substituents; and in the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-(CH_2)_n-$ (wherein n and m each independently represent an integer of 1 to 20, preferably an integer of 1 to 12 and more preferably an integer of 1 to 7), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20, preferably an integer of 1 to 12 and more preferably an integer of 1 to 7), $A^2$ is a group represented by $-O-$, $-CO_2-$, $-S-$ or $-NH-$, $M^1$ is a hydrogen atom, a group represented by $-OH$, $-CO_2H$, $-SH$ or $-NH_2$, or a protecting group for a group represented by $-OH$, $-CO_2H$, $-SH$ or $-NH_2$, $M^2$ is a hydrogen atom or a protecting group for a group represented by $-OH$, $-CO_2H$, $-SH$ or $-NH_2$, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, the compound of the present invention represented by Formula (II) wherein $R^1$ is a group represented by $-CH_2-OR^{11}$ and $X^1$ is a group represented by the formula $-A^1-L^1-$ or $-L^1-A^1-$ can be produced according to the following method. Specifically, a compound represented by General Formula (I-11):

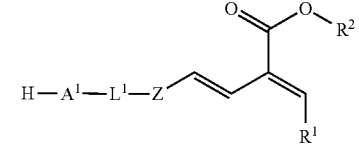

(I-11)

wherein, $R^1$ is a group represented by $-CH_2-OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula $-L^2-A^2-M^2$, and Z is a group represented by the formula below:

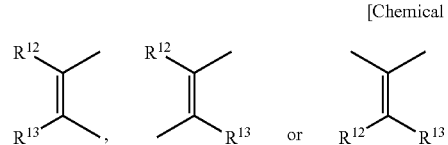

or a divalent group derived from an aromatic hydrocarbon or a divalent group derived from an aromatic hydrocarbon substituted with one or more substituents; and in the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-(CH_2)_n-$ (wherein n and m each independently represent an integer of 1 to 20, preferably an integer of 1 to 12 and more preferably an integer of 1 to 7), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, is coupled with a compound represented by the formula $R^4$—$Y^1$ (XIV) wherein, $R^4$ is a carbonyl group substituted with a substituent that functions as a label and $Y^1$ is a leaving group, to remove $Y^1$—H, and it is thus possible to obtain a compound represented by General Formula (II-1):

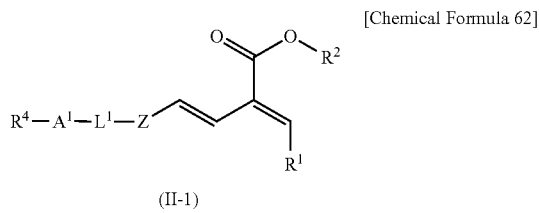

[Chemical Formula 62]

(II-1)

wherein, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label and Z is a group represented by the formula below:

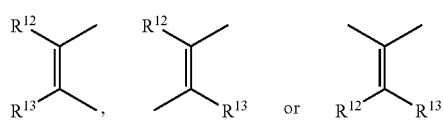

[Chemical Formula 63]

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents; or a compound represented by General Formula (I-12):

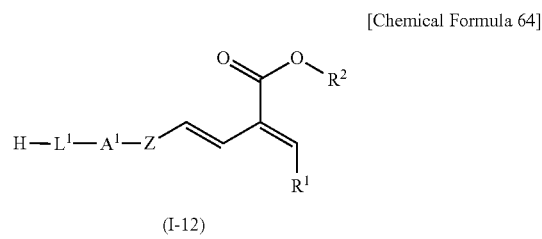

[Chemical Formula 64]

(I-12)

wherein, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, and Z is a group represented by the formula below:

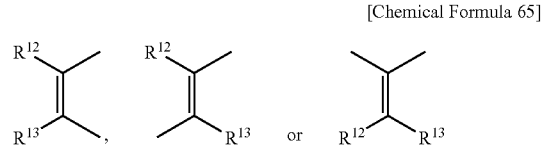

[Chemical Formula 65]

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, is coupled with a compound represented by the formula $R^4$—$Y^1$ (XIV)

wherein, $R^4$ is a carbonyl group substituted with a substituent that functions as a label, and $Y^1$ is a leaving group, to remove $Y^1$—H, and it is thus possible to obtain a compound represented by General Formula (II-2):

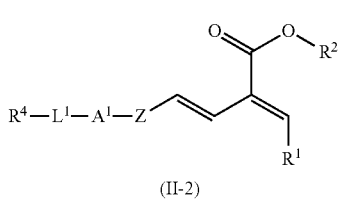

[Chemical Formula 66]

(II-2)

wherein, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label, and Z is a group represented by the formula below:

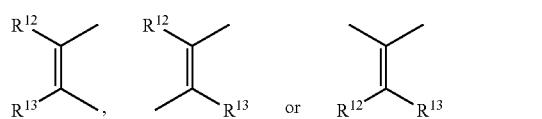

[Chemical Formula 67]

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$)—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

Moreover, the compound of the present invention represented by Formula (II) wherein $R^1$ is a group represented by —$CH_2$—$OR^{11}$ and $X^1$ is:

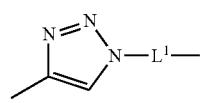

[Chemical Formula 68]

can be produced according to the following method. Specifically, a compound represented by General Formula (I-13):

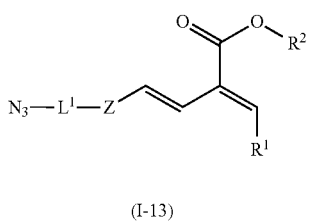

(I-13)

wherein, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, and Z is a group represented by the formula below:

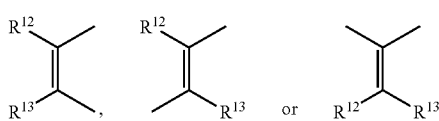

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, is reacted with a compound represented by General Formula (XV):

$$R^4-C\equiv C-H \quad (XV)$$

wherein, $R^4$ is a carbonyl group substituted with a substituent that functions as a label and it is thus possible to obtain a compound represented by General Formula (II-3):

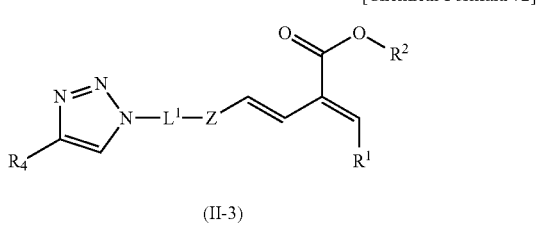

(II-3)

wherein, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label, and Z is a group represented by the formula below:

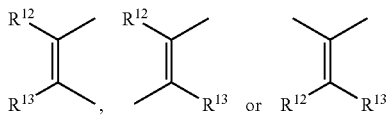

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, the compound of the present invention represented by Formula (II) wherein $R^1$ is a group represented by —$CH_2$—$OR^{11}$ and $X^1$ is:

[Chemical Formula 74]

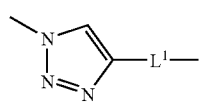

can be produced according to the following method. Specifically, a compound represented by General Formula (I-14):

[Chemical Formula 75]

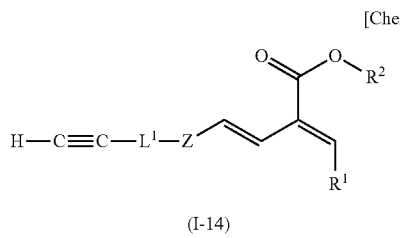

(I-14)

wherein, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, and Z is a group represented by the formula below:

[Chemical Formula 76]

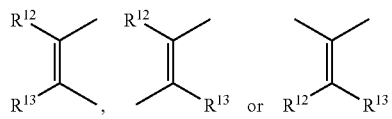

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, is reacted with a compound represented by General Formula (XVI):

$R^4$—$N_3$ (XVI)

wherein, $R^4$ is a carbonyl group substituted with a substituent that functions as a label, and it is thus possible to obtain a compound represented by General Formula (II-4):

[Chemical Formula 77]

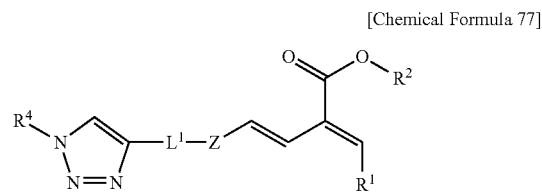

(II-4)

wherein, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label, and Z is a group represented by the formula below:

[Chemical Formula 78]

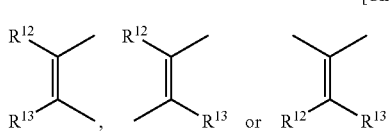

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents).

Moreover, the compound of the present invention represented by Formula (II) wherein $R^1$ is a group represented by —$CH_2OH$ can be produced according to the following method. Specifically, by eliminating $R^{11}$ of the compound represented by Formula (II) wherein $R^1$ is —$CH_2OR^{11}$, the compound represented by Formula (II) wherein $R^1$ is a group represented by —$CH_2OH$ can be obtained.

Moreover, the compound of the present invention represented by Formula (II) wherein $R^1$ is a group represented by —CHO can be produced according to the following method. Specifically, by oxidizing the compound represented by Formula (II) wherein $R^1$ is a group represented by —$CH_2OH$, the compound represented by Formula (II) wherein $R^1$ is a group represented by —CHO can be obtained.

Moreover, the compound of the present invention represented by Formula (III) wherein $R^1$ is a group represented by —$CH_2$—$OR^{11}$ can be produced according to the following method. Specifically, a compound represented by General Formula (I-21):

[Chemical Formula 79]

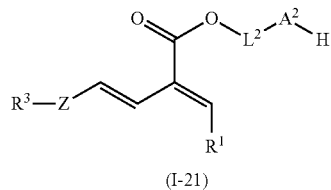

(I-21)

wherein, $R^1$ is a group represented by —$CH_2$—$OR^{11}$, $R^3$ is a hydrogen atom, a lower alkyl group, a lower alkyl group substituted with one or more substituents, an ar(lower) alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH, and      [Chemical Formula 80]

Z is a group represented by:

[Chemical Formula 81]

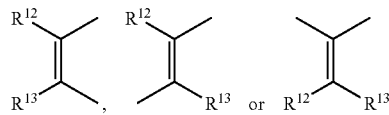

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $M^1$ is a hydrogen atom, a group represented by —OH, —$CO_2H$, —SH or —$NH_2$, or a protecting group for a group represented by —OH, —$CO_2H$, —SH or —$NH_2$, $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $R^{11}$ a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(Lower) alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, is coupled with a compound represented by the formula $R^5$-$L^3$-$Y^2$ (XVII)

wherein, $R^5$ is a carbonyl group substituted with a substituent that functions as a label, $L^3$ is a bond or a group represented by the formula —$(CH_2)_n$— or —$(CH_2)_n$—O—$(CH_2)_m$— (wherein n and m each independently represent an integer of 1 to 20, preferably an integer of 1 to 12 and more preferably an integer of 1 to 7), and $Y^2$ is a leaving group, to remove $Y^2$—H, and it is thus possible to obtain the compound represented by General Formula (III) wherein $R^1$ is a group represented by —$CH_2OR^{11}$.

Moreover, the compound of the present invention represented by Formula (III) wherein $R^1$ is a group represented by —$CH_2OH$ can be produced according to the following method. Specifically, by eliminating $R^{11}$ of the compound represented by Formula (III) wherein $R^1$ is —$CH_2OR^{11}$, the compound represented by formula (III) wherein $R^1$ is a group represented by —$CH_2OH$ can be obtained.

Moreover, the compound of the present invention represented by Formula (III) wherein $R^1$ is a group represented by —CHO can be produced according to the following method. Specifically, by oxidizing the compound represented by Formula (III) wherein $R^1$ is a group represented by —$CH_2OH$, the compound represented by formula (III) wherein $R^1$ is a group represented by —CHO can be obtained.

Moreover, the compound of the present invention represented by Formula (IV) wherein $R^1$ is a group represented by —$CH_2$—$OR^{11}$ can be produced according to the following method. Specifically, a compound represented by General Formula (II-11):

[Chemical Formula 82]

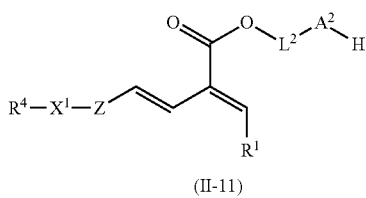

(II-11)

wherein, $R^1$ is a group represented by —$CH_2$—$OR^{11}$, $R^4$ is a carbonyl group substituted with a substituent that functions as a label, $X^1$ is a group represented by the formula -$L^1$-$A^1$-, the formula $A^1$-$L^1$- or the formula below:

[Chemical Formula 83]

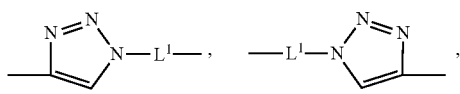

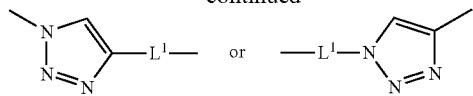 or 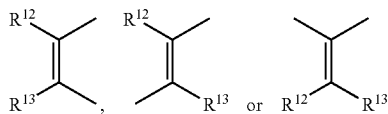

and Z is a group represented by the formula below:

[Chemical Formula 84]

$$R^{12}\diagup\!\!\!\!\diagdown R^{13}, \quad R^{12}\diagup\!\!\!\!\diagdown R^{13} \quad \text{or} \quad R^{12}\diagup\!\!\!\!\diagdown R^{13}$$

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, is coupled with a compound represented by the formula $R^5$-$L^3$-$Y^2$ (XVII)

wherein, $R^5$ is a carbonyl group substituted with a substituent that functions as a label $L^3$ is a bond or a group represented by the formula —$(CH_2)_n$— or —$(CH_2)_n$—O—$(CH_2)_m$— (wherein n and m each independently represent an integer of 1 to 20, preferably an integer of 1 to 12 and more preferably an integer of 1 to 7), and $Y^2$ is a leaving group, to remove $Y^2$—H, and it is thus possible to obtain the compound represented by General Formula (IV) wherein $R^1$ is a group represented by —$CH_2OR^{11}$.

Moreover, the compound of the present invention represented by Formula (IV) wherein $R^1$ is a group represented by —$CH_2$—$OR^{11}$ and $X^1$ is a group represented by the formula -$A^1$-$L^1$- or -$L^1$-$A^1$- can be produced according to the following method. Specifically, a compound represented by General Formula (III-1):

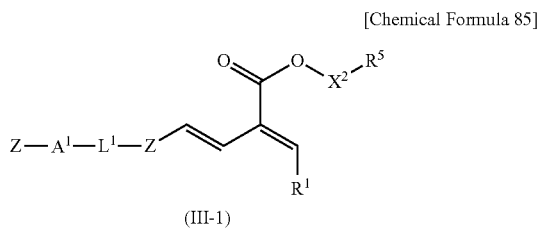

(III-1)

wherein,
$R^1$ is a group represented by —$CH_2$—$OR^{11}$,
$R^5$ is a carbonyl group substituted with a substituent that functions as a label,
$X^2$ is a group represented by the formula -$L^2$-$A^2$-$L^3$-, and
Z is a group represented by:

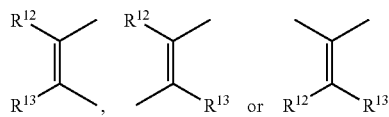

or a divalent group derived from an aromatic hydrocarbon or a divalent group derived from an aromatic hydrocarbon substituted with one or more substituents; and
in the formulae above,
$L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7),
$A^1$ is a group represented by —O—, —$CO_2$—, —S— or —NH—,
$L^2$ is a bond or a group represented by —$(CH_2)_n$—O—$(CH_2)_n$— (wherein n and m each independently represent an integer of 1 to 20, preferably an integer of 1 to 12 and more preferably an integer of 1 to 7),
$A^2$ is a group represented by —O—, —$CO_2$—, —S— or —NH—,
$L^3$ is a bond or a group represented by the formula —$(CH_2)_n$— or —$(CH_2)_n$—O—$(CH_2)_m$— (wherein n and m each independently represent an integer of 1 to 20, preferably an integer of 1 to 12 and more preferably an integer of 1 to 7),
$R^{11}$ is a protecting group for a hydroxyl group,
$R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and
$R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, is coupled with a compound represented by the formula $R^4$—$Y^1$ (XIV)
wherein,
$R^4$ is a carbonyl group substituted with a substituent that functions as a label and
$Y^1$ is a leaving group,
to remove $Y^1$—H, and it is thus possible to obtain a compound represented by General Formula (IV-2):

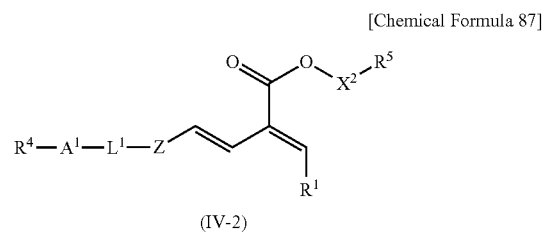

(IV-2)

wherein,
$R^1$ is a group represented by —$CH_2$—$OR^{11}$,
$R^4$ is a carbonyl group substituted with a substituent that functions as a label,
$R^5$ is a carbonyl group substituted with a substituent that functions as a label,
$X^2$ is a group represented by the formula -$L^2$-$A^2$-$L^3$-, and
Z is a group represented by the formula below:

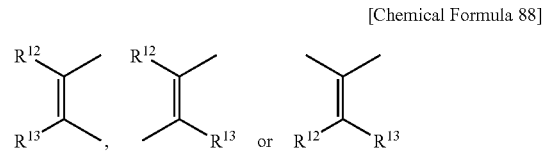

or a divalent group derived from an aromatic hydrocarbon or a divalent group derived from an aromatic hydrocarbon substituted with one or more substituents; and
in the formulae above,
$L^1$ is a bond or a group represented by the formula —$(CH_2)_n$—, the formula —$(CH_2)_n$—O—$(CH_2)_m$—, the formula —$(CH_2)$—CONH— or the formula —CONH—$(CH_2)_n$— (wherein n and m each independently represent an integer of 1 to 20, preferably an integer of 1 to 12 and more preferably an integer of 1 to 7),
$A^1$ is a group represented by —O—, —$CO_2$—, —S— or —NH—,
$L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7),
$A^2$ is a group represented by —O—, —$CO_2$—, —S— or —NH—,
$L^3$ is a bond or a group represented by the formula —$(CH_2)_n$— or —$(CH_2)_n$—O—$(CH_2)_m$— (wherein n and m each independently represent an integer of 1 to 20, preferably an integer of 1 to 12 and more preferably an integer of 1 to 7), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, lower alkyl group, lower alkyl group substituted with one or more substituents, lower alkoxy group, lower alkoxy group substituted with one or more substituents, ar(lower)alkyl group, ar(lower)alkyl group substituted with one or more substituents, ar(lower)alkoxy group, ar(lower)alkoxy group substituted with one or more substituents, aryl group, aryl group substituted with one or more substituents, heteroaryl group or heteroaryl group substituted with one or more substituents; or a compound represented by General Formula (III-2):

[Chemical Formula 89]

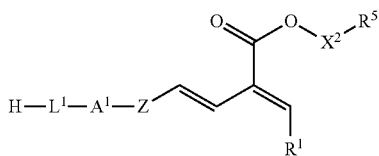

(III-2)

wherein, $R^1$ is a group represented by $-CH_2-OR^{11}$, $R^5$ is a carbonyl group substituted with a substituent that functions as a label, $X^2$ is a group represented by the formula $-L^2-A^2-L^3-$, and Z is a group represented by:

[Chemical Formula 90]

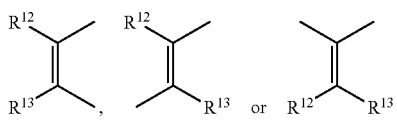

or a divalent group derived from an aromatic hydrocarbon or a divalent group derived from an aromatic hydrocarbon substituted with one or more substituents; and in the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-(CH_2)_n-$ (wherein n and m each independently represent an integer of 1 to 20, preferably an integer of 1 to 12 and more preferably an integer of 1 to 7), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20, preferably an integer of 1 to 12 and more preferably an integer of 1 to 7), $A^2$ is a group represented by $-O-$, $-CO_2-$, $-S-$ or $-NH-$, $L^3$ is a bond or a group represented by the formula $-(CH_2)_n-$ or $-(CH_2)_n-O-(CH_2)_m-$ (wherein n and m each independently represent an integer of 1 to 20, preferably an integer of 1 to 12 and more preferably an integer of 1 to 7), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, is coupled with a compound represented by the formula $R^4-Y^1$ (XIV)

wherein, $R^4$ is a carbonyl group substituted with a substituent that functions as a label and $Y^1$ is a leaving group, to remove $Y^1-H$, and it is thus possible to obtain a compound represented by General Formula (IV-3):

[Chemical Formula 91]

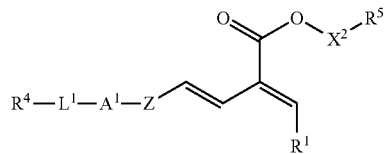

(IV-3)

wherein, $R^1$ is a group represented by $-CH_2-OR^{11}$, $R^4$ is a carbonyl group substituted with a substituent that functions as a label, $R^5$ is a carbonyl group substituted with a substituent that functions as a label, $X^2$ is a group represented by the formula $-L^2-A^2-L^1-$, and Z is a group represented by the formula below:

[Chemical Formula 92]

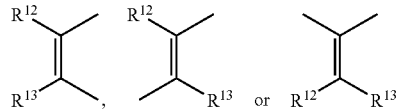

or a divalent group derived from an aromatic hydrocarbon or a divalent group derived from an aromatic hydrocarbon substituted with one or more substituents; and in the formulae above, $L^1$ is a bond or a group represented by the formula $-(CH_2)_n-$, the formula $-(CH_2)_n-O-(CH_2)_m-$, the formula —(CH$_2$)$_n$—CONH— or the formula —CONH—(CH$_2$)$_n$— (wherein n and m each independently represent an integer of 1 to 20, preferably an integer of 1 to 12 and more preferably an integer of 1 to 7), A$^1$ is a group represented by —O—, —CO$_2$—, —S— or —NH—, L$^2$ is a bond or a group represented by —(CH$_2$)$_n$—O—(CH$_2$)$_m$— (wherein n and m each independently represent an integer of 1 to 20, preferably an integer of 1 to 12 and more preferably an integer of 1 to 7), A$^2$ is a group represented by —O—, —CO$_2$—, —S— or —NH—, L$^3$ is a bond or a group represented by the formula —(CH$_2$)$_n$— or —(CH$_2$)$_n$—O—(CH$_2$)$_m$— (wherein n and m each independently represent an integer of 1 to 20, preferably an integer of 1 to 12 and more preferably an integer of 1 to 7), R$^{11}$ is a protecting group for a hydroxyl group, R$^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and R$^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, the compound of the present invention represented by formula (IV) wherein R$^1$ is a group represented by —CH$_2$—OR$^{11}$ and X$^1$ is:

[Chemical Formula 93]

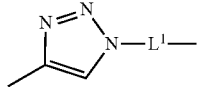

can be produced according to the following method. Specifically, a compound represented by General Formula (III-3):

[Chemical Formula 94]

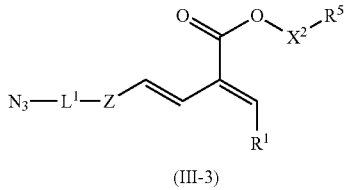

(III-3)

wherein,

R$^1$ is a group represented by —CH$_2$—OR$^{11}$,

R$^5$ is a carbonyl group substituted with a substituent that functions as a label, X$^2$ is a group represented by the formula -L$^2$-A$^2$-L$^3$-, and Z is a group represented by:

[Chemical Formula 95]

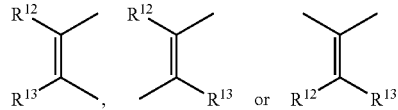

or a divalent group derived from an aromatic hydrocarbon or a divalent group derived from an aromatic hydrocarbon substituted with one or more substituents; and in the formulae above, L$^1$ is a bond or a group represented by the formula —(CH$_2$)$_n$—, the formula —(CH$_2$)$_n$—O—(CH$_2$)$_m$, the formula —(CH$_2$)$_n$—CONH— or the formula —CONH—(CH$_2$)$_n$— (wherein n and m each independently represent an integer of 1 to 20, preferably an integer of 1 to 12 and more preferably an integer of 1 to 7), L$^2$ is a bond or a group represented by —(CH$_2$)$_n$—O—(CH$_2$)$_m$— (wherein n and m each independently represent an integer of 1 to 20, preferably an integer of 1 to 12 and more preferably an integer of 1 to 7), A$^2$ is a group represented by —O—, —CO$_2$—, —S— or —NH—, L$^3$ is a bond or a group represented by the formula —(CH$_2$)$_n$— or —(CH$_2$)$_n$—O—(CH$_2$)$_m$— (wherein n and m each independently represent an integer of 1 to 20, preferably an integer of 1 to 12 and more preferably an integer of 1 to 7), R$^{11}$ is a protecting group for a hydroxyl group, R$^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and R$^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, is reacted with a compound represented by General Formula (XV):

[Chemical Formula 96]

$$R^4\text{—}C\equiv C\text{—}H \qquad (XV)$$

wherein,

R$^4$ is a carbonyl group substituted with a substituent that functions as a label and it is thus possible to obtain a compound represented by General Formula (IV-4):

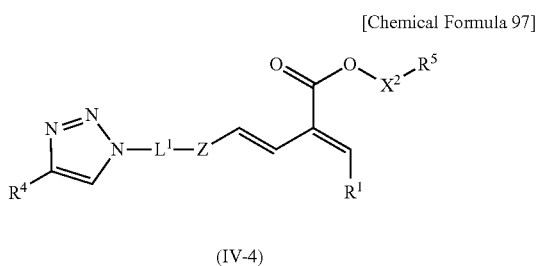

(IV-4)

wherein, $R^1$ is a group represented by —$CH_2$—$OR^{11}$, $R^4$ is a carbonyl group substituted with a substituent that functions as a label, $R^5$ is a carbonyl group substituted with a substituent that functions as a label, $X^2$ is a group represented by the formula -$L^2$-$A^2$-$L^3$-, and Z is a group represented by:

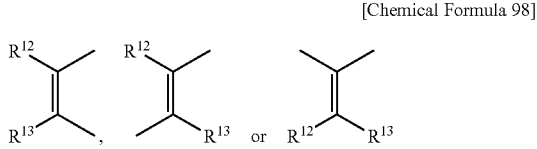

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20, preferably an integer of 1 to 12 and more preferably an integer of 1 to 7), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(Lower)alkyl group, an ar(lower) alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, the compound of the present invention represented by formula (IV) wherein $R^1$ is a group represented by —$CH_2$—$OR^{11}$ and $X^1$ is:

can be produced according to the following method. Specifically, a compound represented by General Formula (III-4):

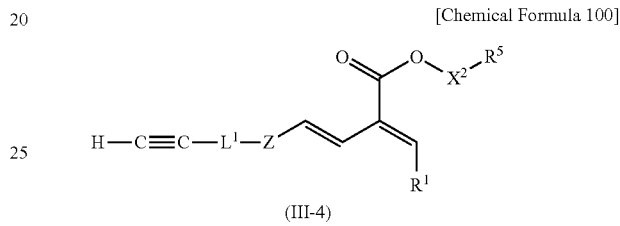

(III-4)

wherein, $R^1$ is a group represented by —$CH_2$—$OR^{11}$, $R^5$ is a carbonyl group substituted with a substituent that functions as a label, $X^2$ is a group represented by the formula -$L^2$-$A^2$-$L^3$-, and Z is a group represented by:

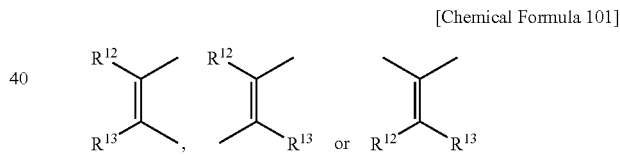

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20, preferably an integer of 1 to 12 and more preferably an integer of 1 to 7), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, is reacted with a compound represented by General Formula (XVI):

wherein, $R^4$ is a carbonyl group substituted with a substituent that functions as a label and it is thus possible to obtain a compound represented by General Formula (IV-5):

[Chemical Formula 102]

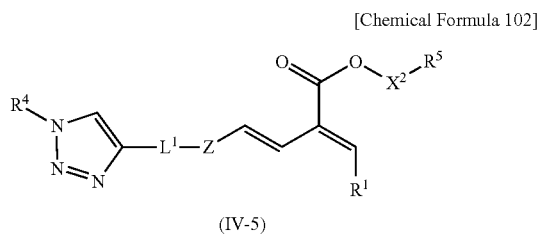

(IV-5)

wherein, $R^1$ is a group represented by —$CH_2$—$OR^{11}$, $R^4$ is a carbonyl group substituted with a substituent that functions as a label, $R^5$ is a carbonyl group substituted with a substituent that functions as a label, $X^2$ is a group represented by the formula -$L^2$-$A^2$-$L^3$-, and Z is a group represented by:

[Chemical Formula 103]

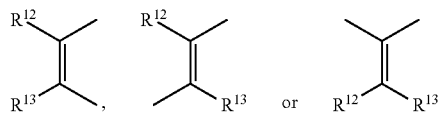

or a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20, preferably an integer of 1 to 12 and more preferably an integer of 1 to 7), $L^2$ is a bond or a group represented by —$(CH_2)_n$—O—$(CH_2)_m$— (wherein n and m each independently represent an integer of 1 to 20, preferably an integer of 1 to 12 and more preferably an integer of 1 to 7), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20, preferably an integer of 1 to 12 and more preferably an integer of 1 to 7), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(Lower) alkoxy group, an ar(lower)alkoxy group substituted with one or more substituents, an aryl group, an aryl group substituted with one or more substituents, a heteroaryl group or a heteroaryl group substituted with one or more substituents.

Moreover, the compound of the present invention represented by Formula (IV) wherein $R^1$ is a group represented by —$CH_2OH$ can be produced according to the following method. Specifically, by eliminating $R^{11}$ of the compound represented by Formula (IV) wherein $R^1$ is —$CH_2OR^{11}$, the compound represented by Formula (VI) wherein $R^1$ is a group represented by —$CH_2OH$ can be obtained.

Moreover, the compound of the present invention represented by Formula (IV) wherein $R^1$ is a group represented by —CHO can be produced according to the following method. Specifically, by oxidizing the compound represented by Formula (IV) wherein $R^1$ is —$CH_2OH$, the compound represented by formula (IV) wherein $R^1$ is a group represented by —CHO can be obtained.

Moreover, the present invention is directed to a test composition that contains one or more members selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO. It is preferable in connection with the composition that the test is carried out via positron emission tomography, fluorescent imaging, nuclear magnetic resonance imaging (MRI), single-photon emission computed tomography (SPECT) or autoradiography.

Moreover, the present invention is directed to a test kit that contains one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO. The test kit is characterized in that the one or more hexatriene-β-carbonyl compounds label an amino group-containing compound that is present in a sample, thereby allowing the amino group-containing compound to be tested.

Moreover, the present invention is directed to an antibody labeled with one or more hexatriene-β-carbonyl compounds into which a positron-emitting metal radionuclide is incorporated. The antibody is characterized in that the one or more hexatriene-β-carbonyl compounds are one or more hexatriene-β-carbonyl compounds selected from the group consisting of a compound represented by Formula (II) wherein $R^1$ is a group represented by —CHO and $R^4$ is a carbonyl group substituted with a substituent that functions as a label the carbonyl group substituted with a substituent that functions as a label being able to coordinate with a radioactive metal; a compound represented by Formula (III) wherein $R^1$ is a group represented by —CHO and $R^5$ is a carbonyl group substituted with a substituent that functions as a label the carbonyl group substituted with a substituent that functions as a label being able to coordinate with a radioactive metal; and a compound represented by Formula (IV) wherein $R^1$ is a group represented by —CHO and at least one of $R^4$ and $R^5$ is a carbonyl group substituted with a substituent that functions as a label the carbonyl group substituted with a substituent that functions as a label being able to coordinate with a radioactive metal Moreover, the present invention is directed to a kit for producing a PET contrast agent that contains an antibody labeled with one or more hexatriene-β-carbonyl compounds into which a positron-emitting metal radionuclide is incorporated. The kit is characterized in that the kit contains one or more hexatriene-β-carbonyl compounds selected from the group consisting of a compound represented by Formula (II) wherein $R^4$ is a carbonyl group substituted with a substituent that functions as a label the carbonyl group substituted with a substituent that functions as a label being able to coordinate with a radioactive metal a compound represented by Formula (III) wherein $R^5$ is a carbonyl group substituted with a substituent that functions as a label, the carbonyl group substituted with a substituent that functions as a label being able to coordinate with a radioactive metal and a compound represented by Formula (IV) wherein at least one of $R^4$ and $R^5$ is a carbonyl group substituted with a substituent that functions as a label the carbonyl group substituted with a substituent that functions as a label being able to coordinate with a radioactive metal;

an antibody to be labeled; and optionally an instruction.

Moreover, the present invention is directed to an antibody labeled with one or more hexatriene-β-carbonyl compounds. The antibody is characterized in that the hexatriene-β-carbonyl compounds are hexatriene-β-carbonyl compounds selected from the group consisting of a compound represented by Formula (II) wherein $R^1$ is a group represented by —CHO, a compound represented by Formula (III) wherein $R^1$ is a group represented by —CHO, and a compound represented by Formula (IV) wherein $R^1$ is a group represented by —CHO.

Moreover, the present invention is directed to a kit for producing an antibody labeled with one or more hexatriene-β-carbonyl compounds. The kit is characterized in that the kit contains:

one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO, and a compound represented by Formula (IV) wherein $R^1$ is a group represented by —CHO, an antibody to be labeled, and optionally an instruction.

Moreover, the present invention is directed to a kit for labeling a protein. The kit for labeling a protein contains:

one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO, a protein to be labeled, and optionally an instruction.

The definitions and examples of various terms used in the present specification are as follows.

The term "lower" refers to 1 to 6 carbon atoms and preferably 1 to 4 carbon atoms unless specified otherwise.

A "lower alkyl group", and the "lower alkyl" moiety in an "ar(lower)alkyl group", a "lower alkoxy group" and an "ar(lower)alkoxy group" refer to linear and branched $C_{1-6}$ alkane residues such as methyl, ethyl, propyl, isopropyl, butyl, isobutyl, t-butyl, pentyl, neopentyl and hexyl. Preferable examples of lower alkyl groups and lower alkyl moieties include $C_{1-5}$ alkyls. Preferable $C_{1-5}$ alkyls include methyl, ethyl, propyl, isopropyl, butyl, isobutyl, t-butyl, pentyl, neopentyl, etc.

An "aryl group" and the "ar" moiety in an "ar(lower)alkyl group" includes phenyl, naphthyl, dihydronaphthyl (such as 1,2-dihydronaphthyl and 1,4-dihydronaphthyl), tetrahydronaphthyl (such as 1,2,3,4-tetrahydronaphthyl), indenyl, anthryl, etc. In particular, preferable as an aryl group and an "ar" moiety are $C_{6-10}$ aryls, with phenyl and naphthyl being particularly preferable.

"Heteroaryl groups" include saturated and unsaturated monocyclic and polycyclic heterocyclic groups having at least one hetero atom such as an oxygen atom, a sulfur atom or a nitrogen atom. Examples of heteroaryl groups include 3 to 8-membered rings that have 1 to 4 nitrogen atoms (preferably 5 or 6-membered unsaturated heteromonocyclic groups) such as pyrrolyl, pyrrolinyl, imidazolyl, pyrazolyl, pyridyl, dihydropyridyl, pyrimidyl, pyranyl, pyridazinyl, triazolyl and tetrazolyl; 3 to 8-membered (preferably 5 or 6-membered) saturated heteromonocyclic groups that have 1 to 4 nitrogen atoms such as pyrrolidinyl, imidazolidinyl, piperidyl and piperazinyl unsaturated fused heteromonocyclic groups that have 1 to 4 nitrogen atoms such as indolyl isoindolyl, indolinyl, indolizinyl, benzimidazolyl, quinolyl, isoquinolyl, indazolyl and benztriazolyl; 3 to 8-membered (preferably 5 or 6-membered) unsaturated heteromonocyclic groups that have 1 or 2 oxygen atoms and 1 to 3 nitrogen atoms such as oxazolyl, isoxazolyl and oxadiazolyl; 3 to 8-membered (preferably 5 or 6-membered) saturated heteromonocyclic groups that have 1 or 2 oxygen atoms and 1 to 3 nitrogen atoms such as morpholinyl and sydnonyl; unsaturated used heterocyclic groups that have 1 or 2 oxygen atoms and 1 to 3 nitrogen atoms such as benzoxazolyl and benzoxadiazolyl; 3 to 8-membered (preferably 5 or 6-membered) unsaturated heteromonocyclic groups that have 1 or 2 sulfur atoms and 1 to 3 nitrogen atoms such thiazolyl, isothiazolyl thiadiazolyl and dihydrothiazinyl; 3 to 8-membered (preferably 5 or 6-membered) saturated heteromonocyclic groups that have 1 or 2 sulfur atoms and 1 to 3 nitrogen atoms such as thiazolidinyl; 3 to 8-membered (preferably 5 or 6-membered) unsaturated heteromonocyclic groups that have 1 or 2 sulfur atoms such as thienyl, dihydrodithionyl and dihydrodithionyl; unsaturated fused heterocyclic groups that have 1 or 2 sulfur atoms and 1 to 3 nitrogen atoms such as benzothiazolyl, benzothiadiazolyl and 4,5,6,7-tetrahydrobenzothiazolyl; 3 to 8-membered (preferably 5 or 6-membered) unsaturated heteromonocyclic groups that have 1 oxygen atom such as furyl; 3 to 8-membered (preferably 5 or 6-membered) unsaturated heteromonocyclic groups that have 1 oxygen atom and 1 or 2 sulfur atoms such as dihydrooxathiinyl; unsaturated fused heterocyclic groups that have 1 or 2 sulfur atoms such as benzothienyl and benzodithiinyl; unsaturated fused heterocyclic groups that have 1 oxygen atom and 1 or 2 sulfur atoms such as benzoxathiinyl; etc.

A "divalent group derived from an aromatic hydrocarbon" refers to a group formed by the removal of two hydrogen atoms from an aromatic hydrocarbon. Examples of such divalent groups derived from aromatic hydrocarbons include 1,2-phenylene, 1,3-phenylene, 1,4-phenylene, etc.

An "ar(lower)alkyl group" refers to a group in which an aforementioned aryl group is attached to a carbon atom of an aforementioned lower alkyl. An example of such an ar(lower) alkyl group is a group in which a $C_{6-10}$ aryl is attached to a $C_{1-6}$ alkyl. Examples of such groups in which a $C_{6-10}$ aryl is attached to a $C_{1-6}$ alkyl, include benzyl, phenethyl, 3-phenylpropyl, benzhydryl, trityl, etc. Preferable examples of such ar(lower)alkyl groups are benzyl, trityl, etc.

Examples of "lower alkoxy groups" include methoxy, ethoxy, propoxy, isopropoxy, butoxy, isobutoxy, t-butoxy, pentyloxy, t-pentyloxy, hexyloxy, etc.

Examples of "ar(lower)alkoxy groups" include benzyloxy, phenethyloxy, 3-phenylpropyloxy, benzhydryloxy, trityloxy, etc.

The substituents in "lower alkyl groups substituted with one or more substituents", "ar(lower)alkyl groups substituted with one or more substituents", "aryl groups substituted with one or more substituents", "heteroaryl groups substituted with one or more substituents", "divalent groups derived from aromatic hydrocarbons substituted with one or more substituents", "lower alkoxy groups substituted with one or more substituents" and "ar(lower)alkoxy groups substituted with one or more substituents" include an imino group, an amino group, a protected amino group, a mono- (or di-) lower alkylamino group, an N-lower alkyl-protected amino group, a lower alkyl group, a hydroxy group, a protected hydroxy group, an acyloxy group, a lower alkoxy group, an acyl group, an amino(lower)alkyl group, a protected amino(lower)alkyl group, a heteroaryl group, a hydroxy-containing aryl group, a carboxy group, a protected carboxy group, a sulfanyl group, a protected sulfanyl group, etc.

Examples of leaving groups include lower alkoxys (such as methoxy and ethoxy), halogens (such as fluorine, chlorine, bromine and iodine), acyloxys, for example, lower alkanoyloxys (such as acetoxy and propionyloxy), p-toluenesulfonyloxy, succinyloxy, etc. Such leaving groups are preferably halogens.

Examples of acyl groups include carbamoyl, aliphatic acyl, and aromatic ring or heterocyclic ring-containing acyl groups. Such aliphatic acyls includes saturated and unsaturated acyclic and cyclic groups, for example, lower alkanoyls (such as formyl, acetyl, propionyl, butyryl isobutyryl, valeryl, isovaleryl, oxalyl, succinyl and pivaloyl); lower alkoxycarbonyls (such as methoxycarbonyl, ethoxycarbonyl, propoxycarbonyl, isopropoxycarbonyl, butoxycarbonyl, t-butoxycarbonyl, pentyloxycarbonyl and hexyloxycarbonyl); lower alkanesulfonyls (such as mesyl ethanesulfonyl, propanesulfonyl, isopropanesulfonyl and butanesulfonyl); etc. Aromatic ring or heterocyclic ring-containing acyl groups include arenesulfonyls (such as benzenesulphonyl and tosyl); aroyls (such as benzoyl, toluoyl, xyloyl, naphthoyl, phthaloyl and indancarbonyl); ar(lower) alkanoyls (such as phenylacetyl and phenylpropionyl); ar(lower)alkoxycarbonyls (such as benzyloxycarbonyl and phenethyloxycarbonyl); etc.

The protecting groups of a "protecting group for a group represented by $—NH_2$" and of a "protected amino group" include acyls (such as acetyl and benzoyl), tri(lower alkyl) silyls (such as trimethylsilyl and t-butyldimethylsilyl), lower alkyldiarylsilyls (such as (t-butyl)diphenylsilyl), ar(lower) alkyls that may have one or more suitable substituents (such as benzyl, trityl, p-nitrobenzyl and p-methoxybenzyl), aryl lower alkoxycarbonyls (such as 9-fluorenylmethylcarbonyl), lower alkoxycarbonyls (such as t-butyloxycarbonyl), etc.

Examples of "protected amino groups" include acyl (such as acetyl and benzoyl)amino, tri(lower alkyl)silyl (such as trimethylsilyl and t-butyldimethylsilyl)amino, lower alkyldiarylsilyl (such as (t-butyl)diphenylsilyl)amino, ar(lower) alkyl that may have one or more suitable substituents (such as benzyl, trityl, p-nitrobenzyl and p-methoxybenzyl)amino, aryl lower alkoxycarbonyl (such as 9-fluorenylmethylcarbonyl)amino, lower alkoxycarbonyl (such as t-butyloxycarbonyl)amino, etc.

The protecting groups of a "protecting group for a hydroxyl group", of a "protected hydroxy group" and of a "protecting group for a group represented by —OH" include acyls (such as acetyl and benzoyl), tri(lower alkyl)silyls (such as trimethylsilyl and t-butyldimethylsilyl), lower alkyldiarylsilyls (such as t-butylphenylsilyl), ar(lower)alkyls that may have one or more suitable substituents (such as benzyl, trityl, p-nitrobenzyl and p-methoxybenzyl), lower alkyls substituted with lower alkoxys (such as methoxymethyl), lower alkyls substituted with aryls (such as trityl), lower alkoxycarbonyls (such as t-butyloxycarbonyl), heterohydrocarbon groups (such as tetrahydro-2H-pyran-2-yl), etc.

"Protected hydroxy groups" include acyl (such as acetyl and benzoyl)oxy, tri(lower alkyl)silyl (such as trimethylsilyl and t-butyldimethylsilyl)oxy, lower alkyldiarylsilyl (such as t-butyldiphenylsilyl)oxy, ar(lower)alkyl that may have one or more suitable substituents (such as benzyl, trityl, p-nitrobenzyl and p-methoxybenzyl)oxy, lower alkoxy-substituted lower alkyl (such as methoxymethyl)oxy, aryl-substituted lower alkyl (such as trityl)oxy, lower alkoxycarbonyl (such as t-butyloxycarbonyl)oxy, heterohydrocarbon (such as tetrahydro-2H-pyran-2-yl)oxy, etc.

A "protecting group for a carboxy group", a protecting group in a "protected carboxy group" and a protecting group for "a group represented by $—CO_2H$" include lower alkyls (such as methyl ethyl and t-butyl), lower alkoxy-substituted lower alkyls (such as methoxymethyl), lower alkyls substituted with lower alkoxy-substituted lower alkoxys (such as methoxyethoxymethyl), ar(lower)alkyls that may have one or more suitable substituents (such as benzyl, trityl, p-nitrobenzyl and p-methoxybenzyl), triaryl lower alkyls (such as triphenylmethyl), tri(lower alkyl)silyls (such as trimethylsilyl and t-butyldimethylsilyl), etc.

"Protected carboxy groups" include lower alkyl (such as methyl, ethyl and t-butyl)oxycarbonyls, lower alkoxy-substituted lower alkyl (such as methoxymethyl)oxycarbonyls, lower alkyls substituted with lower alkoxy-substituted lower alkoxy (such as methoxyethoxymethyl)oxycarbonyls, ar(lower)alkyl that may have one or more suitable substituents (such as benzyl trityl, p-nitrobenzyl and p-methoxybenzyl)oxycarbonyls, triaryl lower alkyl (such as triphenylmethyl)oxycarbonyls, trilower alkylsilyl (such as trimethylsilyl and t-butyldimethylsilyl)oxycarbonyls, etc.

A "protecting group for a sulfanil group", a protecting group in a "protected sulfanil group" and a "protecting group for a group represented by —SH" include lower alkyls (such as methyl, ethyl and t-butyl), ar(lower)alkyls that may have one or more suitable substituents (such as benzyl, trityl, p-nitrobenzyl and p-methoxybenzyl), aryl(lower alkoxy)carbonyls (such as 9-fluorenylmethylcarbonyl, etc.

"Protected sulfanyl groups" include lower alkyl (such as methyl, ethyl and t-butyl)thioethers, ar(lower)alkyl that may have one or more suitable substituents (such as benzyl trityl, p-nitrobenzyl and p-methoxybenzyl)thioethers, aryl-lower alkoxycarbonyl (such as 9-fluorenylmethylcarbonyl)thioethers, etc.

The "label" as in the "carbonyl group substituted with a substituent that functions as a label" includes compounds that themselves have fluorescence, those that are coordinated with a radioactive metal those that contain a radioactive isotope, those that are coordinated with a paramagnetic metal for MRI, those that have affinity with the target compound and are for use in isolating or purifying the target compound, etc. Examples of such compounds that themselves have fluorescence include coumarin, NBD (7-nitrobenz-2-oxa-1,3-diazole), BODIPY (registered trademark), TAMRA (5-(and -6-)carboxytetramethylrhodamine), pyrene, etc. Examples of those that are coordinated with a radioactive metal include porphorine, DOTA (1,4,7,10-tetraazacyclodecane-1,4,7,10-tetraacetic acid), DTPA (diethylenetriaminepentaacetic acid), etc. Examples of those that contain a radioactive isotope include derivatives containing $^{18}$F, $^{11}$C, $^{13}$N and/or $^{15}$O (such as trifluoro($^{18}$F) borate) and the like. Examples of those that are coordinated with a paramagnetic metal for MRI include gadolinium and the like. Examples of those that have affinity with the target compound and are for use in isolating or purifying the target compound include biotin. Examples of "carbonyl groups substituted with a substituent that functions as a label" include those that are represented by the formulae below.

[Chemical Formula 104]

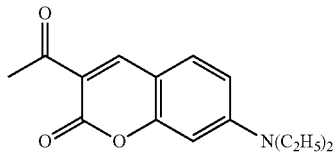

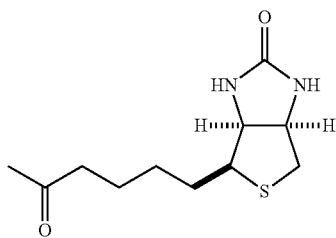

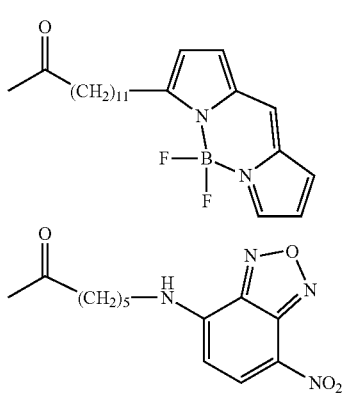

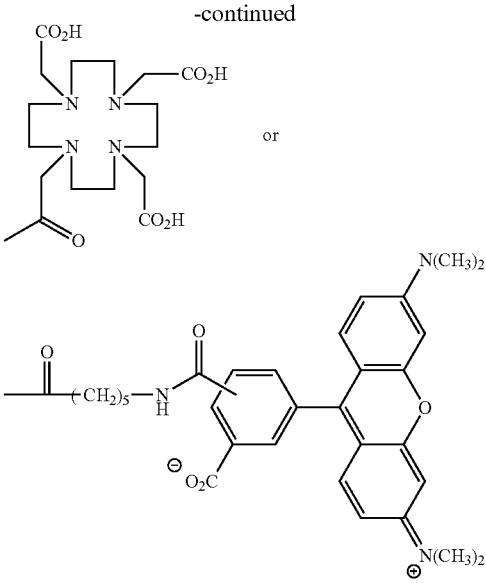

The compound represented by Formula (II) of the present invention is, as described above, a precursor useful in the production of the compound represented by Formula (III) and the compound represented by Formula (III). The compound represented by Formula (II) and the compound represented by Formula (III) are useful precursors of the compound represented by Formula (IV). The compound represented by Formula (II), the compound represented by Formula (III) and the compound represented by Formula (IV) promptly react with an amino group that is present within a molecule, preferably an amino group of a lysine residue, due to the presence of the hexatriene-β-keto moiety in the compounds, form a Schiff base, and then undergo cyclization. Therefore, there are advantages in that it is easy to perform labeling when a molecule is labeled, i.e., the rate of reaction for labeling is high and the reaction yield is high. Since the compound represented by Formula (II), the compound represented by Formula (III) and the compound represented by Formula (IV) have a substituent that functions as a label within the compounds, they are useful in tracking a molecule. Moreover, it is possible readily to produce the compound represented by Formula (II), the compound represented by Formula (III) and the compound represented by Formula (IV) from the compound represented by Formula (I) according to production methods as described above. Therefore, the compound represented by Formula (I) is a useful compound.

The compound represented by Formula (I) of the present invention is preferably such that, in the formula, $R^1$ is a group represented by —CH$_2$OH, —CH$_2$—OR$^{11}$ or —CHO, $R^2$ is a lower alkyl group, a lower alkyl group substituted with one or more substituents or a group represented by the formula -L$^2$-A$^2$-M$^2$, $R^3$ is a hydrogen atom or a group represented by the formula -L$^1$-A$^1$-M$^1$, the formula -L$^1$-N$_3$ or the formula:

-L$^1$-C≡CH, and [Chemical Formula 105]

Z is a divalent group derived from an aromatic hydrocarbon or a divalent group derived from an aromatic hydrocarbon substituted with one or more substituents; and in the formulae above, $L^1$ is a bond or a group represented by the formula —$(CH_2)_n$—CONH— or the formula —CONH—$(CH_2)_n$— (wherein n represents an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^1$ is a hydrogen atom, a group represented by —$NH_2$ or an acyl group, $M^2$ is a hydrogen atom or an acyl group, and $R^{11}$ is a protecting group for a hydroxyl group.

Moreover, the compound of the present invention represented by Formula (II) is preferably such that, in the formula, $R^1$ is a group represented by —$CH_2OH$ or —CHO, $R^2$ is a lower alkyl group or a lower alkyl group substituted with one or more substituents, $R^4$ is a group represented by the formula below:

[Chemical Formula 106]

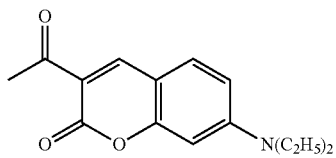

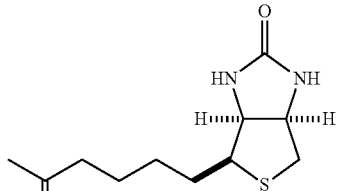

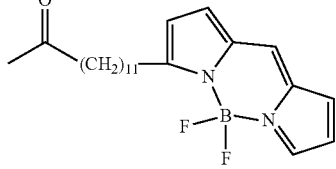

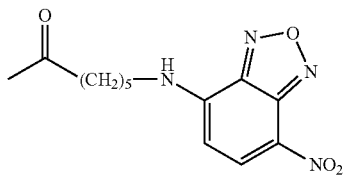

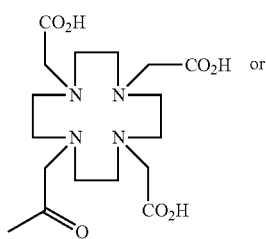

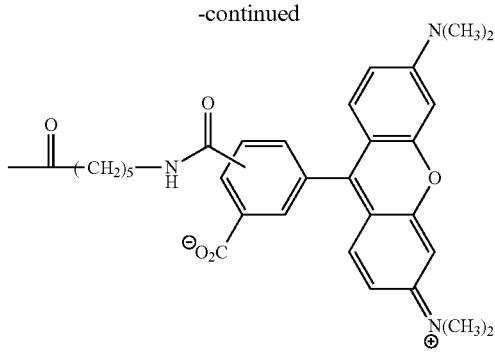

$X^1$ is a group represented by the formula -$L^1$-$A^1$-, the formula -$A^1$-$L^1$- or the formula below:

[Chemical Formula 107]

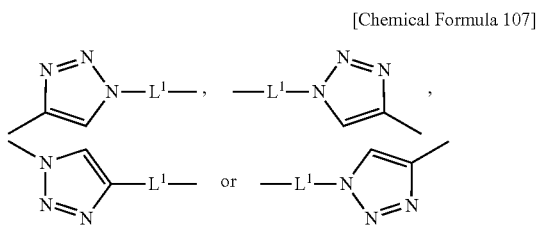

and Z is a divalent group derived from an aromatic hydrocarbon or a divalent group derived from an aromatic hydrocarbon substituted with one or more substituents; and in the formulae above, $L^1$ is a bond or a group represented by —$(CH_2)_n$—CONH— or —CONH—$(CH_2)_n$— (wherein n represents an integer of 1 to 20), and $A^1$ is a group represented by —O—, —$CO_2$—, —S— or —NH—.

Moreover, the compound of the present invention represented by Formula (III) is preferably such that, in the formula, $R^1$ is a group represented by —$CH_2OH$, —$CH_2$—$OR^{11}$ or —CHO, $R^3$ is a hydrogen atom or a group represented by the formula -$L^1$-$A^1$-$M^1$, the formula -$L^1$-$N_3$ or the formula:

-$L^1$-C≡CH, [Chemical Formula 108]

$R^5$ is a group represented by the formula below:

[Chemical FormulA 109]

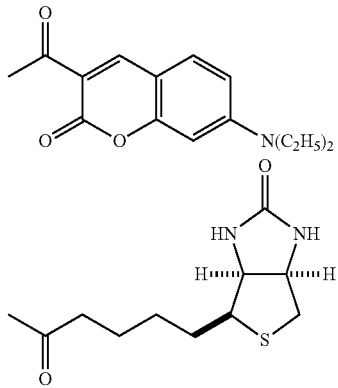

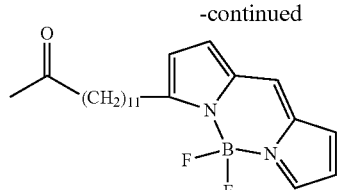

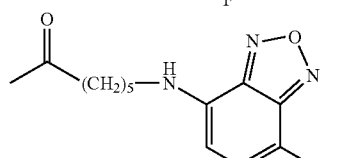

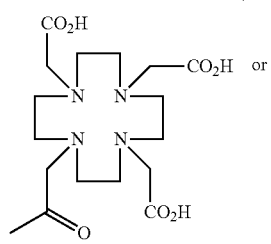

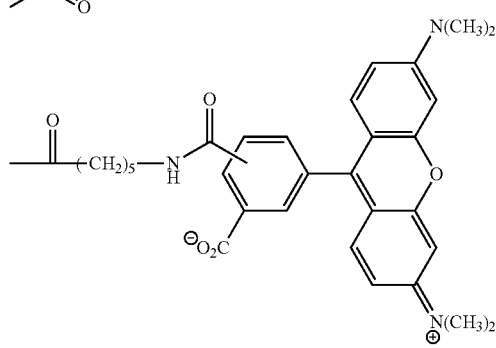

$X^2$ is a group represented by the formula $-L^2-A^2-L^3-$, and

Z is a divalent group derived from an aromatic hydrocarbon or a divalent group derived from an aromatic hydrocarbon substituted with one or more substituents; and in the formulae above, $L^1$ is a bond or a group represented by —$(CH_2)_n$—CONH— or —CONH—$(CH_2)_n$— (wherein n represents an integer of 1 to 20), $A^1$ is a group represented by —O—, —$CO_2$—, —S— or —NH—, $L_2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by —$(CH_2)_n$—O—$(CH_2)_m$— (wherein n and m each independently represent an integer of 1 to 20), $M^1$ is a hydrogen atom, a group represented by —$NH_2$ or an acyl group, and $R^{11}$ is a protecting group for a hydroxyl group.

Moreover, the compound of the present invention represented by Formula (IV) is preferably such that, in the formula, $R^1$ is a group represented by —$CH_2OH$, —CH—$OR^{11}$ or —CHO, $R^4$ is a group represented by the formula below:

[Chemical Formula 110]

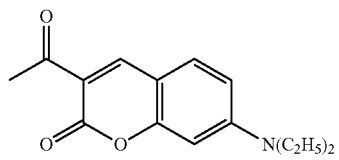

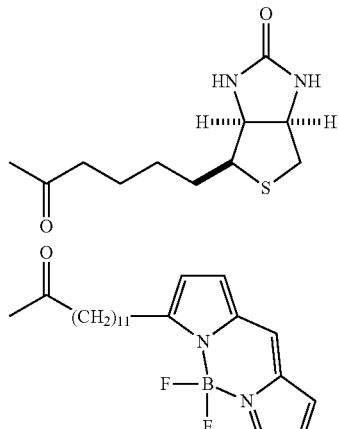

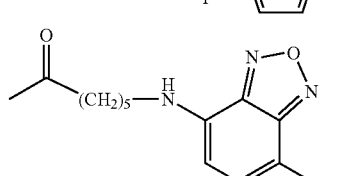

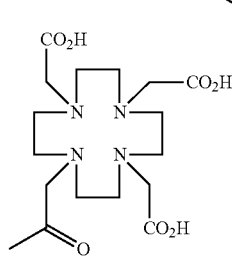

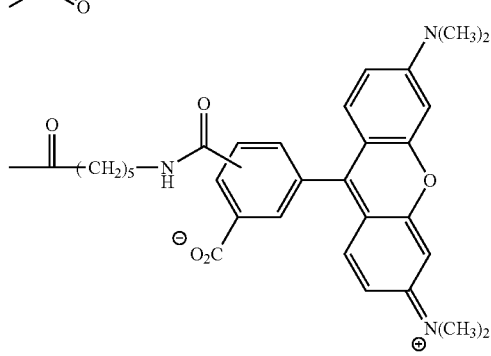

$R^5$ is a group represented by the formula below:

[Chemical Formula 111]

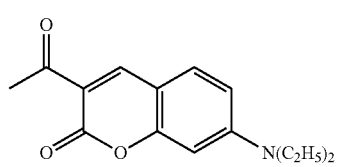

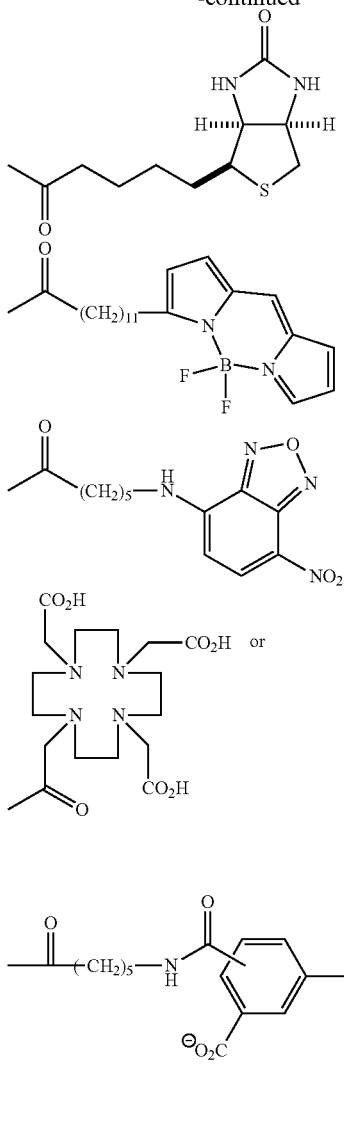

$X^1$ is a group represented by the formula -$L^1$-$A^1$-, the formula -$A^1$-$L^1$- or the formula below:

[Chemical Formula 112]

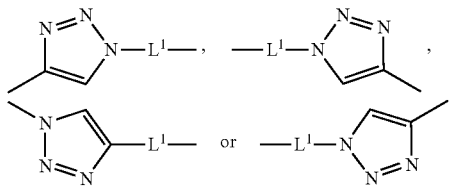

$X^2$ is a group represented by the formula -$L^2$-$A^2$-$L^3$-, and

Z is a divalent group derived from an aromatic hydrocarbon or a divalent group derived from an aromatic hydrocarbon substituted with one or more substituents; and in the formulae above, $L^1$ is a bond or a group represented by —$(CH_2)_n$—CONH— or —CONH—$(CH_2)_n$— (wherein n represents an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by —$(CH_2)_n$—CONH— or —CONH—$(CH_2)_n$— (wherein n represents an integer of 1 to 20), and $R^{11}$ is a protecting group for a hydroxyl group.

Moreover, the compound of the present invention represented by Formula (I) is more preferably such that, in the formula, $R^1$ refers to a group represented by —$CH_2OH$, —$CH_2$—OSi(t-Bu)$Ph_2$ or —CHO, $R^2$ refers to a lower alkyl group or a group represented by the formula -$L^2$-$A^2$-M, $R^3$ refers to a hydrogen atom or a group represented by the formula -$L^1$-$A^1$-M, a group represented by the formula -$L^1$-$N_3$ or a group represented by the formula -$L^1$-C≡CH, and Z refers to a divalent group derived from an aromatic hydrocarbon; and in the formulae above, $L^1$ is a bond or a group represented by —$(CH_2)_n$—CONH— or —CONH—$(CH_2)_n$— (wherein n represents an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, and M refers to a hydrogen atom or an acyl group.

Moreover, the compound of the present invention represented by Formula (II) is more preferably such that, in the formula, $R^1$ refers to a group represented by —$CH_2OH$ or —CHO, $R^2$ refers to a lower alkyl group, $R^4$ refers to a group represented by the formula below:

[Chemical Formula 113]

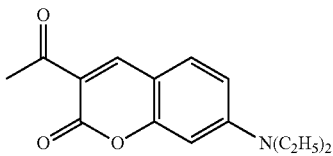

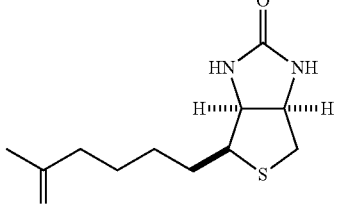

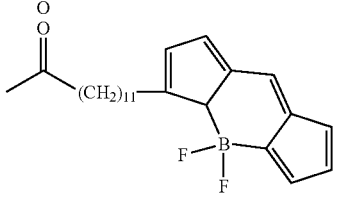

-continued

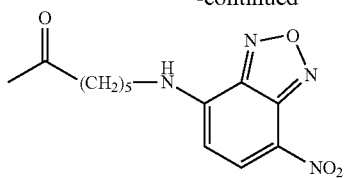

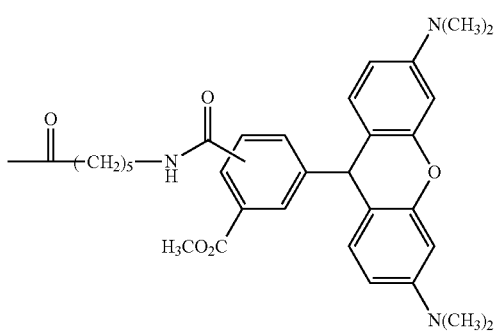

$X^1$ refers to a group represented by the formula $-L^1-A^1-$, a group represented by the formula $-A^1-L^1-$ or a group represented by the formula below:

[Chemical Formula 114]

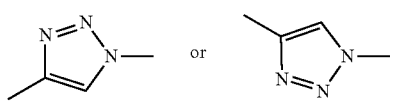

and Z refers to a divalent group derived from an aromatic hydrocarbon; and, in the formulae above, $L^1$ is a bond or a group represented by $-(CH_2)_n-CONH-$ or $-CONH-(CH_2)_n-$ (wherein n represents an integer of 1 to 20), and $A^1$ is a group represented by $-O-$, $-CO_2-$, $-S-$ or $-NH-$.

Moreover, the compound represented by Formula (III) of the present invention is more preferably such that, in the formula, $R^1$ refers to a group represented by $-CH_2OH$, $-CH_2-OSi(t-Bu)Ph_2$ or $-CHO$, $R^3$ refers to a hydrogen atom or a group represented by the formula $-L^1-A^1-M$, a group represented by the formula $-L^1-N_3$ or a group represented by the formula $-L^1-C\equiv CH$, $R^5$ is a group represented by the formula below:

[Chemical Formula 115]

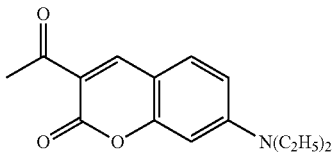

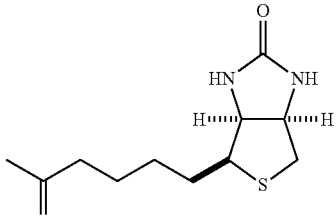

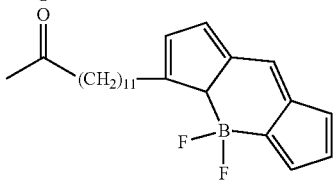

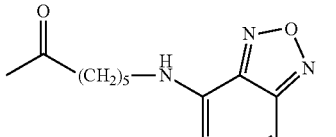

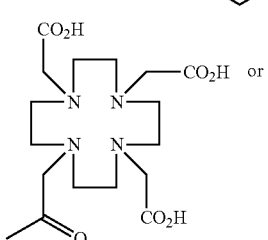

$X^2$ refers to a group represented by the formula $-L^2-A^2-L^3-$, and

Z refers to a divalent group derived from an aromatic hydrocarbon; and, in the formulae above, $L^1$ is a bond or a group represented by $-(CH_2)_n-CONH-$ or $-CONH-(CH_2)_n-$ (wherein n represents an integer of 1 to 20), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20), $A^2$ is a group represented by $-O-$, $-CO_2-$, $-S-$ or $-NH-$, $L^3$ is a bond, and M refers to a hydrogen atom or an acyl group.

Moreover, the compound of the present invention represented by Formula (IV) is more preferably such that, in the formula, $R^1$ refers to a group represented by —$CH_2OH$, —$CH_2$—$OSi(t-Bu)Ph_2$ or —CHO, $R^4$ is a group represented by the formula below:

[Chemical Formula 116]

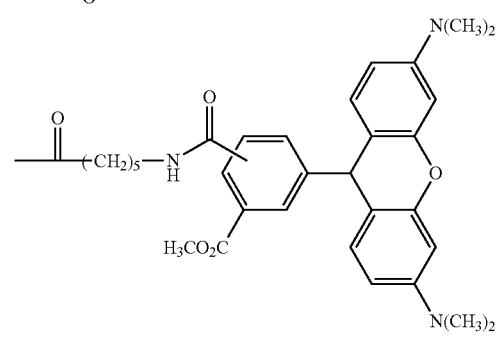

$R^5$ is a group represented by the formula below:

[Chemical Formula 117]

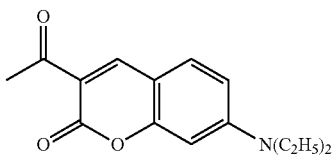

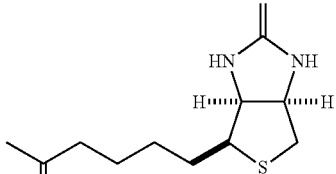

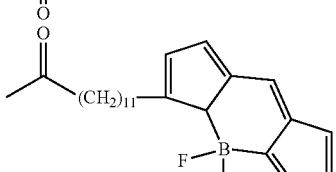

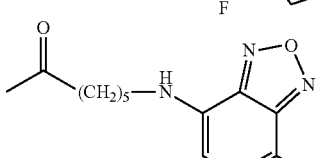

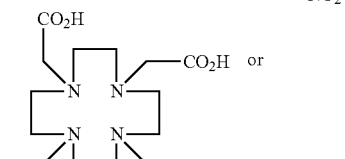

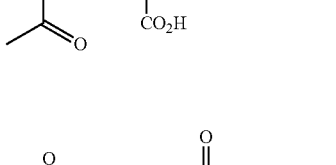

$X^1$ is a group represented by the formula -$L^1$-$A^1$-, a group represented by the formula -$A^1$-$L^1$- or a group represented by the formula below:

[Chemical Formula 118]

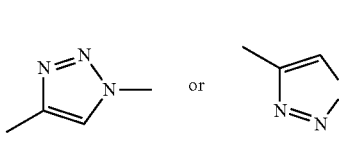

$X^2$ refers to a group represented by the formula $-L^2-A^2-L^3-$, and

Z refers to a divalent group derived from an aromatic hydrocarbon; and, in the formulae above, $L^1$ is a bond or a group represented by $-(CH_2)_n-CONH-$ or $-CONH-(CH_2)_n-$ (wherein n represents an integer of 1 to 20), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20), $A^2$ is a group represented by $-O-$, $-CO_2-$, $-S-$ or $-NH-$, and $L^3$ is a bond.

Moreover, the compound of the present invention represented by Formula (I) is further preferably such that, in the formula, $R^1$ is a group represented by $-CH_2OH$ or $-CH_2-OSi(t-Bu)Ph_2$, $R^2$ refers to a lower alkyl group or a group represented by the formula $-(CH_2)_n-O-(CH_2)_m-NH-M^2$ (wherein n and m each independently represent an integer of 1 to 20, and $M^2$ is an acyl group), $R^3$ is a hydrogen atom or a group represented by the formula $-L^1-NH-M^1$ (wherein $L^1$ is a bond or a group represented by the formula $-(CH_2)_n-CONH-$ or the formula $-CONH-(CH_2)_n-$ (wherein n represents an integer of 1 to 20) and $M^1$ is a hydrogen atom or an acyl group), and Z is a divalent group derived from an aromatic hydrocarbon.

Moreover, the compound of the present invention represented by Formula (II) is further preferably such that, in the formula, $R^1$ is a group represented by $-CH_2OH$ or $-CHO$, $R^2$ is a lower alkyl group, $R^4$ is a group represented by the formula below:

[Chemical Formula 119]

$X^1$ is a group represented by the formula $-L^1-NH-$ or the formula $-NH-L^1-$ (wherein $L^1$ is a bond or a group represented by $-(CH_2)_n-CONH-$ or $-CONH-(CH_2)_n-$ (wherein n represents an integer of 1 to 20)), and Z is a divalent group derived from an aromatic hydrocarbon.

Moreover, the compound of the present invention represented by Formula (III) is further preferably such that, in the formula, $R^1$ is a group represented by $-CH_2OH$, $-CH_2-OSi(t-Bu)Ph_2$ or $-CHO$, $R^3$ is a hydrogen atom or a group represented by $-NH_2$, $R^5$ is a group represented by the formula below:

[Chemical Formula 120]

$X^2$ is a group represented by the formula $-L^2-NH-L^3-$ (wherein, $L^2$ is a bond or a group represented by $-(CH_2)_n-O-(CH_2)_m-$ (wherein n and m each independently represent an integer of 1 to 20), $L^3$ is a bond or a group represented by $-(CH_2)_n-O-(CH_2)_m-$ (wherein n and m each independently represent an integer of 1 to 20)), and Z refers to a divalent group derived from an aromatic hydrocarbon.

Moreover, the compound of the present invention represented by Formula (IV) is further preferably such that, in the formula, $R^1$ is a group represented by —$CH_2OH$, —$CH_2$—$OSi(t-Bu)Ph_2$ or —CHO, $R^4$ is a group represented by the formula below:

[Chemical Formula 121]

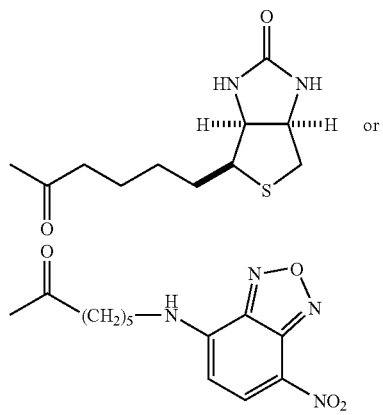

$R^5$ is a group represented by the formula below:

[Chemical Formula 122]

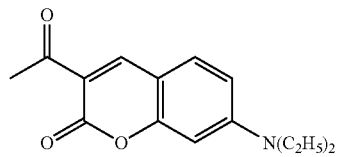

$X^1$ is a group represented by the formula -$L^1$-NH— or the formula —NH-$L^1$-, $X^2$ is a group represented by the formula -$L^2$-NH-$L^3$-, and Z is a divalent group derived from an aromatic hydrocarbon; and, in the formulae above, $L^1$ is a bond or a group represented by —$(CH_2)_n$—CONH— or —CONH—$(CH_2)_n$— (wherein n represents an integer of 1 to 20), $L^2$ is a bond or a group represented by —$(CH_2)_n$—O—$(CH_2)_m$— (wherein n and m each independently represent an integer of 1 to 20), and $L^3$ is a bond or a group represented by —$(CH_2)_n$—CONH— or —CONH—$(CH_2)_n$— (wherein n represents an integer of 1 to 20).

Moreover, it is even more preferable that the compound of the present invention represented by Formula (I) is selected from the group consisting of a compound represented by General Formula (I) wherein,
$R^1$ is a group represented by —$CH_2OH$,
$R^2$ is an ethyl group,
$R^3$ is a group represented by —$NH_2$, and
Z is a 1,4-phenylene group;
a compound represented by General Formula (I) wherein
$R^1$ is a group represented by —$CH_2$—$OSi(t-Bu)Ph_2$,
$R^2$ is a group represented by —$(CH_2)_2$—O—$(CH_2)_2$—NH—$CO(t-Bu)_3$,
$R^3$ is a hydrogen atom, and
Z is a 1,4-phenylene group;
a compound represented by General Formula (X) wherein
$R^1$ is a group represented by —$CH_2$—$OSi(t-Bu)Ph_2$,
$R^2$ is a group represented by —$(CH_2)_2$—O—$(CH_2)_2$—NH—$CO(t-Bu)_3$,
$R^3$ is a group represented by —NH—$CO(t-Bu)_3$, and
Z is a 1,4-phenylene group; and
a compound represented by General Formula (I) wherein
$R^1$ is a group represented by —$CH_2$—OH,
$R^2$ is an ethyl group,
$R^3$ is a group represented by —NH—CO—$CH_2$—$NH_2$, and
Z is a 1,4-phenylene group.

Specific examples of such compounds represented by Formula (Include:
ethyl (E,E)-4-hydroxy-2-(4-(2-aminoacetamide)styryl)but-2-enoate (Compound 5),
ethyl (E,E)-4-hydroxy-2-(4-aminostyryl)but-2-enoate (Compound 30),
2-(2-(7-diethylaminocoumarin)-3-carbonylaminoethoxy)ethyl (E,E)-4-hydroxy-2-(4-aminostyryl)but-2-enoate,
2-(2-N-tert-butoxycarbonylaminoethoxy)ethyl (E,E)-4-(tert-butyldiphenylsilanyloxy)-2-styrylbut-2-enoate (Compound 45),
2-(2-N-tert-butoxycarbonylaminoethoxy)ethyl (E,E)-4-(tert-butyldiphenylsilanyloxy)-2-(4-N-tert-butoxycarbonylaminostyryl)but-2-enoate (Compound 46), etc.

Moreover, it is even more preferable that the compound of the present invention represented by Formula (II) is selected from the group consisting of a compound represented by Formula (II) wherein,
$R^1$ is a group represented by —$CH_2OH$,
$R^2$ is an ethyl group,
$R^4$—$X^1$— is a group represented by the formula:

[Chemical Formula 123]

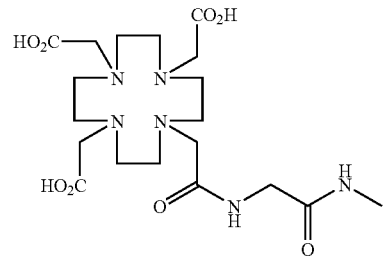

and Z is a 1,4-phenylene group;
a compound represented by Formula (II) represented by Formula (II) wherein,
$R^1$ is a group represented by —CHO,
$R^2$ is an ethyl group,
$R^4$—$X^1$— is a group represented by the formula:

[Chemical Formula 124]

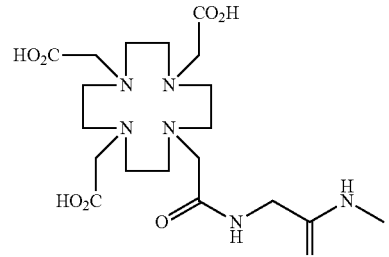

and Z is a 1,4-phenylene group;
a compound represented by Formula (II) wherein,
  $R^1$ is a group represented by —$CH_2OH$,
  $R^2$ is an ethyl group,
  $R^4$—$X^1$— is a group represented by the formula:

[Chemical Formula 125]

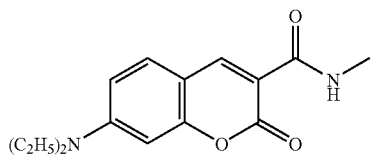

and Z is a 1,4-phenylene group;
a compound represented by Formula (II) wherein,
  $R^1$ is a group represented by —$CH_2OH$,
  $R^2$ is an ethyl group,
  $R^4$—$X^1$— is a group represented by the formula:

[Chemical Formula 126]

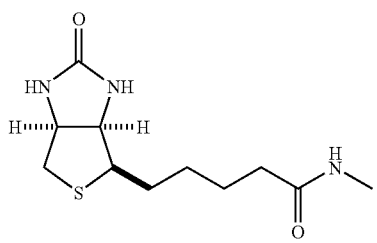

and Z is a 1,4-phenylene group;
a compound represented by Formula (II) wherein,
  $R^1$ is a group represented by —$CH_2OH$,
  $R^2$ is an ethyl group,
  $R^4$—$X^1$— is a group represented by the formula:

[Chemical Formula 127]

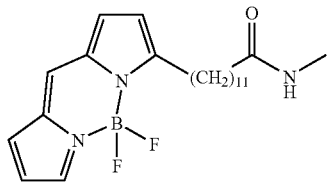

and Z is a 1,4-phenylene group;
a compound represented by Formula (II) wherein,
  $R^1$ is a group represented by —$CH_2OH$,
  $R^2$ is an ethyl group,
  $R^4$—$X^1$— is a group represented by the formula:

[Chemical Formula 128]

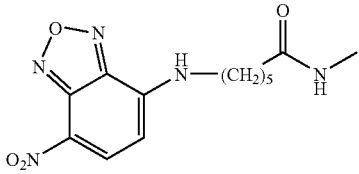

and Z is a 1,4-phenylene group;
a compound represented by Formula (II) wherein,
  $R^1$ is a group represented by —CHO,
  $R^2$ is an ethyl group,
  $R^4$—$X^1$— is a group represented by the formula:

[Chemical Formula 129]

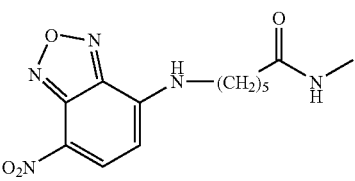

and Z is a 1,4-phenylene group;
a compound represented by Formula (II) wherein,
  $R^1$ is a group represented by —$CH_2OH$,
  $R^2$ is an ethyl group,
  $R^4$—$X^1$— is a group represented by the formula:

[Chemical Formula 130]

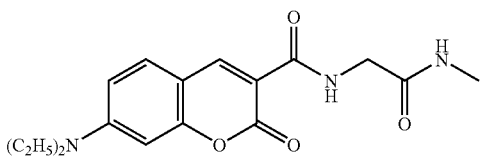

and Z is a 1,4-phenylene group;
a compound represented by Formula (II) wherein,
  $R^1$ is a group represented by —CHO,
  $R^2$ is an ethyl group,
  $R^4$—$X^1$— is a group represented by the formula:

[Chemical Formula 131]

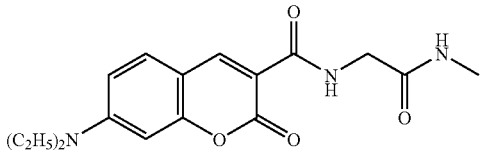

and Z is a 1,4-phenylene group;
a compound represented by Formula (II) wherein
  $R^1$ is a group represented by —$CH_2OH$,
  $R^2$ is an ethyl group, R⁴—X¹— is a group represented by the formula:

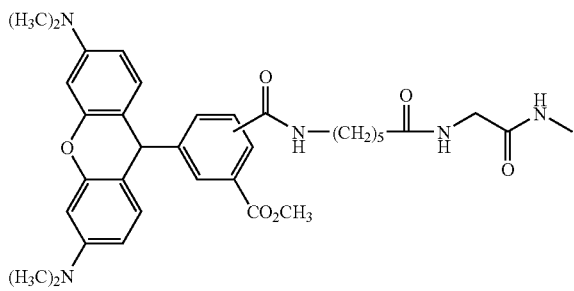

and Z is a 1,4-phenylene group; and
a compound represented by Formula (II) wherein
R¹ is a group represented by —CHO,
R² is an ethyl group,
R⁴—X¹— is a group represented by the formula:

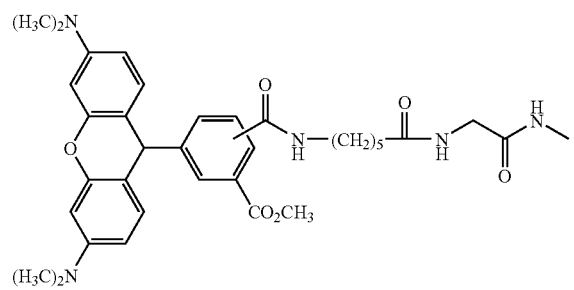

and Z is a 1,4-phenylene group.

Specific examples of such compounds represented by Formula (II) include:

10-(2-(2-(4-((1E,E3)-ethoxycarbonyl-5-hydroxypenta-1,3-dienyl)phenylamino)-2-oxoethyl amino)-2-oxoethyl)-1,4,7,10-tetracyclododecane-1,4,7-triacetic acid (Compound 7), 10-(2-(2-(4-((1E,3E)-3-ethoxycarbonyl-5-oxopenta-1,3-dienyl)phenylamino)-2-oxoethylamino)-2-oxoethyl)-1,4,7,10-tetraazacyclododecane-1,4,7-triacetic acid (Compound 8), ethyl (E,E)-4-hydroxy-2-(4-(2-(6-(tetramethylrhodamine-5-(and -6)-carboxamido)hexaneamide)acetamide)styryl)but-2-enoate (Compound 13), ethyl (E,E)-4-oxo-2-(4-(2-(6-(tetramethylrhodamine-5-(and -6)-carboxamido)hexaneamide)acetamide)styryl)but-2-enoate (Compound 15), ethyl (E,E)-4-hydroxy-2-(4-(7-diethylaminocoumarin-3-carboxamide)styryl)but-2-enoate (Compound 32), ethyl (E,E)-4-hydroxy-2-((4-hexahydro-2-oxo-1H-thieno[3,4-d]imidazole-4-pentanamide)styryl)but-2-enoate (Compound 34), ethyl (E,E)-4-hydroxy-2-(4-(6-((4,4-difluoro-5,7-dimethyl-4-bora-3a,4a-diaza-s-indacene-3-propionylamino)dodecanamide)styryl)but-2-enoate (Compound 38), ethyl (E,E)-4-hydroxy-2-(4-(2-(6-(N-(7-nitrobenz-2-oxa-1,3-diazol-4-yl)amino)hexanamide)styryl)but-2-enoate (Compound 36), ethyl (E,E)-4-oxo-2-(4-(2-(6-(N-(7-nitrobenz-2-oxa-1,3-diazol-4-yl)amino)hexanamide)styryl)but-2-enoate (Compound 39), ethyl (E,E)-4-hydroxy-2-(4-(2-(7-diethylaminocoumarin-3-carboxamido)acetamide)styryl)but-2-enoate (Compound 17), ethyl (E,E)-4-oxo-2-(4-(2-(7-diethylaminocoumarin-3-carboxamido)acetamide)styryl)but-2-enoate (Compound 18), etc.

Moreover, it is even more preferable that the compound of the present invention represented by Formula (III) is selected from the group consisting of a compound represented by Formula (III) wherein,
R¹ is a group represented by —CH₂—OSi(t-Bu)Ph₂,
R⁸ is a hydrogen atom,
R⁵—X²— is a group represented by the formula:

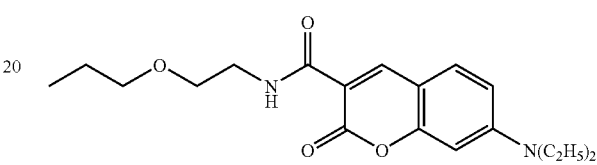

and Z is a 1,4-phenylene group;
a compound represented by Formula (III) wherein,
R¹ is a group represented by —CH₂—OH,
R³ is a hydrogen atom,
R⁵—X²— is a group represented by the formula:

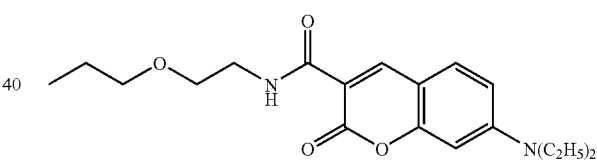

and Z is a 1,4-phenylene group;
a compound represented by Formula (III) wherein,
R¹ is a group represented by —CHO,
R³ is a hydrogen atom,
R⁵—X²— is a group represented by the formula:

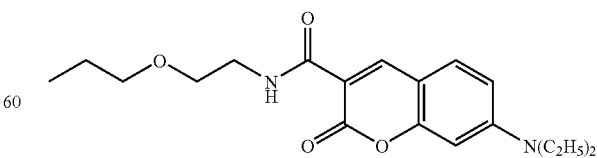

and Z is a 1,4-phenylene group; and
a compound represented by Formula (III) wherein,
R¹ is a group represented by —CH₂—OSi(t-Bu)Ph₂, $R^3$ is a group represented by —$NH_2$, $R^5$—$X^2$— is a group represented by the formula:

[Chemical Formula 137]

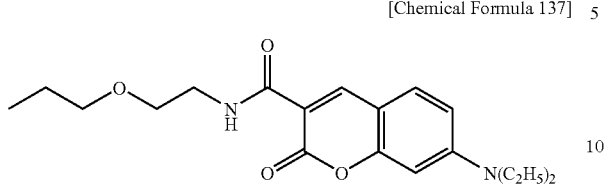

and Z is a 1,4-phenylene group.

Specific examples of such compounds represented by Formula (III) include:

2-(2-(7-diethylaminocoumarin)-3-carbonylaminoethoxy) ethyl (E,E)-4-oxo-2-(4-aminostyryl)but-2-enoate, 2-(2-(7-diethylaminocoumarin)-3-carbonylaminoethoxy) ethyl (E,E)-4-(tert-butyldiphenylsilanyloxy)-2-styrylbut-2-enoate (Compound 48), 2-(2-(7-diethylaminocoumarin-3-carbonylaminoethoxy) ethyl (E,E)-4-hydroxy-2-styrylbut-2-enoate (Compound 49), 2-(2-(7-diethylaminocoumarin)-3-carbonylaminoethoxy) ethyl (E,E)-4-oxo-2-styrylbut-2-enoate (Compound 50), 2-(2-(7-diethylaminocoumarin)-3-carbonylaminoethoxy) ethyl (E,E)-4-(tert-butyldiphenylsilanyloxy)-2-(4-aminostyryl)but-2-enoate (Compound 51), etc.

Moreover, it is even more preferable that the compound of the present invention represented by Formula (V is selected from the group consisting of a compound represented by Formula (III) wherein, $R^1$ is a group represented by —CH—OSi(t-Bu)Ph$_2$, $R^4$—$X^1$— is a group represented by the formula:

[Chemical Formula 138]

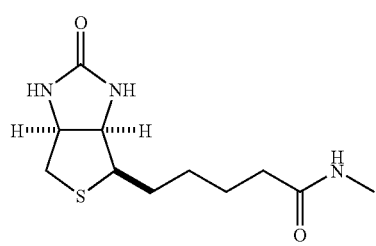

$R^5$—$X^2$— is a group represented by the formula:

[Chemical Formula 139]

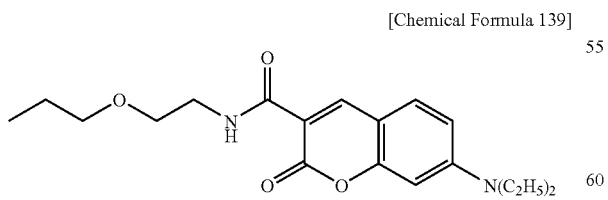

and Z is a 1,4-phenylene group;
a compound represented by Formula (III) wherein,
$R^1$ is a group represented by —$CH_2$—OH,
$R^4$—$X^1$— is a group represented by the formula:

[Chemical Formula 140]

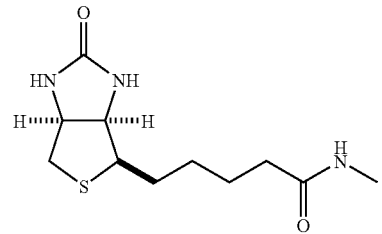

$R^5$—$X^2$— is a group represented by the formula:

[Chemical Formula 141]

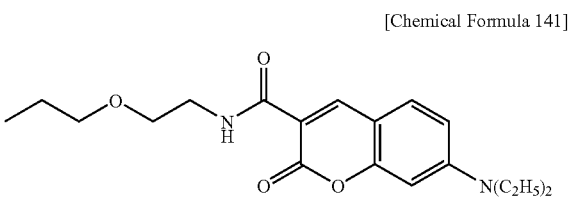

and Z is a 1,4-phenylene group;
a compound represented by Formula (III) wherein,
$R^1$ is a group represented by —$CH_2$—OSi(t-Bu)Ph$_2$,
$R^4$—$X^1$— is a group represented by the formula:

[Chemical Formula 142]

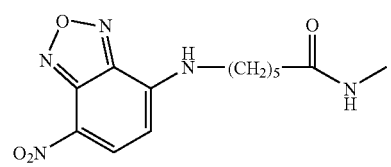

$R^5$—$X^2$— is a group represented by the formula:

[Chemical Formula 143]

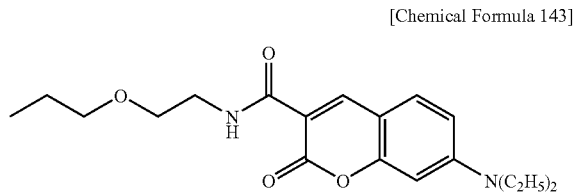

and Z is a 1,4-phenylene group;
a compound represented by Formula (III) wherein,
$R^1$ is a group represented by —$CH_2OH$,
$R^4$—$X^1$— is a group represented by the formula:

[Chemical Formula 144]

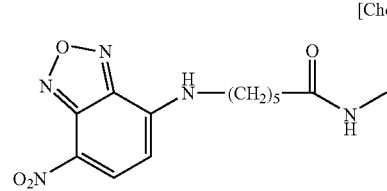

$R^5-X^2-$ is a group represented by the formula:

[Chemical Formula 145]

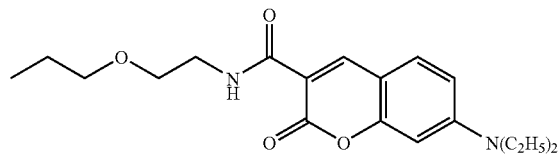

and Z is a 1,4-phenylene group; and
a compound represented by Formula (III) wherein,
$R^1$ is a group represented by —CHO,
$R^4-X^1-$ is a group represented by the formula:

[Chemical Formula 146]

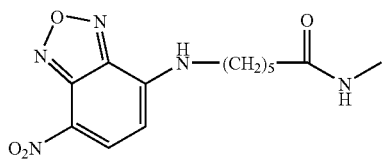

$R^5-X^2-$ is a group represented by the formula:

[Chemical Formula 147]

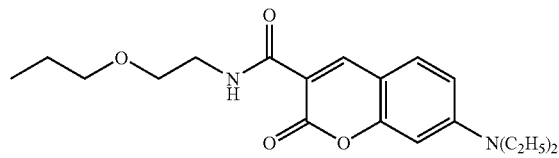

and Z is a 1,4-phenylene group.

Specific examples of such compounds represented by Formula (IV) include:

2-(2-(7-diethylaminocoumarin)-3-carbonylaminoethoxy) ethyl (E,E)-4-oxo-2-((6-(N-(7-nitrobenz-2-oxa-1,3-diazol-4-yl)amino)hexanamide)styryl)but-2-enoate, 2-(2-(7-diethylaminocoumarin)-3-carbonylaminoethoxy) ethyl (E,E)-4-(tert-butyldiphenylsilanyloxy)-2-((4-hexahydro-2-oxo-1H-thieno[3,4-d]imidazole-4-pentanamide) styryl)but-2-enoate (Compound 52), 2-(2-(7-diethylaminocoumarin)-3-carbonylaminoethoxy) ethyl (E,E)-4-hydroxy-2-((4-hexahydro-2-oxo-1H-thieno[3,4-d]imidazole-4-pentanamide)styrylbut-2-enoate (Compound 53), 2-(2-(7-diethylaminocoumarin)-3-carbonylaminoethoxy) ethyl (E,E)-4-(tert-butyldiphenylsilanyloxy)-2-((6-(N-(7-nitrobenz-2-oxa-1,3-diazol-4-yl)amino)hexanamide) styryl) but-2-enoate (Compound 54), 2-(2-(7-diethylaminocoumarin)-3-carbonylaminoethoxy) ethyl (E,E)-4-hydroxy-2-((6-(N-(7-nitrobenz-2-oxa-1,3-diazol-4-yl)amino)hexanamide)styryl)but-2-enoate (Compound 55), 2-(2-(7-diethylaminocoumarin)-3-carbonylaminoethoxy) ethyl (E,E)-4-oxo-2-((6-(N-(7-nitrobenz-2-oxa-1,3-diazol-4-yl)amino)hexanamide)styryl)but-2-enoate (Compound 56), etc.

Methods for producing the compound represented by Formula (I), the compound represented by Formula (II), the compound represented by Formula (III) and the compound represented by Formula (IV) of the present invention are described in detail below.

Production Method 1

The compound represented by Formula (I) can be produced, for example, according to the following method.

Scheme 1

[Chemical Formula 148]

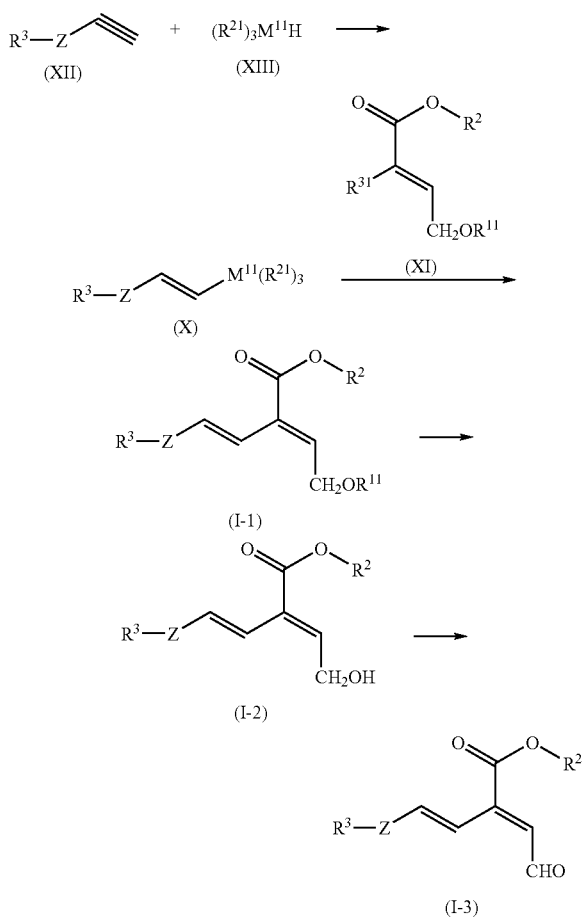

In the scheme above, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH, [Chemical Formula 149]

Z is a group represented by the formula below:

[Chemical Formula 150]

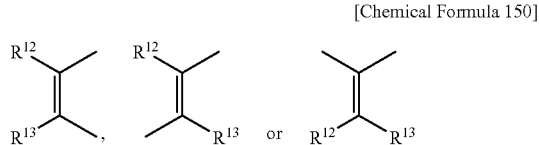

or a divalent group derived from an aromatic hydrocarbon or a divalent group derived from an aromatic hydrocarbon substituted with one or more substituents, $M^{11}$ is Zn, Sn, B, Al, Mg, Si, As, Cu or Zr, and $R^{21}$ is a lower alkyl group, an aryl group, a heteroaryl group, a hydroxyl group, an alkoxy group or a halogen atom.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^1$ is a hydrogen atom, a group represented by —OH, —$CO_2$H, —SH or —$NH_2$, or a protecting group for a group represented by —OH, —$CO_2$H, —SH or —$NH_2$, $M^2$ is a hydrogen atom or a protecting group for a group represented by —OH, —$CO_2$H, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, and $R^{31}$ is a halogen atom.

Specifically, by reacting an acetylene compound represented by General Formula (XII) and a metallic compound represented by Formula (XII) in the presence of a radical initiator (such as AIBN), a coupling compound represented by Formula (X) can be obtained. This reaction can be performed at, for example, 25 to 200° C. and preferably 70 to 120° C. Moreover, this reaction can be performed in a nonpolar solvent such as tetrahydrofuran, ether, benzene, toluene or xylene.

Next, by subjecting the compound represented by Formula (X) and an α,β-unsaturated ketone compound represented by Formula (XI) to a coupling reaction, a compound represented by Formula (I-1) can be obtained. The compound represented by Formula (I-1) is a compound represented by Formula (I) wherein $R^1$ is a group represented by —$CH_2OR^{11}$. It is preferable to perform the coupling reaction in the presence of a catalyst. Examples of such catalysts include palladium, nickel and like catalysts, in particular, $Pd(dba)_2$, $Pd(PPh_3)_4$, $Ni(PPh_3)_4$, $Pd(PPh_3)_2Cl_2$, $PdCl_2$, etc. When such a catalyst is used, it is preferable to use a catalytic aid. Examples of such catalytic aids include $P(2-furyl)_3$, $PPh_3$, dba (dibenzylideneacetone), etc. The coupling reaction can be performed at, for example, 25 to 200° C. and preferably 70 to 120° C. Moreover, the coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Next, by removing $R^{11}$ in the compound represented by Formula (I-1), a compound represented by Formula (I-2) can be obtained. The compound represented by Formula (I-2) is a compound represented by Formula (I) wherein $R^1$ is a group represented by $CH_2OH$. Since $R^{11}$ is a protecting group for a hydroxyl group, $R^{11}$ can be removed by treating it under suitable conditions according to the type of protecting group. For example, when $R^{11}$ is tetrahydro-2H-pyran-2-yl (THP), examples of such suitable conditions include treatment with acidic water, acid treatment with p-toluenesulfonic acid (p-TsOH), acid treatment with pyridinium paratoluene sulfinate (PPTS), and the like.

Next, by oxidizing the compound represented by Formula (I-2), a compound represented by Formula (I-3) can be obtained. The compound represented by Formula (I-3) is a compound represented by Formula (I) wherein $R^1$ is a group represented by —CHO. The oxidation conditions are not limited insofar as the conditions for oxidizing a primary alcohol to an aldehyde. The oxidation conditions involve, for example, pyridinium dichromochromate (PDC), a Dess-Martin reagent, manganese dioxide, tetrapropylammonium perruthenate (TPAP) oxidation, Ishii oxidation, Swern oxidation, Corey-Kim oxidation, natural oxidation, enzymatic oxidation, $PtO_2$ oxidation, etc. The oxidation reaction can be carried out at, for example, 10 to 100° C. and preferably 25 to 50° C. The oxidation reaction can be carried out in a nonpolar solvent such as tetrahydrofuran, ether, benzene, toluene or xylene as well as in a polar solvent such as dimethylformamide (DMF), dimethylsulfoxide (DMSO), acetonitrile, propionitrile or diethoxyethane (DME).

The compound represented by Formula XII), the compound represented by Formula (XIII) and the compound represented by Formula (XI) may be obtained commercially or may be produced according to published literature.

Production Method 2

The compound represented by Formula (II can be produced according to, for example, the following method or the like. First, the compound represented by Formula (II) wherein $R^1$ is a group represented by —$CH_2$—$OR^{11}$ and $X^1$ is a group represented by the formula -$A^1$-$L^1$- or -$L^1$-$A^1$- can be produced according to, for example, the following method.

Scheme 2

[Chemical Formula 151]

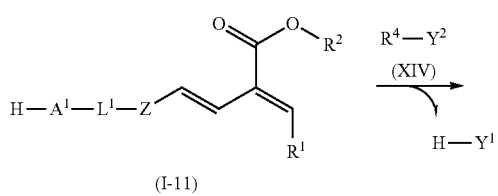

(I-11)

-continued $$R^4-A^1-L^1-Z\diagup\diagdown\diagup\diagdown\diagup\!\!\!\!\!{}^{CO_2R^2}_{R^1}$$

(II-1)

$$H-L^1-A^1-Z\diagup\diagdown\diagup\diagdown\diagup\!\!\!\!\!{}^{CO_2R^2}_{R^1}$$

(I-12)

$$\xrightarrow{R^4-Y^1\atop (XIV)}\;\;H-Y^1$$

$$R^4-L^1-A^1-Z\diagup\diagdown\diagup\diagdown\diagup\!\!\!\!\!{}^{CO_2R^2}_{R^1}$$

(II-2)

In Formula (I-11) and Formula (I-12) above, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, and Z is a group represented by the formula below:

[Chemical Formula 152]

$$\underset{R^{13}}{\overset{R^{12}}{\diagup\!\!\!\diagdown}}\;,\;\;\underset{R^{13}}{\overset{R^{12}}{\diagup\!\!\!\diagdown}}\;\;or\;\;\underset{R^{12}}{\overset{}{\diagup\!\!\!\diagdown}}R^{13}$$

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)$—O—$(CH_2)_3$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, in Formula (XIV) above, $R^4$ is a carbonyl group substituted with a substituent that functions as a label and $Y^1$ is a leaving group.

Moreover, in Formula (II-1) and Formula (II-2) above, $R^1$ is a group represented by —$CH_2$—$OR^{11}$, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label, and Z is a group represented by the formula below:

[Chemical Formula 153]

$$\underset{R^{13}}{\overset{R^{12}}{\diagup\!\!\!\diagdown}}\;,\;\;\underset{R^{13}}{\overset{R^{12}}{\diagup\!\!\!\diagdown}}\;\;or\;\;\underset{R^{12}}{\overset{}{\diagup\!\!\!\diagdown}}R^{13}$$

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

Specifically, for example, by coupling a compound represented by Formula (I-11) with a compound represented by Formula (XIV) to remove a compound represented by the formula $Y^1$—H, a compound represented by Formula (II-1) can be obtained. Alternatively by coupling a compound represented by Formula (I-12) with a compound represented by Formula (XIV) remove a compound represented by the formula $Y^1$—H, a compound represented by Formula (II-2) can be obtained. These coupling reactions can be performed at, for example, 10 to 60° C. and preferably 25 to 40° C. These coupling reactions can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

In addition, the compound represented by Formula (II) wherein $R^1$ is a group represented by —$CH_2$—$OR^{11}$ and $X^1$ is:

[Chemical Formula 154]

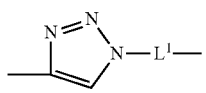

can be produced according to, for example, the following method.

Scheme 3

[Chemical Formula 155]

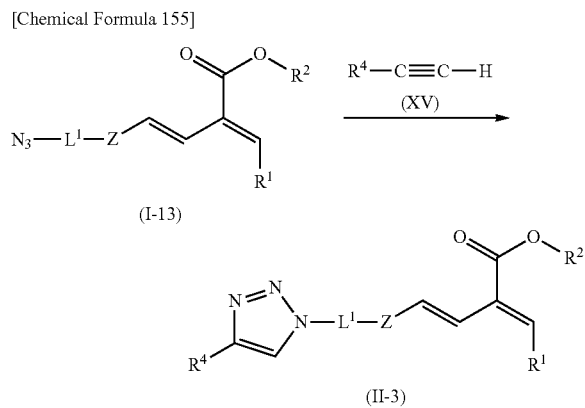

In Formula (I-13) above, $R^1$ is a group represented by —$CH_2$—$OR^{11}$, $R^2$ is a hydrogen atom, a lower alkyl group, a lower alkyl group substituted with one or more substituents, an ar(lower) alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, and Z is a group represented by the formula below:

[Chemical Formula 156]

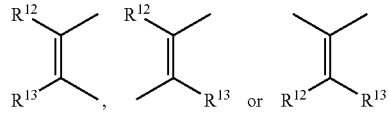

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

Moreover, in Formula (XV) above, $R^4$ is a carbonyl group substituted with a substituent that functions as a label.

Moreover, in Formula (II-3) above, $R^1$ is a group represented by —$CH_2$—$OR^{11}$, $R^2$ is a hydrogen atom, a lower alkyl group, a lower alkyl group substituted with one or more substituents, an ar(lower) alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label, and Z is a group represented by the formula below:

[Chemical Formula 157]

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

For example, by coupling an azide compound represented by Formula (I-13) with an acetylene compound represented by Formula (XV), a compound represented by Formula (II-3) can be obtained. The compound represented by Formula (II-3) corresponds to a compound represented by Formula (II) wherein $R^1$ is a group represented by —$CH_2$—$OR^{11}$ and $X^1$ is:

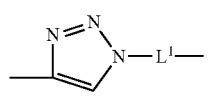

[Chemical Formula 158]

The aforementioned coupling preferably is carried out (Condition a) in the presence of CuI, diisopropylethylamine and 2,6-lutidine, or (Condition b) in the presence of $CuSO_4$ and sodium ascorbate. The coupling reaction can be performed at, for example, 10 to 200° C. and preferably 25 to 60° C. The coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Moreover, the compound represented by Formula (II) wherein $R^1$ is a group represented by —$CH_2$—$OR^{11}$ and $X^1$ is:

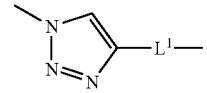

[Chemical Formula 159]

can be produced according to, for example, the following method.

Scheme 4

[Chemical Formula 160]

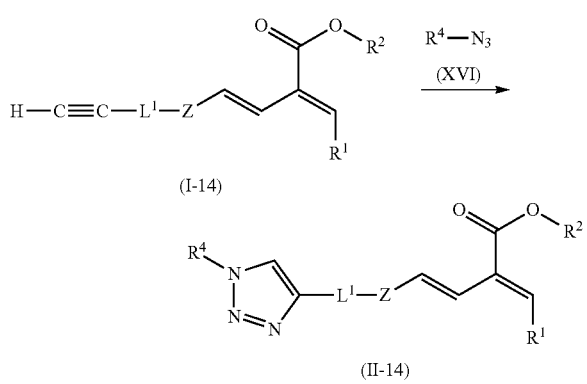

In Formula (I-14) above, $R^1$ is a group represented by —$CH_2$—$OR^{11}$, $R^2$ is a hydrogen atom, a lower alkyl group, a lower alkyl group substituted with one or more substituents, an ar(lower) alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, and Z is a group represented by the formula below:

[Chemical Formula 161]

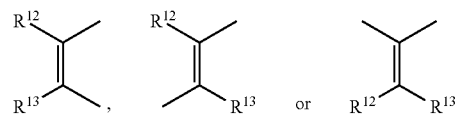

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $L^2$ is a bond or a group represented by —$(CH_2)_n$—O—$(CH_2)_m$— (wherein n and m each independently represent an integer of 1 to 20), $M^2$ is a hydrogen atom or a protecting group for a group represented by —OH, —$CO_2H$, —SH or —$NH_2$, $A^2$ is a group represented by —O—, —$CO_2$—, —S— or —NH—, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

Moreover, in Formula (XV), $R^4$ is a carbonyl group substituted with a substituent that functions as a label.

Moreover, in Formula (II-4),
$R^1$ is a group represented by $—CH_2—OR^{11}$,
$R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula $-L^2-A^2-M^2$,
$R^4$ is a carbonyl group substituted with a substituent that functions as a label, and
Z is a group represented by the formula below:

[Chemical Formula 162]

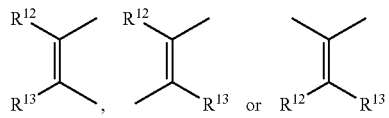

or a divalent group derived from an aromatic hydrocarbon or a divalent group derived from an aromatic hydrocarbon substituted with one or more substituents.

In the formulae above,
$L^1$ is a bond or a group represented by the formula $—(CH_2)_n—$, the formula $—(CH_2)_n—O—(CH_2)_m—$, the formula $—(CH_2)_n—CONH—$ or the formula $—CONH—(CH_2)_n—$ (wherein n and m each independently represent an integer of 1 to 20),
$L^2$ is a bond or a group represented by $—(CH_2)_n—O—(CH_2)_m—$ (wherein n and m each independently represent an integer of 1 to 20),
$A^2$ is a group represented by $—O—$, $—CO_2—$, $—S—$ or $—NH—$,
$M^2$ is a hydrogen atom or a protecting group for a group represented by $—OH$, $—CO_2H$, $—SH$ or $—NH_2$,
$R^{11}$ is a protecting group for a hydroxyl group,
$R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, a lower ar(lower)alkoxy group, an aryl group, a lower aryl group, a heteroaryl group or a lower heteroaryl group, and
$R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

For example, by coupling an azide compound represented by Formula (I-14) with an acetylene compound represented by Formula (XV), a compound represented by Formula (II-4) can be obtained. The compound represented by Formula (II-4) corresponds to a compound represented by Formula (II) wherein $R^1$ is a group represented by $—CH_2—OR^{11}$ and $X^1$ is:

[Chemical Formula 163]

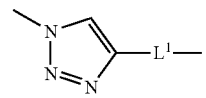

The aforementioned coupling preferably is carried out (Condition a) in the presence of CuI, diisopropylethylamine and 2,6-lutidine, or (Condition b) in the presence of $CuSO_4$ and sodium ascorbate. The coupling reaction can be performed at, for example, 10 to 200° C. and preferably 25 to 60° C. The coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Moreover, the compound represented by Formula (II) wherein $R^1$ is a group represented by $—CH_2OH$ or $—CHO$ can be produced according to, for example, the following scheme.

Scheme 5

[Chemical Formula 164]

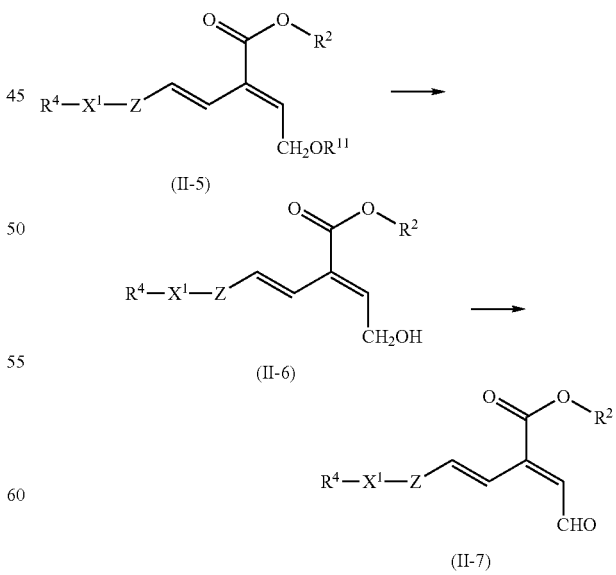

By removing $R^{11}$ in a compound represented by Formula (II-5), a compound represented by Formula (II-6) can be obtained. The compound represented by Formula (II-6) is a compound represented by Formula (II) wherein $R^1$ is a group represented by —$CH_2OH$. Since $R^{11}$ is a protecting group for a hydroxyl group, $R^{11}$ can be removed by treating it under suitable conditions according to the type of protecting group. For example, when $R^{11}$ is tetrahydro-2H-pyran-2-yl (THP), examples of such suitable conditions include treatment with acidic water, acid treatment with toluenesulfonic acid (p-TsOH), acid treatment with pyridinium paratoluene sulfonate (PPTS), and the like.

Next, by oxidizing the compound represented by Formula (II-6), a compound represented by Formula (II-7) can be obtained. The compound represented by Formula (II-7) is a compound represented by Formula (II) above wherein $R^1$ is a group represented by —CHO. The oxidation conditions are not limited insofar as the conditions allow a primary alcohol to be oxidized to an aldehyde. The oxidation conditions involve, for example, pyridinium dichlorochromate (PDC), a Dess-Martin reagent, manganese dioxide, tetrapropylammonium perruthenate (TPAP) oxidation, Ishii oxidation, Swern oxidation, Corey-Kim oxidation, natural oxidation, enzymatic oxidation, $PtO_2$ oxidation, etc. The oxidation reaction can be performed at, for example, 10 to 100° C. and preferably 25 to 50° C. The oxidation reaction can be carried out in a nonpolar solvent such as tetrahydrofuran, ether, benzene, toluene or xylene as well as in a polar solvent such as dimethylformamide (DMF), dimethylsulfoxide (DMSO), acetonitrile, propionitrile or diethoxyethane (DME).

The compound represented by Formula (XVI), the compound represented by Formula (XV) and the compound represented by Formula (XVI) may be obtained commercially or may be produced according to published literature.

Production Method 3

The compound represented by Formula (III) wherein $R^1$ is a group represented by —$CH_2OR^{11}$ can be produced according to, for example, the following scheme.

Scheme 6

[Chemical Formula 165]

In Formula (I-21) above,
$R^1$ is a group represented by —$CH_2$—$OR^{11}$,
$R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH, and   [Chemical Formula 166]

Z is a group represented by the formula below:

[Chemical Formula 167]

or a divalent group derived from an aromatic hydrocarbon or a divalent group derived from an aromatic hydrocarbon substituted with one or more substituents.

In the formulae above,
$L^1$ is a bond or a group represented by the formula —$(CH_2)_n$—O—$(CH_2)_3$—, the formula —$(CH_2)_n$—O—$(CH_2)_m$—, the formula —$(CH_2)_n$—CONH— or the formula —CONH—
$(CH_2)_n$— (wherein n and m each independently represent an integer of 1 to 20),
$A^1$ is a group represented by —O—, —$CO_2$—, —S— or —NH—,
$L^1$ is a bond or a group represented by —$(CH_2)_n$—O—$(CH_2)_m$— (wherein n and m each independently represent an integer of 1 to 20),
$A^2$ is a group represented by —O—, —$CO_2$—, —S— or —NH—,
$M^1$ is a hydrogen atom, a group represented by —OH, —$CO_2H$, —SH or —$NH_2$, or a protecting group for a group represented by —OH, —$CO_2H$, —SH or —$NH_2$,
$R^{11}$ is a protecting group for a hydroxyl group,
$R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and
$R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, in Formula (XVII),
$R^5$ is a carbonyl group substituted with a substituent that functions as a label,
$L^3$ is a bond or a group represented by the formula —$(CH_2)_n$— or —$(CH_2)_n$—O—$(CH_2)_m$— (wherein n and m each independently represent an integer of 1 to 20), and
$Y^2$ is a leaving group.

Moreover, in Formula (III-11),
$R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^1$-$A^1$-$M^1$, the formula -$L^1$-$N_3$ or the formula:

-$L^1$-C≡CH,   [Chemical Formula 168]

$R^5$ is a carbonyl group substituted with a substituent that functions as a label, and Z is a group represented by:

[Chemical Formula 169]

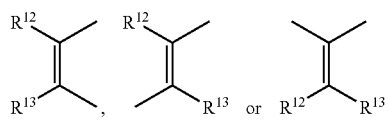

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20), $M^1$ is a hydrogen atom, a group represented by —OH, —$CO_2H$, —SH or —$NH_2$, or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Specifically, by coupling a compound represented by Formula (I-21) with a compound represented by Formula (XVII) to eliminate a compound represented by the formula $Y^2$—H, a compound represented by Formula (III-11) can be obtained. The compound represented by Formula (III-11) is a compound represented by Formula (III) wherein $R^1$ is a group represented by —$CH_2OR^{11}$. Moreover, in Formula (III-11) above, $X^2$ refers to the formula -$L^2$-$A^2$-$L^3$-. The coupling reaction can be performed at, for example, 10 to 60° C. and preferably 25 to 40° C. The coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Moreover, the compound represented by Formula (III) wherein $R^1$ is a group represented by —$CH_2OH$ or —CHO can be produced according to, for example, the following scheme.

Scheme 5

[Chemical Formula 170]

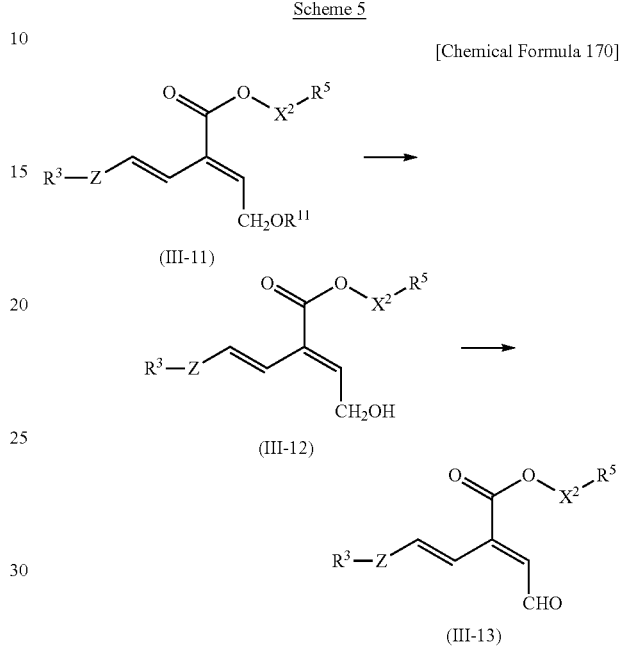

By removing $R^{11}$ in the compound represented by Formula (III-11), a compound represented by Formula (III-12) can be obtained. The compound represented by Formula (III-12) is a compound represented by Formula (III) wherein $R^1$ is a group represented by —$CH_2OH$. Since $R^{11}$ is a protecting group for a hydroxyl group, $R^{11}$ can be removed by treating it under suitable conditions according to the type of protecting group. For example, when $R^{11}$ is tetrahydro-2H-pyran-2-yl (THP), examples of such suitable conditions include treatment with acidic water, acid treatment with p-toluenesulfonic acid (p-TsOH), acid treatment with pyridinium paratoluene sulfonate (PPTS), and the like.

Next, by oxidizing the compound represented by Formula (III-12), a compound represented by Formula (III-13) can be obtained. The compound represented by Formula (III-13) is a compound represented by Formula (III) wherein $R^1$ is a group represented by —CHO. The oxidation conditions are not limited insofar as the conditions for oxidizing a primary alcohol to an aldehyde. The oxidation conditions involve, for example, pyridinium dichlorochromate (PDC), a Dess-Martin reagent, manganese dioxide, tetrapropylammonium perruthenate (TPAP) oxidation, Ishii oxidation, Swern oxidation, Corey-Kim oxidation, natural oxidation, enzymatic oxidation, $PtO_2$ oxidation, etc. The oxidation reaction can be performed at, for example, 10 to 100° C. and preferably 25 to 50° C. The oxidation reaction can be carried out in a nonpolar solvent such as tetrahydrofuran, ether, benzene, toluene or xylene as well as in a polar solvent such as dimethylformamide (DMF), dimethylsulfoxide (DMSO), acetonitrile, propionitrile or diethoxyethane (DME).

The compound represented by Formula (XVII) may be obtained commercially or may be produced according to published literature.

Production Method 4

The compound represented by Formula (IV) can be produced according to, for example, the following method or the like. First, the compound represented by Formula (IV) wherein $R^1$ is a group represented by $-CH_2-OR^{11}$ can be produced according to, for example, the following scheme.

Scheme 6

[Chemical Formula 171]

(II-11) + (XVII) → (IV-1)

In Formula (II-11) above, $R^1$ is a group represented by $-CH_2-OR^{11}$, $R^4$ is a carbonyl group substituted with a substituent that functions as a label, $X^1$ is a group represented by the formula $-L^1-A^1-$, the formula $-A^1-L^1-$ or the formula below:

[Chemical Formula 172]

and Z is a group represented by the formula below:

[Chemical Formula 173]

or a divalent group derived from an aromatic hydrocarbon or a divalent group derived from an aromatic hydrocarbon substituted with one or more substituents.

In the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-(CH_2)_n-$ (wherein n and m each independently represent an integer of 1 to 20), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20), $A^2$ is a group represented by $-O-$, $-CO_2-$, $-S-$ or $-NH-$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, in Formula (XVII) above, $R^5$ is a carbonyl group substituted with a substituent that functions as a label, $L^3$ is a bond or a group represented by the formula $-(CH_2)_n-$ or $-(CH_2)_n-O-(CH_2)_m-$ (wherein n and m each independently represent an integer of 1 to 20), and $Y^2$ is a leaving group.

Moreover, in Formula (IV-1), $R^4$ is a carbonyl group substituted with a substituent that functions as a label, $R^5$ is a carbonyl group substituted with a substituent that functions as a label, $X^1$ is a group represented by the formula $-L^1-A^1-$, the formula $-A^1-L^1-$ or the formula below:

[Chemical Formula 174]

and Z is a group represented by the formula below:

[Chemical Formula 175]

or a divalent group derived from an aromatic hydrocarbon or a divalent group derived from an aromatic hydrocarbon substituted with one or more substituents.

In the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-(CH_2)_n-$ (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Specifically, by coupling a compound represented by Formula (II-11) with a compound represented by Formula (XVII) to eliminate a compound represented by the formula $Y^2$—H, a compound represented by Formula (IV-1) can be obtained. The compound represented by Formula (IV-1) is a compound represented by Formula (V) wherein $R^1$ is a group represented by —$CH_2OR^{11}$. In addition, $X^2$ in Formula (IV-1) above refers to the formula -$L^2$-$A^2$-$L^3$-. The coupling reaction can be performed at, for example, 10 to 60° C. and preferably 25 to 40° C. The coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Moreover, the compound represented by Formula (IV) wherein $R^1$ is a group represented by —$CH_2$—$OR^{11}$ and $X^1$ is a group represented by the formula -$A^1$-$L^1$- or -$L^1$-$A^1$- can be produced according to, for example, the following scheme.

Scheme 7

[Chemical Formula 176]

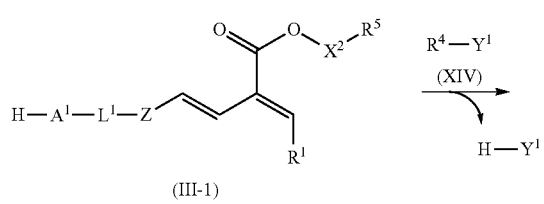

(III-1)

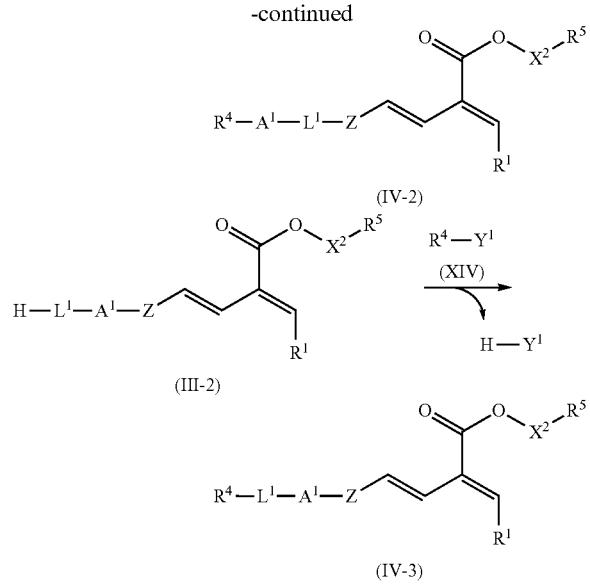

In Formula (III-1) and Formula (III-2) above,
$R^1$ is a group represented by —$CH_2$—$OR^{11}$,
$R^5$ is a carbonyl group substituted with a substituent that functions as a label,
$X^2$ is a group represented by the formula -$L^2$-$A^2$-$L^3$-, and
Z is a group represented by:

[Chemical Formula 177]

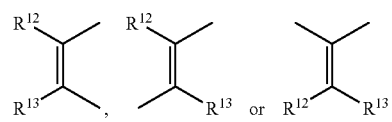

or a divalent group derived from an aromatic hydrocarbon or a divalent group derived from an aromatic hydrocarbon substituted with one or more substituents.

In the formulae above,
$L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Moreover, in Formula (V above, $R^4$ is a carbonyl group substituted with a substituent that functions as a label and $Y^1$ is a leaving group.

Moreover, in Formula (IV-2) and Formula (IV-3) above, $R^1$ is a group represented by —$CH_2$—$OR^{11}$, $R^4$ is a carbonyl group substituted with a substituent that functions as a label, $R^5$ is a carbonyl group substituted with a substituent that functions as a label, $X^2$ is a group represented by the formula -$L^2$-$A^2$-$L^3$-, and Z is a group represented by the formula below:

[Chemical Formula 178]

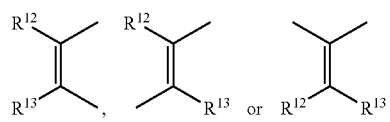

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

Specifically, for example, by coupling a compound represented by Formula (III-1) with a compound represented by Formula (XIV) eliminate a compound represented by the formula $Y^1$—H, a compound represented by Formula (IV-2) can be obtained. Alternatively, by coupling a compound represented by Formula (III-2) with a compound represented by Formula (XIV) to eliminate a compound represented by the formula $Y^1$—H, a compound represented by Formula (IV-3) can be obtained. The coupling reaction can be performed at, for example, 10 to 60° C. and preferably 25 to 40° C. The coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Moreover, the compound represented by Formula (IV) wherein $R^1$ is a group represented by —$CH_2$—$OR^{11}$ and $X^1$ is:

[Chemical Formula 179]

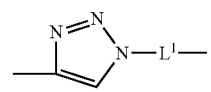

can be produced according to, for example, the following scheme.

Scheme 8

[Chemical Formula 180]

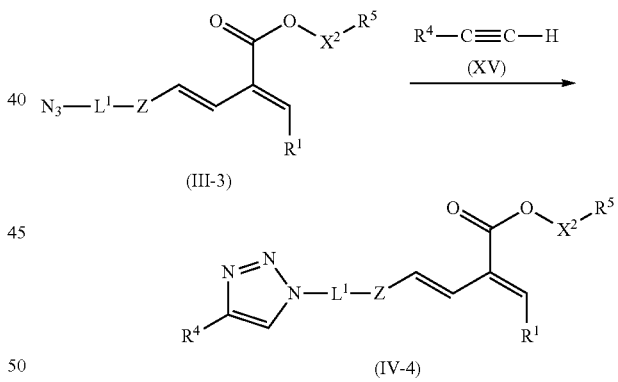

In Formula (III-3) above, $R^1$ is a group represented by —$CH_2$—$OR^{11}$, $R^5$ is a carbonyl group substituted with a substituent that functions as a label, $X^2$ is a group represented by the formula -$L^2$-$A^2$-$L^3$-, and Z is a group represented by:

[Chemical Formula 181]

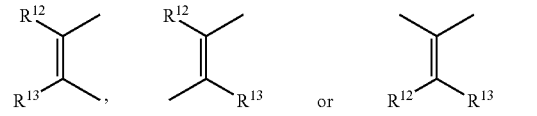

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

In Formula (XV) above, $R^4$ is a carbonyl group substituted with a substituent that functions as a label.

In Formula (IV-4) above, $R^1$ is a group represented by —$CH_2$—$OR^{11}$, $R^4$ is a carbonyl group substituted with a substituent that functions as a label, $R^5$ is a carbonyl group substituted with a substituent that functions as a label, $X^2$ is a group represented by the formula -$L^2$-$A^2$-$L^3$-, and Z is a group represented by the formula below:

[Chemical Formula 182]

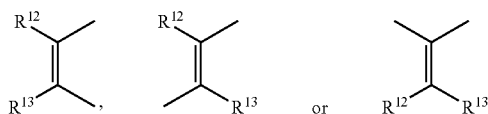

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20), $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

For example, by coupling an azide compound represented by Formula (III-3) with an acetylene compound represented by Formula (XV), a compound represented by Formula (IV-4) can be obtained. The compound represented by Formula (IV-4) corresponds to a compound represented by Formula (IV) wherein $R^1$ is a group represented by —$CH_2$—$OR^{11}$ and $X^1$ is:

[Chemical Formula 183]

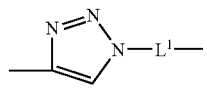

The aforementioned coupling preferably is carried out (Condition a) in the presence of CuI, diisopropylethylamine and 2,6-lutidine, or (Condition b) in the presence of $CuSO_4$ and sodium ascorbate. The coupling reaction can be performed at, for example, 10 to 200° C. and preferably 25 to 60° C. The coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Alternatively, the compound represented by Formula (IV) wherein $R^1$ is a group represented by —$CH_2$—$OR^{11}$ and $X^1$ is:

[Chemical Formula 184]

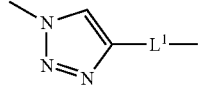

can be produced according to the following scheme.

Scheme 9

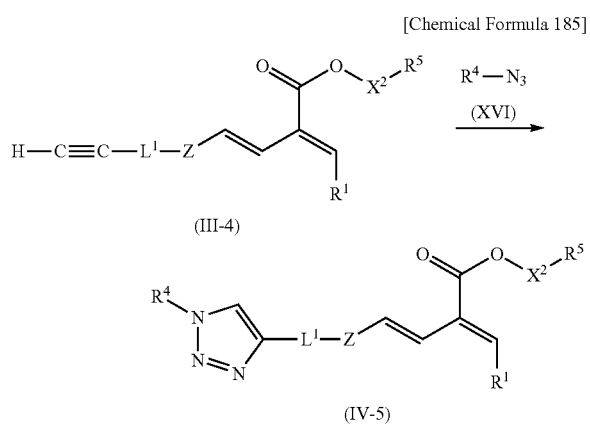

In Formula (III-4) above,
$R^1$ is a group represented by —$CH_2$—$OR^{11}$,
$R^5$ is a carbonyl group substituted with a substituent that functions as a label
$X^2$ is a group represented by the formula -$L^2$-$A^2$-$L^3$-, and
Z is a group represented by:

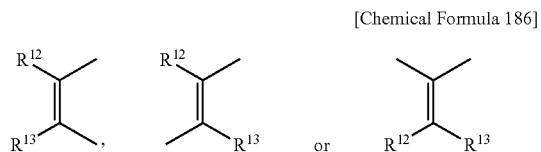

or a divalent group derived from an aromatic hydrocarbon or a divalent group derived from an aromatic hydrocarbon substituted with one or more substituents.

In the formulae above,
$L^1$ is a bond or a group represented by the formula qj—$(CH_2)_n$—, the formula —$(CH_2)$—O—$(CH_2)_m$—, the formula —$(CH_2)_n$—CONH— or the formula —CONH—$(CH_2)_n$— (wherein n and m each independently represent an integer of 1 to 20),
$L^2$ is a bond or a group represented by —$(CH_2)_n$—O—$(CH_2)_m$—(wherein n and m each independently represent an integer of 1 to 20),
$A^2$ is a group represented by —O—, —$CO_2$—, —S— or —NH—,
$L^3$ is a bond or a group represented by the formula —$(CH_2)_n$— or —$(CH_2)_n$—O—$(CH_2)_m$— (wherein n and m each independently represent an integer of 1 to 20),
$R^{11}$ is a protecting group for a hydroxyl group,
$R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and
$R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

In Formula (XVI) above, $R^4$ is a carbonyl group substituted with a substituent that functions as a label.

In Formula (IV-5) above,
$R^1$ is a group represented by —$CH_2$—$OR^{11}$,
$R^4$ is a carbonyl group substituted with a substituent that functions as a label,
$R^5$ is a carbonyl group substituted with a substituent that functions as a label,
$X^2$ is a group represented by the formula -$L^2$-$A^2$-$L^3$-, and
Z is a group represented by the formula below:

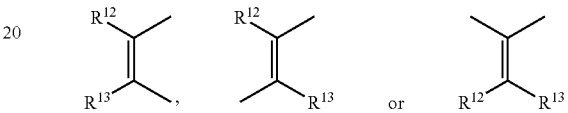

or a divalent group derived from an aromatic hydrocarbon or a divalent group derived from an aromatic hydrocarbon substituted with one or more substituents.

In the formulae above,
$L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20),
$L^2$ is a bond or a group represented by —$(CH_2)_n$—O—$(CH_2)_m$— (wherein n and m each independently represent an integer of 1 to 20),
$A^2$ is a group represented by —O—, —$CO_2$—, —S— or —NH—,
$L^3$ is a bond or a group represented by the formula —$(CH_2)_n$— or —$(CH_2)_n$—O—$(CH_2)_m$— (wherein n and m each independently represent an integer of 1 to 20),
$R^{11}$ is a protecting group for a hydroxyl group,
$R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents, and
$R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower) alkoxy group, an ar(lower)alkoxy group substituted with one or more substituents, an aryl group, an aryl group substituted with one or more substituents, a heteroaryl group or a heteroaryl group substituted with one or more substituents.

For example, by coupling an azide compound represented by Formula (III-4) with an acetylene compound represented by Formula XVI), a compound represented by Formula (IV-5) can be obtained. The compound represented by Formula (IV-5) corresponds to a compound represented by Formula (IV) wherein $R^1$ is a group represented by —$CH_2$—$OR^{11}$ and $X^1$ is:

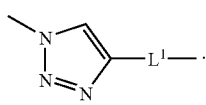

[Chemical Formula 188]

The aforementioned coupling preferably is carried out (Condition a) in the presence of CuI, diisopropylethylamine and 2,6-lutidine, or (Condition b) in the presence of $CuSO_4$ and sodium ascorbate. The coupling reaction can be performed at, for example, 10 to 200° C. and preferably 25 to 60° C. The coupling reaction can be performed in a nonpolar solvent such as tetrahydrofuran, ether, benzene or toluene as well as in a polar solvent such as dimethylformamide (DMF), dimethyl sulfoxide (DMSO), acetonitrile, propionitrile or diethoxyethane (DME).

Moreover, the compound represented by Formula (C wherein $R^1$ is a group represented by —$CH_2OH$ or —CHO can be produced according to, for example, the following scheme.

Scheme 10

[Chemical Formula 189]

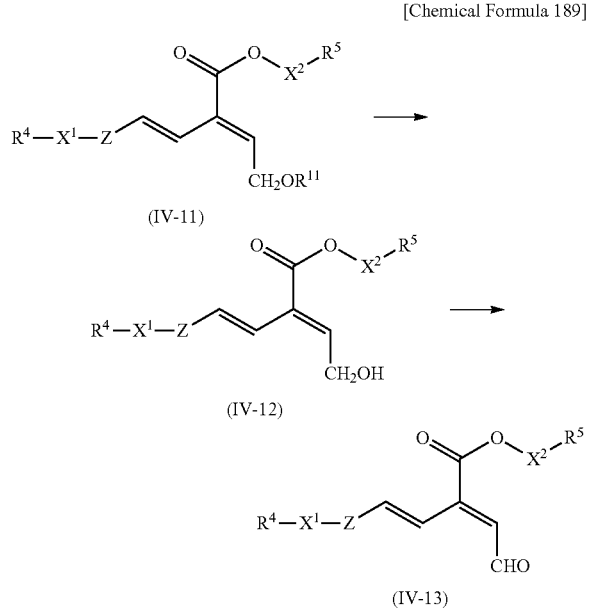

By removing $R^{11}$ in a compound represented by Formula (IV-11), a compound represented by Formula (IV-12) can be obtained. The compound represented by Formula (IV-11) is a compound represented by Formula (IV) wherein $R^1$ is a group represented by —$CH_2OH$. Since $R^{11}$ is a protecting group for a hydroxyl group, $R^{11}$ can be removed by treating it under suitable conditions according to the type of protecting group. For example, when $R^{11}$ is tetrahydro-2H-pyran-2-yl (THP), examples of such suitable conditions include treatment with acidic water, acid treatment with p-toluenesulfonic acid (p-TsOH), acid treatment with pyridinium paratoluene sulfinate (PPTS), and the like.

Next, by oxidizing the compound represented by Formula (IV-12), a compound represented by Formula (IV-13) can be obtained. The compound represented by Formula (IV-13) is a compound represented by Formula (IV) wherein $R^1$ is a group represented by —CHO. The oxidation conditions are not limited insofar as the conditions allow a primary alcohol to be oxidized to an aldehyde. The oxidation conditions involve, for example, pyridinium dichlorochromate (PDC), a Dess-Martin reagent, manganese dioxide, tetrapropylammonium perruthenate (TPAP) oxidation, Ishii oxidation, Swern oxidation, Corey-Kim oxidation, natural oxidation, enzymatic oxidation, $PtO_2$ oxidation, etc. The oxidation reaction can be performed at, for example, 10 to 100° C. and preferably 25 to 50° C. The oxidation reaction can be carried out in a nonpolar solvent such as tetrahydrofuran, ether, benzene, toluene or xylene as well as in a polar solvent such as dimethylformamide (DMF), dimethylsulfoxide (DMSO), acetonitrile, propionitrile or diethoxyethane (DME).

The compound represented by Formula (XVII), the compound represented by Formula (XIV), the compound represented by Formula (XV) and the compound represented by Formula (XVI) may be obtained commercially or may be produced according to published literature.

In the respective steps of Schemes 1 to 10, a protecting group may be introduced into each functional group, a protecting group may be removed, and a different protecting group may be used as necessary. Selection of a protecting group, introduction of a protecting group and removal of a protecting group according to the type of functional group may be performed according to a method known in this technical field, and reference may be made to, for example, "*Protective Groups in Organic Synthesis*", T. Greene et al., published by John Wiley & Sons, Inc., and the like.

Moreover, the present invention is directed to a method for labeling a compound containing an amino group. This method includes the step of reacting one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO with an amino group-containing compound to label the amino group-containing compound with the one or more hexatriene-β-carbonyl compounds.

The labeling method can be performed by, for example, admixing the one or more hexatriene-β-carbonyl compounds and the amino group-containing compound in a solution (such as water, a buffer solution) at, for example, room temperature to react the one or more hexatriene-β-carbonyl compounds and the amino group-containing compound, thereby labeling the amino group-containing compound with the one or more hexatriene-β-carbonyl compounds.

In the labeling method, the amino group in the amino group-containing compound is preferably an amino group of an amino acid residue and more preferably of a lysine residue.

Moreover, the present invention is directed to a test composition as described above. The test composition contains one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO. The test composition is not limited insofar as it contains the one or more hexatriene-β-carbonyl compounds, and further may contain, for example, another organic compound (such as a low-molecular ligand), protein, peptide, DNA, etc.

It is preferable that the test composition is for use in a test carried out via positron emission tomography, fluorescent imaging, nuclear magnetic resonance imaging (MRI), single-photon emission computed tomography (SPECT) or autoradiography because such tests allow an amino group in a molecule, such as a biopolymer, to be labeled readily and promptly and are thus suitable for imaging.

Moreover, the present invention is directed to a method for measuring the distribution of an amino group-containing compound in a living body. This measurement method includes the steps of:

administering into a living body one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO to incorporate the one or more hexatriene-β-carbonyl compounds into the living body, labeling in the living body an amino group-containing compound that is present in the living body with the one or more hexatriene-β-carbonyl compounds, and measuring the distribution of the amino group-containing compound in the living body by detecting the labeled amino group-containing compound through a substituent that is present in the one or more hexatriene-β-carbonyl compounds and that functions as a label.

In the measurement method, both oral administration and parenteral administration may be performed for the administration of one or more hexatriene-β-carbonyl compounds into a living body. In the case of oral administration, the one or more hexatriene-β-carbonyl compounds can be administered using, for example, a gastric tube (oral tube) or a nasotracheal tube. Alternatively, the aforementioned compounds can be administered after being admixed with food or drinking water. In the case of parenteral administration, the one or more hexatriene-β-carbonyl compounds can be administered via, for example, intraperitoneal administration, intravenous injection, etc. In addition, the aforementioned compounds can be administered through caudal vein injection for small animals such as mice and rats.

The dosage of the one or more hexatriene-β-carbonyl compounds is, for example, 1 mg/kg to 100 mg/kg relative to the weight of a living body on which administration is performed, preferably 1 mg/kg to 50 mg/kg, and more preferably 1 mg/kg to 20 mg/kg.

In the measurement method, the amino group in the amino group-containing compound is an amino group of preferably an amino acid residue and more preferably of a lysine residue.

In the measurement method, the detection of the substituent that functions as a label preferably is performed by positron emission tomography, fluorescent imaging, nuclear magnetic resonance imaging (MRI), single-photon emission computed tomography (SPECT) or autoradiography.

Moreover, the present invention is directed to, as described above, a test kit that contains one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO. This kit labels an amino-group containing compound present in a sample with the one or more hexatriene-β-carbonyl compounds, allowing the amino group-containing compound to be examined. The test kit is not limited insofar as it contains the one or more hexatriene-β-carbonyl compounds, and further may contain, for example, another organic compound (such as a low-molecular ligand), protein, peptide, DNA, etc.

Moreover, the present invention is directed to a method for producing a PET contrast agent containing an antibody labeled with one or more hexatriene-β-carbonyl compounds into which a positron-emitting metal radionuclide is incorporated. The production method includes the steps of:

providing one or more hexatriene-β-carbonyl compounds selected from the group consisting of a compound represented by Formula (II) wherein $R^1$ is a group represented by —CHO and $R^4$ is a carbonyl group substituted with a substituent that functions as a label the carbonyl group substituted with a substituent that functions as a label being able to coordinate with a radioactive metal, a compound represented by Formula (III) wherein $R^1$ is a group represented by —CHO and $R^5$ is a carbonyl group substituted with a substituent that functions as a label, the carbonyl group substituted with a substituent that functions as a label being able to coordinate with a radioactive metal and a compound represented by Formula (IV) wherein $R^1$ is a group represented by —CHO and at least one of $R^4$ and $R^5$ is a carbonyl group substituted with a substituent that functions as a label, the carbonyl group substituted with a substituent that functions as a label being able to coordinate with a radioactive metal, a positron-emitting metal radionuclide, and
an antibody;

incorporating the positron-emitting nuclide into the one or more hexatriene-β-carbonyl compounds; and reacting the antibody with the one or more hexatriene-β-carbonyl compounds into which the positron-emitting nuclide is incorporated to give an antibody labeled with the one or more hexatriene-β-carbonyl compounds into which the positron-emitting nuclide is incorporated.

In the method for producing a PET contrast agent, examples of the positron-emitting nuclide include $^{68}$Ga, $^{64}$Cu, $^{52}$Fe, $^{55}$Co, $^{61}$Cu, $^{62}$Cu, $^{63}$Zn, $^{82}$Rb, $^{86}$Y, $^{89}$Zr, $^{110}$In, etc. Such positron-emitting nuclides may exist in the form of a salt, and examples include $^{68}$GaCl$_3$, $^{52}$FeCl$_3$, $^{55}$CoCl$_3$, $^{61}$CuCl$_3$, $^{62}$CuCl$_3$, $^{63}$ZnCl$_3$, $^{82}$RbCl$_3$, $^{86}$YCl$_3$, $^{89}$ZrCl$_3$, $^{110}$InCl$_3$, etc.

In the method for producing a PET contrast agent, the antibody is not limited, and examples include an anti-HER2 (human epidermal growth factor receptor 2) protein antibody, an anti-carcarcinoembryonic antigen (CEA) antibody, an anti-celladhesion molecule (CAM) antibody, an anti-EGFR (epidermal growth factor receptor), etc.

In the method for producing a PET contrast agent, the step of incorporating the positron-emitting nuclide into the one or more hexatriene-β-carbonyl compounds can be carried out by admixing the one or more hexatriene-β-carbonyl compounds, the positron-emitting nuclide and the antibody, for example, in a solution (such as water, a buffer solution) at, for example, room temperature to react the one or more hexatriene-β-carbonyl compounds and the positron-emitting nuclide, thereby incorporating the positron-emitting nuclide into the one or more hexatriene-β-carbonyl compounds.

In the method for producing a PET contrast agent, the step of reacting the antibody with the one or more hexatriene-β-carbonyl compounds into which the positron-emitting nuclide is incorporated to give an antibody labeled with the one or more hexatriene-β-carbonyl compounds into which the positron-emitting nuclide is incorporated can be carried out by admixing the one or more hexatriene-β-carbonyl compounds and the antibody, for example, in a solution (such as water, a buffer solution) at, for example, room temperature to capture the antibody with the one or more hexatriene-β-carbonyl compounds, thereby enabling the antibody to be labeled. The antibody is preferably an amino group-containing antibody and more preferably an antibody that contains an amino group of a lysine residue. This is because, when the antibody is an amino group-containing antibody, it reacts with the group represented by —CHO of the one or more hexatriene-β-carbonyl compounds, thereby allowing the amino group to be captured promptly in a good yield.

Moreover, the present invention is directed to, as described above, an antibody labeled with one or more hexatriene-β-carbonyl compounds into which a positron-emitting metal radionuclide is incorporated. The antibody is characterized in that the one or more hexatriene-β-carbonyl compounds are one or more hexatriene-β-carbonyl compounds selected from the group consisting of a compound represented by Formula (II) wherein $R^1$ is a group represented by —CHO and $R^4$ is a carbonyl group substituted with a substituent that functions as a label the carbonyl group substituted with a substituent that functions as a label being able to coordinate with a radioactive metal; a compound represented by Formula (IV) wherein $R^1$ is a group represented by —CHO and $R^5$ is a carbonyl group substituted with a substituent that functions as a label the carbonyl group substituted with a substituent that functions as a label being able to coordinate with a radioactive metal; and a the compound represented by Formula (IV) wherein $R^1$ is a group represented by —CHO and at least one of $R^4$ and $R^5$ is a carbonyl group substituted with a substituent that functions as a label the carbonyl group substituted with a substituent that functions as a label being able to coordinate with a radioactive metal.

In the labeled antibody, examples of the positron-emitting nuclide include $^{68}$Ga, $^{64}$Cu, $^{52}$Fe, $^{55}$Co, $^{61}$Cu, $^{62}$Cu, $^{63}$Zn, $^{82}$Rb, $^{86}$Y, $^{89}$Zr, $^{110}$In, etc.

In the labeled antibody, the antibody is not limited, and examples include an anti-HER2 (human epidermal growth factor receptor 2) protein antibody, an anti-carcarcinoembryonic antigen (CEA) antibody, an anti-celladhesion molecule (CAM) antibody, anti-EGFR (epidermal growth factor receptor), etc.

Moreover, the present invention is directed to, as described above, a kit for producing a PET contrast agent that contains an antibody labeled with one or more hexatriene-β-carbonyl compounds into which a positron-emitting metal radionuclide is incorporated. The kit contains:

one or more hexatriene-β-carbonyl compounds selected from the group consisting of a compound represented by Formula (II) wherein $R^4$ is a carbonyl group substituted with a substituent that functions as a label the carbonyl group substituted with a substituent that functions as a label being able to coordinate with a radioactive metal a compound represented by Formula (III) wherein $R^5$ is a carbonyl group substituted with a substituent that functions as a label the carbonyl group substituted with a substituent that functions as a label being able to coordinate with a radioactive metal and a compound represented by Formula (IV) wherein at least one of $R^4$ and $R^5$ is a carbonyl group substituted with a substituent that functions as a label the carbonyl group substituted with a substituent that functions as a label being able to coordinate with a radioactive metal;

an antibody to be labeled; and optionally an instruction.

In the production kit, the antibody is not limited, and examples include an anti-HER2 (human epidermal growth factor receptor 2) protein antibody, an anti-carcarcinoembryonic antigen (CEA) antibody, an anti-celladhesion molecule (CAM) antibody, anti-EGFR (epidermal growth factor receptor), etc.

The production kit is not limited insofar as it contains the one or more hexatriene-β-carbonyl compounds and the antibody to be labeled, and further may contain, for example, another organic compound (such as a low-molecular ligand), protein, peptide, sugar chain, etc.

Moreover, the present invention is directed to a method for producing an antibody labeled with one or more hexatriene-β-carbonyl compounds. The production method includes the steps of:

providing one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO, and an antibody; and reacting the one or more hexatriene-β-carbonyl compounds with the antibody to label the antibody with one or more hexatriene-β-carbonyl compounds.

In the method for producing a labeled antibody, the antibody is not limited, and examples include an anti-HER2 (human epidermal growth factor receptor 2) protein antibody, an anti-carcarcinoembryonic antigen (CEA) antibody, an anti-celladhesion molecule (CAM) antibody, anti-EGFR (epidermal growth factor receptor), etc. The antibody is preferably an amino group-containing antibody and more preferably an antibody that contains an amino group of a lysine residue. This is because, when the antibody is an amino group-containing antibody, it reacts with the group represented by —CHO of the one or more hexatriene-β-carbonyl compounds, thereby allowing the amino group to be captured promptly in a good yield.

In the method for producing a labeled antibody, the step of reacting the antibody with the one or more hexatriene-β-carbonyl compounds can be carried out by admixing the one or more hexatriene-β-carbonyl compounds and the antibody, for example, in a solution (such as water, a buffer solution) at, for example, room temperature, thereby reacting the antibody with the one or more hexatriene-β-carbonyl compounds.

In the method for producing a labeled antibody, the antibody is preferably an amino group-containing antibody and more preferably an antibody that contains an amino group of a lysine residue. This is because, when the antibody is an amino group-containing antibody, it reacts with the group represented by —CHO of the one or more hexatriene-β-carbonyl compounds, thereby allowing the amino group to be captured promptly in a good yield.

Moreover, the present invention is directed to, as described above, an antibody labeled with one or more hexatriene-β-carbonyl compounds. The antibody is characterized in that the one or more hexatriene-β-carbonyl compounds are hexatriene-β-carbonyl compounds selected from the group consisting of a compound represented by Formula (II) wherein $R^1$ is a group represented by —CHO, a compound represented by Formula (IV) wherein $R^1$ is a group represented by —CHO and a compound represented by Formula (IV) wherein $R^1$ is a group represented by —CHO.

In the labeled antibody, the antibody is not limited, and examples include an anti-HER2 human epidermal growth factor receptor 2) protein antibody, an anti-carcarcinoembryonic antigen (CEA) antibody, an anti-celladhesion molecule (CAM) antibody, anti-EGFR (epidermal growth factor receptor), etc. In the labeled antibody the antibody is preferably an amino group-containing antibody and more preferably an antibody that contains an amino group of a lysine residue. This is because, when the antibody is an amino group-containing antibody, it reacts with the group represented by —CHO of the one or more hexatriene-β-carbonyl compounds, thereby allowing the amino group to be captured promptly in a good yield.

Moreover, the present invention is directed to, as described above, a kit for producing an antibody labeled with one or more hexatriene-β-carbonyl compounds. The kit is characterized in that the kit contains:

one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO;

an antibody to be labeled; and optionally an instruction.

The kit is not limited insofar as it contains the one or more hexatriene-β-carbonyl compounds and the antibody to be labeled, and further may contain, for example, another organic compound (such as a low-molecular ligand), protein, peptide, sugar chain, etc.

In the kit, the antibody to be labeled is not limited, and examples include an anti-HER2 (human epidermal growth factor receptor 2) protein antibody, an anti-carcarcinoembryonic antigen (CEA) antibody, an anti-celladhesion molecule (CAM) antibody, anti-EGFR (epidermal growth factor receptor), etc. In the antibody to be labeled, the antibody is preferably an amino group-containing antibody and more preferably an antibody that contains an amino group of a lysine residue. This is because, when the antibody is an amino group-containing antibody, it reacts with the group represented by —CHO of the one or more hexatriene-β-carbonyl compounds, thereby allowing the amino group to be captured promptly in a good yield.

Moreover, the present invention is directed to a method for labeling a protein. The method for labeling a protein includes the steps of:

providing one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO, and protein; and reacting the one or more hexatriene-β-carbonyl compounds and the protein to label the protein with the one or more hexatriene-β-carbonyl compounds.

In the method for labeling a protein, the protein is not limited, and examples include cytokine, glycoprotein, a membrane receptor, etc. In the method for labeling a protein, the protein is preferably an amino group-containing protein and more preferably a protein that contains an amino group of a lysine residue. This is because, when the protein is an amino group-containing protein, it reacts with the group represented by —CHO of the one or more hexatriene-β-carbonyl compounds, thereby allowing the amino group to be captured promptly in a good yield.

In the method for labeling a protein, the step of reacting the one or more hexatriene-β-carbonyl compounds and the protein to label the protein with one or more hexatriene-β-carbonyl compounds can be carried out by admixing the one or more hexatriene-β-carbonyl compounds and the protein in a solution (such as water, a buffer solution) at, for example, room temperature to react the one or more hexatriene-β-carbonyl compounds and the protein, thereby labeling the protein with the one or more hexatriene-β-carbonyl compounds.

The present invention is directed to, as described above, a kit for labeling a protein. The kit for labeling a protein contains:

one or more hexatriene-β-carbonyl compounds selected from the group consisting of a compound represented by Formula (II) wherein $R^1$ is a group represented by —CHO, a compound represented by Formula (III) wherein $R^1$ is a group represented by —CHO and a compound represented by Formula (IV) wherein $R^1$ is a group represented by —CHO;

a protein to be labeled; and optionally an instruction.

In the kit for labeling a protein, the protein to be labeled is not limited, and examples include cytokine, glycoprotein, membrane receptor, etc. In the kit for labeling a protein, the protein to be labeled is preferably an amino group-containing protein and more preferably a protein that contains an amino group of a lysine residue. This is because, when the protein to be labeled is an amino group-containing protein, it reacts with the group represented by —CHO of the one or more hexatriene-β-carbonyl compounds, thereby allowing the amino group to be captured promptly in a good yield.

In the labeling method, the measurement method, the method for labeling a protein, the test composition, the test kit, the labeled antibody, the kit for producing an antibody, or the kit for labeling a protein described above, the compound represented by Formula (II) wherein $R^1$ is a group represented by —CHO is represented by Formula (II-100) below.

[Chemical Formula 190]

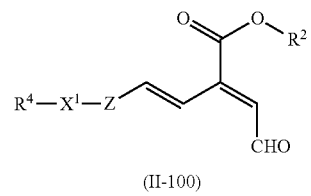

(II-100)

In the formula above, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula $-L^2-A^2-M^2$, $R^4$ is a carbonyl group substituted with a substituent that functions as a label, $X^1$ is a group represented by the formula $-L^1-A^1-$, the formula $-A^1-L^1-$ or the formula below:

[Chemical Formula 191]

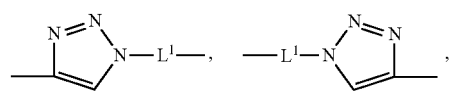

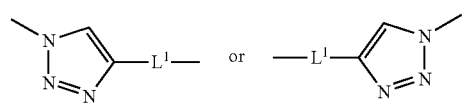

and Z is a group represented by the formula below:

[Chemical Formula 192]

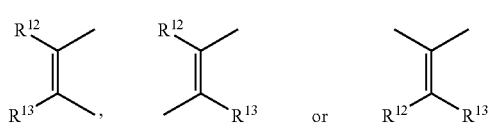

or a divalent group derived from an aromatic hydrocarbon or a divalent group derived from an aromatic hydrocarbon substituted with one or more substituents.

In the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-(CH_2)_n-$ (wherein n and m each independently represent an integer of 1 to 20), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20), $A^2$ is a group represented by $-O-$, $-CO_2-$, $-S-$ or $-NH-$, $M^2$ is a hydrogen atom or a protecting group for a group represented by $-OH$, $-CO_2H$, $-SH$ or $-NH_2$, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The compound represented by Formula (II-100) above is preferably such that in the formula, $R^2$ is a lower alkyl group or a lower alkyl group substituted with one or more substituents, $R^4$ is a group represented by the formula below:

[Chemical Formula 193]

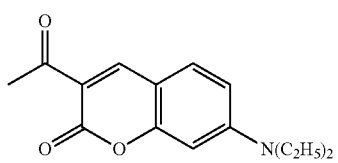

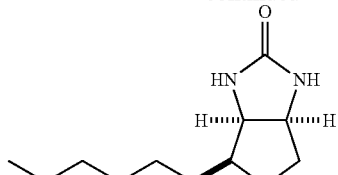

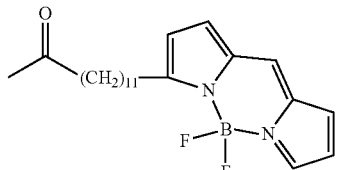

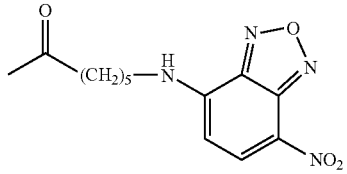

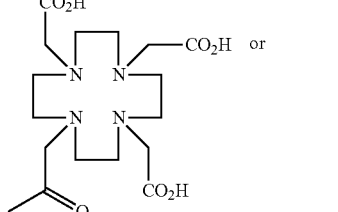

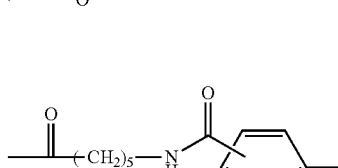

$X^1$ is a group represented by the formula $-L^1-A^1-$, the formula $-A^1-L^1-$ or the formula below:

[Chemical Formula 194]

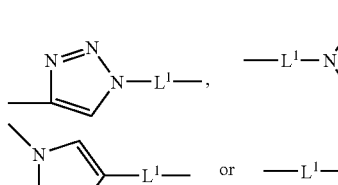

and Z is a divalent group derived from an aromatic hydrocarbon or a divalent group derived from an aromatic hydrocarbon substituted with one or more substituents.

In the formulae above, $L^1$ is a bond or a group represented by $-(CH_2)_n-CONH-$ or $-CONH-(CH_2)_n-$ (wherein n represents an integer of 1 to 20), and $A^1$ is a group represented by —O—, —$CO_2$—, —S— or —NH—.

The compound represented by Formula (II-100) above is more preferably such that in the formula,
$R^2$ is a lower alkyl group,
$R^4$ is a group represented by the formula below:

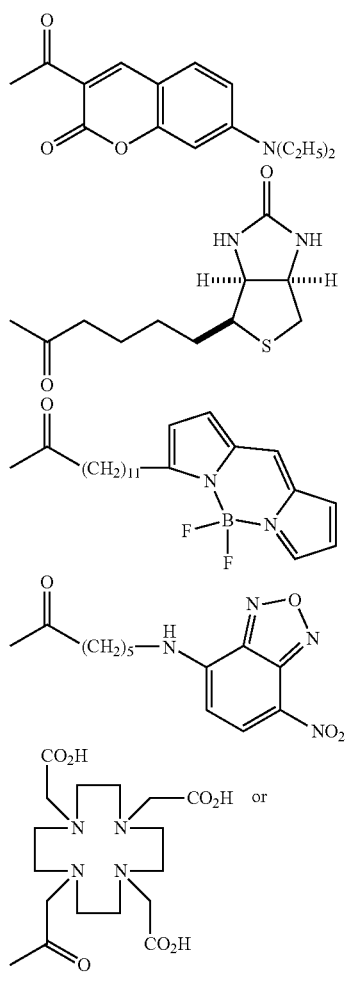

[Chemical Formula 195]

$X^1$ is a group represented by the formula -$L^1$-NH— or the formula —NH-$L^1$- (wherein $L^1$ is a bond or a group represented by —$(CH_2)_n$—CONH— or —CONH—$(CH_2)_n$— (wherein n represents an integer of 1 to 20), and
Z is a divalent group derived from an aromatic hydrocarbon.

It is more preferable that the compound represented by Formula (II-100) above is selected from the group consisting of:
a compound represented by Formula (II) represented by General Formula (I) wherein,
$R^2$ is an ethyl group,
$R^4$—$X^1$— is a group represented by the formula:

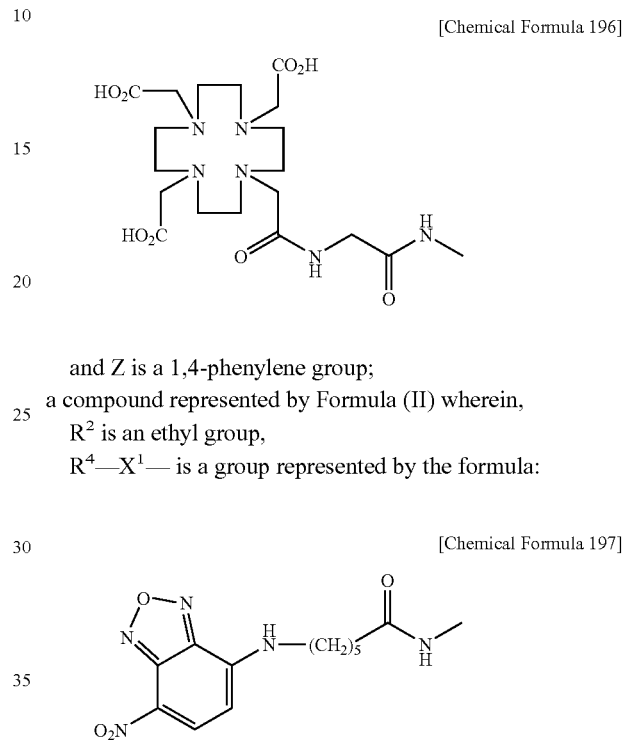

[Chemical Formula 196]

and Z is a 1,4-phenylene group;
a compound represented by Formula (II) wherein,
$R^2$ is an ethyl group,
$R^4$—$X^1$— is a group represented by the formula:

[Chemical Formula 197]

and Z is a 1,4-phenylene group; and
a compound represented by Formula (II) wherein,
$R^2$ is an ethyl group,
$R^4$—$X^1$— is a group represented by the formula:

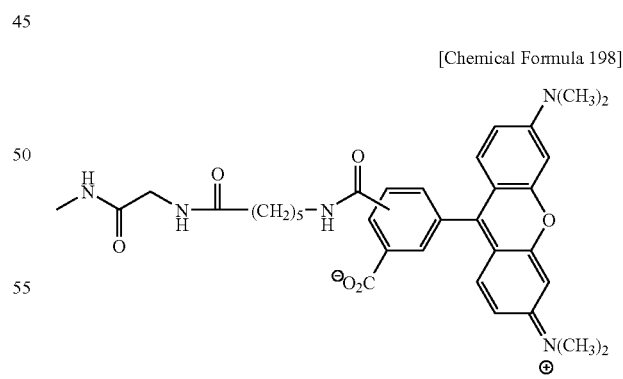

[Chemical Formula 198]

and Z is a 1,4-phenylene group.

In the labeling method, the measurement method, the method for labeling a protein, the test composition, the test kit, the labeled antibody, the kit for producing an antibody, or the kit for labeling a protein described above, the compound represented by Formula (III) wherein $R^1$ is a group represented by —CHO is represented by Formula (III-100) below.

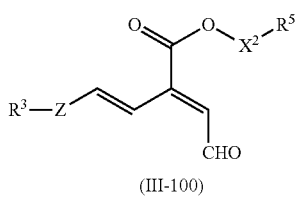

(III-100)

In the formula above, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula $-L^1-A^1-M^1$, the formula $-L^1-N_3$ or the formula:

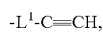
-$L^1$-C≡CH, [Chemical Formula 200]

$R^5$ is a carbonyl group substituted with a substituent that functions as a label, $X^2$ is a group represented by the formula $-L^2-A^2-L^3-$, and Z is a group represented by:

[Chemical Formula 201]

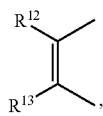 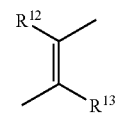 or 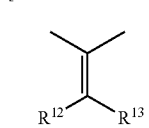

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)$—O—$(CH_2)_m$— (wherein n and m each independently represent an integer of 1 to 20), $M^1$ is a hydrogen atom, a group represented by —OH, —$CO_2H$, —SH or —$NH_2$, or a protecting group for a group represented by —OH, —$CO_2H$, —SH or —$NH_2$, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The compound represented by Formula (III-100) is preferably such that in the formula, $R^3$ is a hydrogen atom or a group represented by the formula $-L^1-A^1-M^1$, the formula $-L^1-N_3$ or the formula:

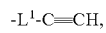
-$L^1$-C≡CH, [Chemical Formula 202]

$R^5$ is a group represented by the formula below:

[Chemical Formula 203]

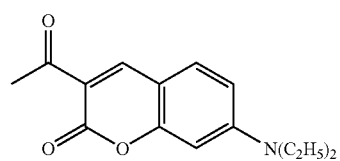

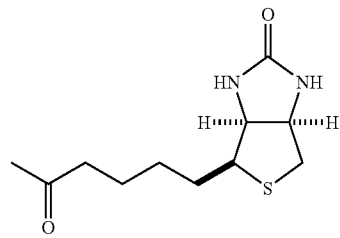

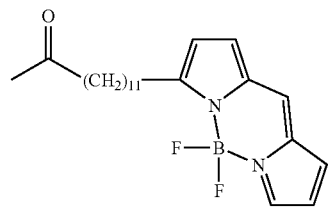

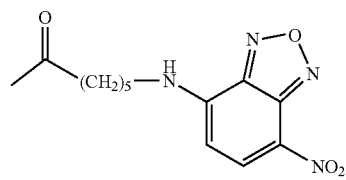

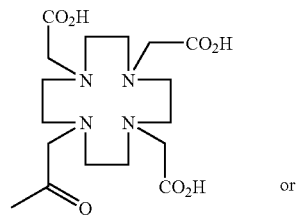 or

-continued

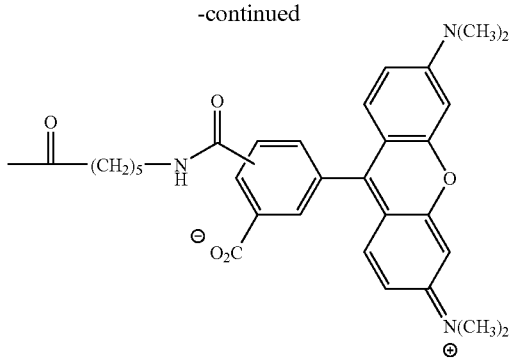

$X^2$ is a group represented by the formula -$L^2$-$A^2$-$L^3$-, and

Z is a divalent group derived from an aromatic hydrocarbon or a divalent group derived from an aromatic hydrocarbon substituted with one or more substituents.

In the formulae above, $L^1$ is a bond or a group represented by —$(CH_2)_n$—CONH— or —CONH—$(CH_2)_n$— (wherein n represents an integer of 1 to 20), $A^1$ is a group represented by —O—, —$CO_2$—, —S— or —NH—, $L^2$ is a bond or a group represented by —$(CH_2)$—O—$(CH_2)$— (wherein n and m each independently represent an integer of 1 to 20), $A^2$ is a group represented by —O—, —$CO_2$—, —S— or —NH—, $L^3$ is a bond or a group represented by —$(CH_2)_n$—O—$(CH_2)_m$— (wherein n and m each independently represent an integer of 1 to 20), and $M^1$ is a hydrogen atom or an acyl group.

The compound represented by Formula (III-100) is more preferably such that in the formula, $R^3$ is a hydrogen atom or a group represented by —$NH_2$, $R^5$ is a group represented by the formula below:

[Chemical Formula 204]

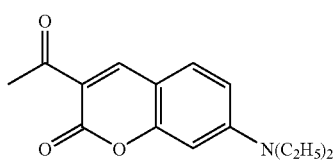

$X^2$ is a group represented by the formula -$L^2$-NH-$L^1$- (wherein $L^2$ is a bond or a group represented by —$(CH_2)_n$—O—$(CH_2)_m$— (wherein n and m each independently represent an integer of 1 to 20)), $L^3$ is a bond or a group represented by —$(CH_2)_n$—O—$(CH_2)_m$— (wherein n and m each independently represent an integer of 1 to 20), and Z is a divalent group derived from an aromatic hydrocarbon.

The compound represented by Formula (III-100) is further preferably a compound represented by Formula (III) wherein, $R^3$ is a hydrogen atom, $R^5$—$X^2$— is a group represented by the formula:

[Chemical Formula 205]

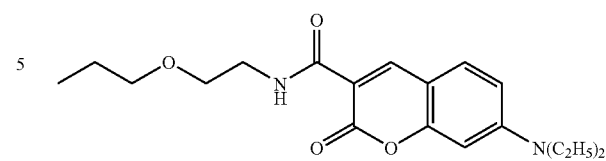

and Z is a 1,4-phenylene group.

In the labeling method, the measurement method, the method for labeling a protein, the test composition, the test kit, the labeled antibody, the kit for producing an antibody, or the kit for labeling a protein described above, the compound represented by Formula (IV) wherein $R^1$ is a group represented by —CHO is represented by Formula (IV-100) below.

[Chemical Formula 206]

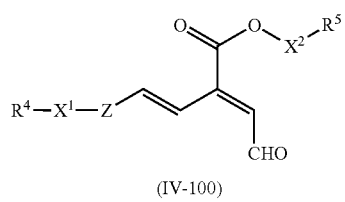

(IV-100)

In the formula above, $R^4$ is a carbonyl group substituted with a substituent that functions as a label, $R^5$ is a carbonyl group substituted with a substituent that functions as a label, $X^1$ is a group represented by the formula -$L^1$-$A^1$-, the formula -$A^1$-$L^1$- or the formula below:

[Chemical Formula 207]

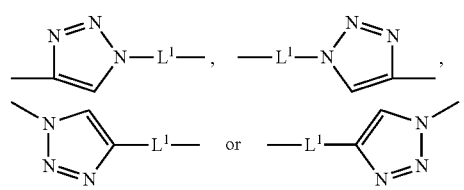

$X^2$ is a group represented by the formula -$L^1$-$A^2$-$L^3$-, and Z is a group represented by the formula below:

[Chemical Formula 208]

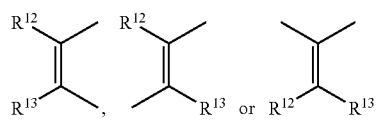

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_n$— (wherein n and m each independently represent an integer of 1 to 20), $A^2$ is a group represented by —O—, —$CO_2$—, —S— or —NH—, $L^3$ is a bond or a group represented by the formula —$(CH_2)_n$— or —$(CH_2)_n$—O—$(CH_2)_m$— (wherein n and m each independently represent an integer of 1 to 20), $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The compound represented by Formula (IV-100) is preferably such that in the formula, $R^4$ is a group represented by the formula below:

[Chemical Formula 209]

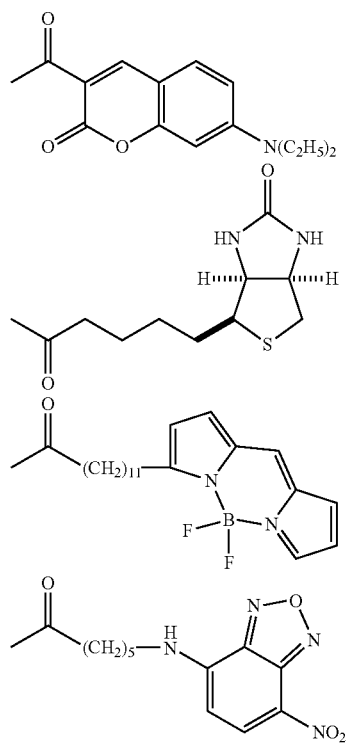

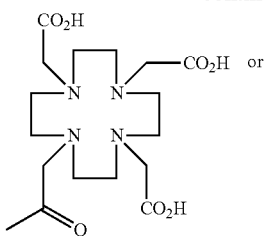 or

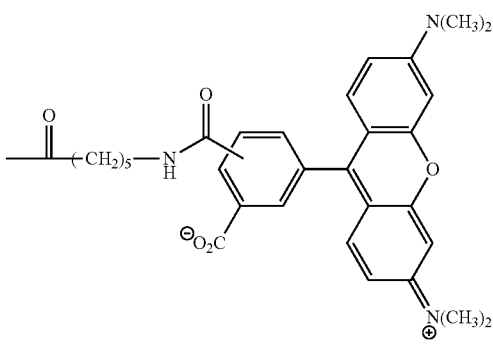

$R^5$ is a group represented by the formula below:

[Chemical Formula 210]

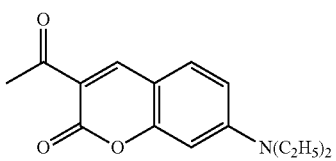

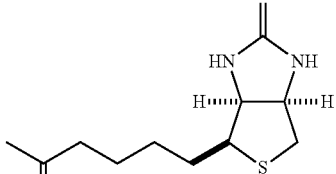

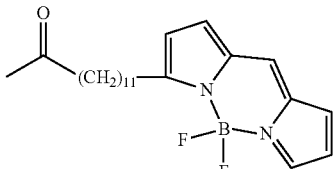

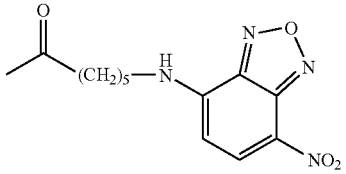

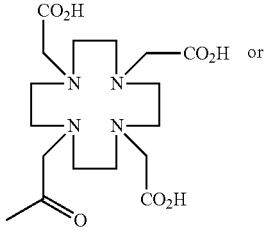 or

-continued

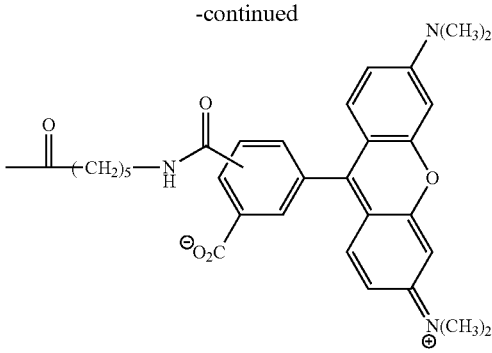

$X^1$ is a group represented by the formula -$L^1$-$A^1$-, the formula -$A^1$-$L^1$- or the formula below:

[Chemical Formula 211]

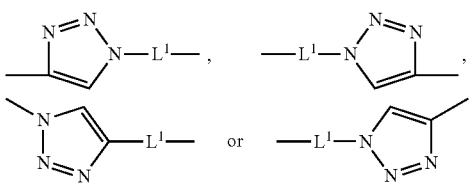

$X^2$ is a group represented by the formula -$L^3$-$A^2$-$L^3$-, and

Z is a divalent group derived from an aromatic hydrocarbon or a divalent group derived from an aromatic hydrocarbon substituted with one or more substituents.

In the formulae above, $L^1$ is a bond or a group represented by —$(CH_2)_n$—CONH— or —CONH—$(CH_2)_n$— (wherein n represents an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, and $L^3$ is a bond or a group represented by —$(CH_2)_n$—CONH— or —CONH—$(CH_2)_n$— (wherein n represents an integer of 1 to 20).

The compound represented by Formula (IV-100) is preferably such that in the formula, $R^4$ is a group represented by the formula below:

[Chemical Formula 212]

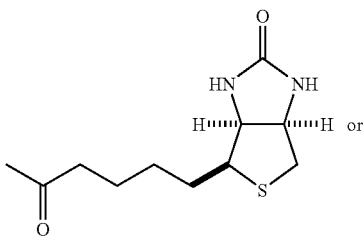

-continued

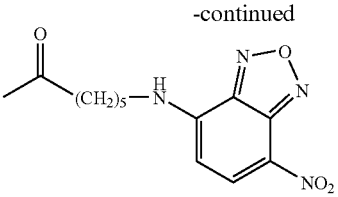

$R^5$ is a group represented by the formula below:

[Chemical Formula 213]

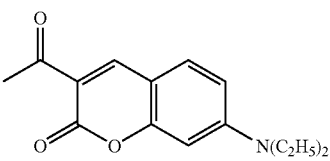

$X^1$ is a group represented by the formula -$L^1$-NH— or the formula —NH-$L^1$-, $X^2$ is a group represented by the formula -$L^2$-NH-$L^3$-, and Z is a divalent group derived from an aromatic hydrocarbon.

In the formulae above, $L^1$ is a bond or a group represented by —$(CH_2)_n$—CONH— or —CONH—$(CH_2)_n$— (wherein n represents an integer of 1 to 20), $L^2$ is a bond or a group represented by —$(CH_2)_n$—O—$(CH_2)_n$— (wherein n and m each independently represent an integer of 1 to 20), and $L^3$ is a bond or a group represented by —$(CH_2)_n$—CONH— or —CONH—$(CH_2)_n$— (wherein n represents an integer of 1 to 20).

The compound represented by Formula (IV-100) is more preferably represented by Formula (III) wherein, $R^4$—$X^1$— is a group represented by the formula:

[Chemical Formula 214]

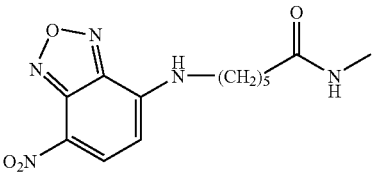

$R^5$—$X^2$— is a group represented by the formula:

[Chemical Formula 215]

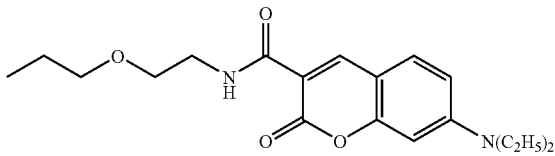

and Z is a 1,4-phenylene group.

In the method for producing a PET contrast agent and the method for producing a labeled antibody described above, the compound represented by Formula (II) wherein $R^1$ is a group represented by —CHO and $R^4$ is a carbonyl group substituted with a substituent that functions as a label the carbonyl group substituted with a substituent that functions as a label being able to coordinate with a radioactive metal, is represented by Formula (II-200) below.

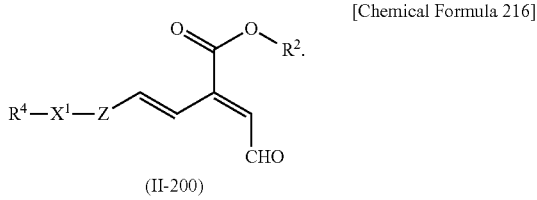

(II-200)

In the formula, $R^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula -$L^2$-$A^2$-$M^2$, $R^4$ is a carbonyl group substituted with a substituent that functions as a label the carbonyl group substituted with a substituent that functions as a label being able to coordinate with a radioactive metal $X^1$ is a group represented by the formula -$L^1$-$A^1$-, the formula -$A^1$-$L^1$- or the formula below:

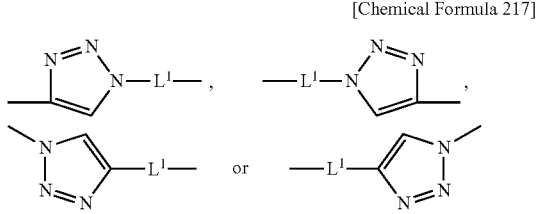

and Z is a group represented by the formula below:

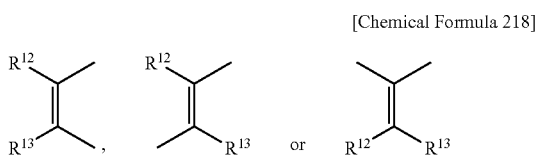

or a divalent group derived from an aromatic hydrocarbon or a divalent group derived from an aromatic hydrocarbon substituted with one or more substituents.

In the formulae above, $L^1$ is a bond or a group represented by the formula —$(CH_2)_n$—, the formula —$(CH_2)_n$—O—$(CH_2)_m$—, the formula —$(CH_2)_n$—CONH— or the formula —CONH—$(CH_2)_n$—O— (wherein n and m each independently represent an integer of 1 to 20), $A^1$ is a group represented by —O—, —$CO_2$—, —S— or —NH—, $L^2$ is a bond or a group represented by —$(CH_2)_n$—O—$(CH_2)_m$— (wherein n and m each independently represent an integer of 1 to 20), $A^2$ is a group represented by —O—, —$CO_2$—, —S— or —NH—, $M^2$ is a hydrogen atom or a protecting group for a group represented by —OH, —$CO_2H$, —SH or —$NH_2$, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, a lower ar(lower)alkoxy group, an aryl group, a lower aryl group, a heteroaryl group or a lower heteroaryl group, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The compound represented by Formula (II-200) is preferably such that in the formula, $R^2$ is a lower alkyl group or a lower alkyl group substituted with one or more substituents, $R^4$ is a group represented by the formula below:

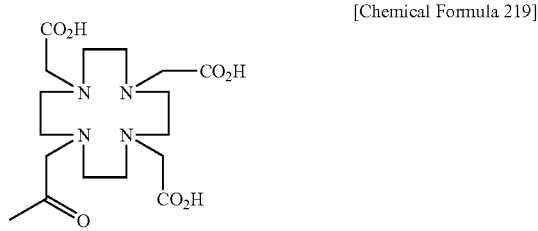

$X^1$ is a group represented by the formula -$L^1$-$A^1$-, the formula -$A^1$-$L^1$- or the formula below:

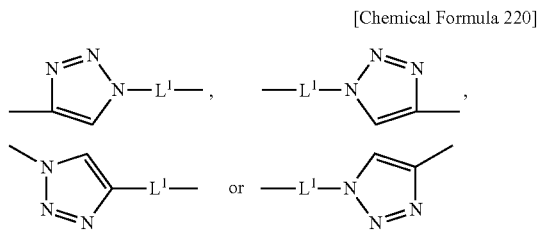

and Z is a divalent group derived from an aromatic hydrocarbon or a divalent group derived from an aromatic hydrocarbon substituted with one or more substituents.

In the formulae above it is preferable that, $L^1$ is a bond or a group represented by —$(CH_2)_n$—CONH— or —CONH—$(CH_2)_n$— (wherein n represents an integer of 1 to 20), and $A^1$ is a group represented by —O—, —$CO_2$—, —S— or —NH—.

The compound represented by Formula (II-200) is more preferably such that in the formula above, $R^2$ is a lower alkyl group, $R^4$ is a group represented by the formula below:

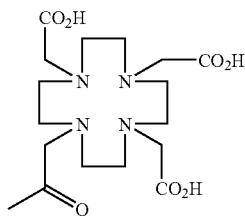

[Chemical Formula 221]

$X^1$ is a group represented by the formula $-L^1-NH-$ or the formula $-NH-L^1-$ (wherein $L^1$ is a bond or a group represented by $-(CH_2)_n-CONH-$ or $-CONH-(CH_2)_n-$ (wherein n represents an integer of 1 to 20)), and Z is a divalent group derived from an aromatic hydrocarbon.

The compound represented by Formula (II-200) is further preferably such that in the formula, $R^2$ is an ethyl group, $R^4-X^1-$ is a group represented by the formula below:

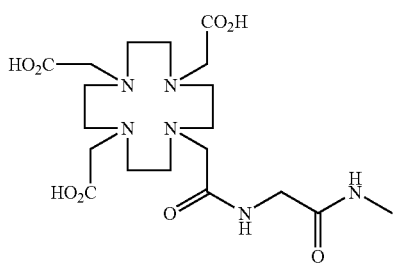

[Chemical Formula 222]

and Z is a 1,4-phenylene group.

In the method for producing a PET contrast agent and the method for producing a labeled antibody described above, the compound represented by Formula (III) wherein $R^1$ is a group represented by $-CHO$ and $R^5$ is a carbonyl group substituted with a substituent that functions as a label the carbonyl group substituted with a substituent that functions as a label being able to coordinate with a radioactive metal is represented by Formula (III-200) below.

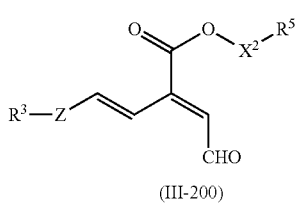

[Chemical Formula 223]

(III-200)

In the formula above, $R^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by the formula $-L^1-A^1-M^1$, the formula $-L^1-N_3$ or the formula:

$-L^1-C\equiv CH$, [Chemical Formula 224]

$R^5$ is a carbonyl group substituted with a substituent that functions as a label the carbonyl group substituted with a substituent that functions as a label being able to coordinate with a radioactive metal, $X^2$ is a group represented by the formula $-L^2-A^2-L^3-$, and Z is a group represented by the formula below:

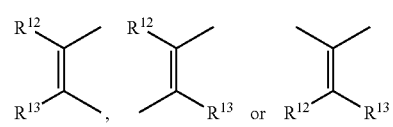

[Chemical Formula 225]

or a divalent group derived from an aromatic hydrocarbon or a divalent group derived from an aromatic hydrocarbon substituted with one or more substituents.

In the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-(CH_2)_n-$ (wherein n and m each independently represent an integer of 1 to 20), $A^1$ is a group represented by $-O-$, $-CO_2-$, $-S-$ or $-NH-$, $L^2$ is a bond or a group represented by $-(CH_2)_n-O-(CH_2)_m-$ (wherein n and m each independently represent an integer of 1 to 20), $A^2$ is a group represented by $-O-$, $-CO_2-$, $-S-$ or $-NH-$, $L^3$ is a bond or a group represented by the formula $-(CH_2)_n-$ or $-(CH_2)_n-O-(CH_2)_m-$ (wherein n and m each independently represent an integer of 1 to 20), $M^1$ is a hydrogen atom, a group represented by $-OH$, $-CO_2H$, $-SH$ or $-NH_2$, or a protecting group for a group represented by $-OH$, $-CO_2H$, $-SH$ or $-NH_2$, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The compound represented by Formula (III-200) is preferably such that in the formula, $R^3$ is a hydrogen atom or a group represented by the formula $-L^1-A^1-M^1$, the formula $-L^1-N_3$ or the formula:

$-L^1-C\equiv CH$, [Chemical Formula 226]

$R^5$ is a group represented by the formula below:

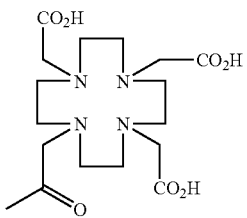
[Chemical Formula 227]

$X^2$ is a group represented by the formula $-L^2-A^2-L^3-$, and

Z is a divalent group derived from an aromatic hydrocarbon or a divalent group derived from an aromatic hydrocarbon substituted with one or more substituents.

It is preferable that in the formulae above, $L^1$ is a bond or a group represented by $-(CH_2)_n-$ $CONH-$ or $-CONH-(CH_2)_n-$ (wherein n represents an integer of 1 to 20), $A^1$ is a group represented by $-O-$, $-CO_2-$, $-S-$ or $-NH-$, $L^2$ is a bond or a group represented by $-(CH_2)_n-O-$ $(CH_2)_m-$ (wherein n and m each independently represent an integer of 1 to 20), $A^2$ is a group represented by $-O-$, $-CO_2-$, $-S-$ or $-NH-$, $L^3$ is a bond or a group represented by $-(CH_2)_n-O-$ $(CH_2)_m-$ (wherein n and m each independently represent an integer of 1 to 20), and $M^1$ is a hydrogen atom or an acyl group.

In connection with the method for producing a PET contrast agent and the method for producing a labeled antibody described above, the compound represented by Formula (IV) wherein $R^1$ is a group represented by $-CHO$ and at least one of $R^4$ and $R^5$ is a carbonyl group substituted with a substituent that functions as a label the carbonyl group substituted with a substituent that functions as a label being able to coordinate with a radioactive metal is represented by Formula (IV-200) below.

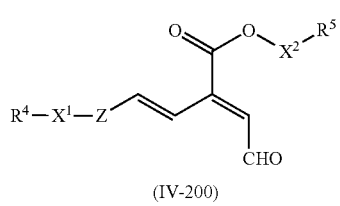
[Chemical Formula 228]

(IV-200)

In the formula above, $R^4$ is a carbonyl group substituted with a substituent that functions as a label, $R^5$ is a carbonyl group substituted with a substituent that functions as a label, the carbonyl group substituted with a substituent that functions as a label for at least one of $R^4$ and $R^5$ is capable to coordinate with a radioactive metal, $X^1$ is a group represented by the formula $-L^1-A^1-$, the formula $-A^1-L^1-$ or the formula below:

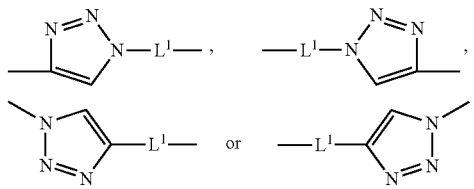
[Chemical Formula 229]

$X^2$ is a group represented by the formula $-L^2-A^2-L^3-$, and

Z is a group represented by the formula below:

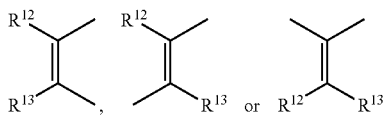
[Chemical Formula 230]

or a divalent group derived from an aromatic hydrocarbon or a divalent group derived from an aromatic hydrocarbon substituted with one or more substituents.

In the formulae above, $L^1$ is a bond or a group represented by the formula $-(CH_2)_n-$, the formula $-(CH_2)_n-O-(CH_2)_m-$, the formula $-(CH_2)_n-CONH-$ or the formula $-CONH-$ $(CH_2)_n-$ (wherein n and m each independently represent an integer of 1 to 20), $A^1$ is a group represented by $-O-$, $-CO_2-$, $-S-$ or $-NH-$, $L^2$ is a bond or a group represented by $-(CH_2)_n-O-$ $(CH_2)_m-$ (wherein n and m each independently represent an integer of 1 to 20), $A^2$ is a group represented by $-O-$, $-CO_2-$, $-S-$ or $-NH-$, $L^3$ is a bond or a group represented by the formula $-(CH_2)_n-$ or $-(CH_2)_n-O-(CH_2)_m-$ (wherein n and m each independently represent an integer of 1 to 20), $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

The compound represented by Formula (IV-200) is preferably such that in the formula, $R^4$ is a group represented by the formula below:

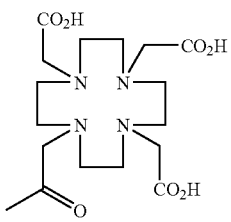
[Chemical Formula 231]

$R^5$ is a group represented by the formula below:

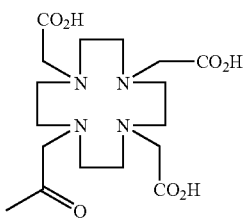
[Chemical Formula 232]

$X^1$ is a group represented by the formula $-L^1-A^1-$, the formula $-A^1-L^1-$ or the formula below:

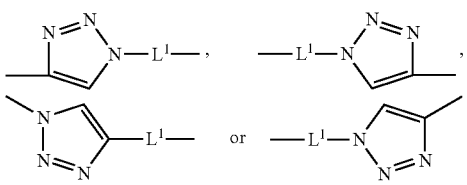
[Chemical Formula 233]

$X^2$ is a group represented by the formula $-L^2-A^2-L^3-$, and

Z is a divalent group derived from an aromatic hydrocarbon or a divalent group derived from an aromatic hydrocarbon substituted with one or more substituents.

In the description of the present specification, the following abbreviations are used.
BOC: t-butoxycarbonyl,
TBDPS: t-butyldiphenylsilyl
THF: tetrahydrofuran,
AIBN: 2,2'-azobisisobutyronitrile,
DMF: dimethylformamide
$Pd_2(dba)_3$: tris(dibenzylideneacetone)dipalladium(0)
P(2-furyl)$_3$: tri(2-furyl)phosphine
Dess-Martin periodinane reagent: 1,1,1-triacetoxy-1,1-dihydro-1,2-benziodoxol-3(1H)-one,
IBX resin: (2-iodoxybenzoic acid) resin,
EDC: 1-(3-dimethylaminopropyl)-3-ethylcarbodiimide hydrochloride,
DMAP: 4-dimethylaminopyridine,
HBTU: o-benzotriazol-1-yl-N,N,N',N'-tetramethyluronium hexahydrophosphate,
PDC: pyridinium dichromate,
TFA: trifluoroacetic acid,
Ar: argon
TBAF: tetrabutylammonium fluoride,
PBS: phosphate buffered saline.

EXAMPLE 1

Production of ethyl (E,E)-4-hydroxy-2-(4-(2-aminoacetamide)styryl)but-2-enoate (Compound 5) ($R^1$ being $-CH_2OH$, $R^2$ being $-C_2H_5$, $R^3$ being a group represented by the formula $-L^1-A^1-M^1$, Z being 1,4-phenylene, $L^1$ being $-NH-C(=O)-CH_2-$, $A^1$ being $-NH-$, and $M^1$ being H in Formula (I))

Compound 5 as described above was produced according to Scheme 11 below.

Scheme 11

[Chemical Formula 234]

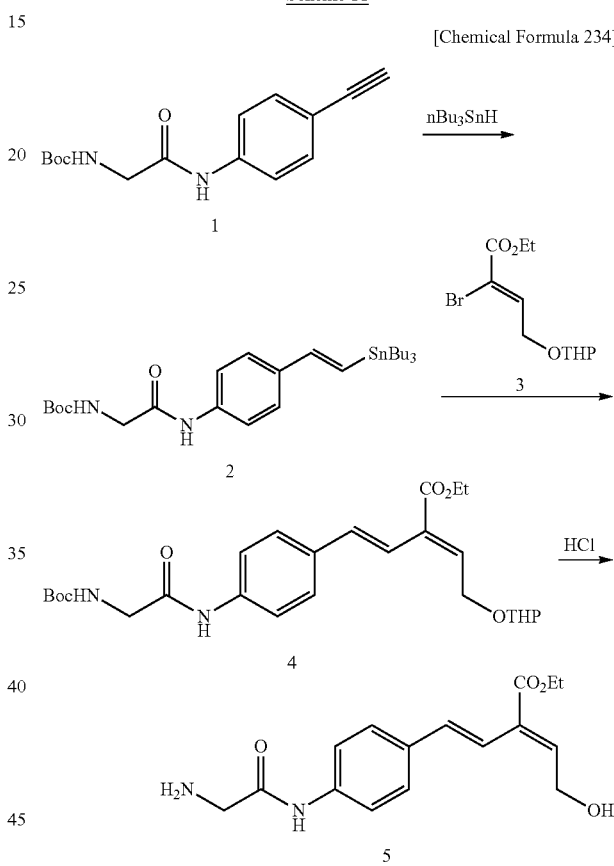

1.1 Production of p(E)-8-(tri-n-butylstannyl)vinyl-N-boc-glycylaniline (Compound 2)

AIBN (13 mg, 0.084 mmol and Bu$_3$SnH (742 µl, 2.75 mmol) were added to a 6 ml solution (THF:benzene=1:1) of (N-tert-butoxycarbonylglycyl)aminophenylacetylene (Compound 1) (582 mg, 2.12 mmol) at room temperature. This mixture was heated to 90° C., stirred for 40 minutes, and then concentrated in vacuo. The residue was purified by alumina chromatography (from 10% to 20% ethyl acetate in hexane), thereby giving the titled Compound 2 (1.03 g, 86%).

$^1$H NMR (CDCl$_3$) δ: 7.43 (d, J=8.24 Hz, 2H), 7.23 (d, J=8.39 Hz, 2H), 6.73 (d, J=19.38 Hz, 2H), 6.65 (d, J=19.38 Hz, 2H), 5.83 (s, 1H) 4.01 (q, J=7.12 Hz, 2H), 3.90-3.83 (br m, 2H), 2.69 (s, 3H), 1.92 (s, 3H), 1.46 (tt, J=26.40, 8.70 Hz, 6H), 1.35 (s, 9H), 1.25 (dd, J=14.72, 7.40 Hz, 6H), 1.14 (t, J=7.17 Hz, 4H), 0.81 (t, J=7.32 Hz, 9H).

1.2 Production of ethyl (E,E)-pN-Boc-glycylanilyl)-4-(tetrahydro-2H-pyran-2-yloxy)but-2-enoate (Compound 4)

$Pd_2(dba)_3$ (17 mg, 0.019 mmol) and $P(2-furyl)_3$ (18 mg, 0.078 mmol) were added to a DMF (1 ml) solvent, and the resulting mixture was stirred at room temperature for 10 minutes. Next, a DMF (4 ml) solution of Compound 2 described above (500 mg, 0.983 mmol) and ethyl (Z)-2-bromo-4-(tetrahydro-2H-pyran-2-yloxy)-2-butenoate (Compound 3) (345 mg, 1.18 mmol) was added to the aforementioned mixture at room temperature dropwise, and LiCl (82 mg, 1.96 mmol) then was added. The reaction mixture was heated to 110° C., stirred for 30 minutes, and then introduced into an Erlenmeyer flask charged with ethyl acetate and 3% aqueous ammonia for extraction with ethyl acetate. The organic layer was washed with saturated brine, dried over magnesium sulfate and concentrated in vacuo. The residue thus obtained was purified by silica gel chromatography (10% to 50% ethyl acetate in hexane), thereby giving the titled Compound 4 (478 mg, 73%).

$^1H$ NMR ($CDCl_3$) δ: 7.51 (d, J=8.39 Hz, 2H), 7.39 (d, J=8.39 Hz, 2H), 6.85-6.71 (m, 3H), 5.44 (s, 1H), 4.70 (t, J=3.51 Hz, 1H), 4.60 (dd, J=14.88, 5.72 Hz, 1H), 4.39 (dd, J=14.88, 6.48 Hz, 1H), 4.27 (q, J=7.17 Hz, 2H), 3.94 (d, J=5.65 Hz, 2H), 3.88 (dt, J=14.09, 4.92 Hz, 1H, 3.56-3.52 (m, 1H), 1.91-1.82 (m, 1H), 1.75 (tt, J=11.37, 3.51 Hz, 1H), 1.67-1.51 (m, 3H), 1.48 (s, 9H), 1.34 (t, J=7.10 Hz, 3H).

ESI-MS m/z: 427.12, $[M+Na]^+$ 1.3 Production of ethyl (E,E)-4-hydroxy-2-(4-(2-aminoacetamide)styryl)but-2-enoate (Compound 5)

6 N hydrochloric acid (3 ml) was added to a MeOH (3 ml) solution of Compound 4 described above (208 mg, 0.426 mmol) dropwise at 0° C. This mixture was stirred at 0° C. for 10 minutes, warmed to room temperature, and then stirred for 2 more hours. Ice was added to the reaction mixture, and saturated aqueous $NaHCO_3$ and aqueous 1 N NaOH were added for neutralization. The reaction mixture was desalted by passing it through a column filled with LH20 beads and then concentrated in vacuo, thereby giving the titled Compound 5 (130 mg, quantitative).

$^1H$ NMR ($CD_3OD$) δ: 7.61 (2H, d, J=8.24 Hz), 7.45 (2H, d, J=8.39 Hz), 6.87 (1H, d, J=16.33 Hz), 6.79 (1H, d, J=16.78 Hz), 6.79 (1H, t, J=6.87 Hz), 4.48 (2H, d, J=6.10 Hz), 4.26 (2H, q, J=7.12 Hz), 3.90 (2H, s), 1.33 (3H, t, J=7.17 Hz).

ESI-MS m/z: 305.17, $[M+H]^+$

EXAMPLE 2

Production of 10-(2-(2-(4-((1E,3E)-3-ethoxycarbonyl-5-hydroxypenta-1,3-dienyl)-phenylamino)-2-oxoethylamino)-2-oxoethyl)-1,4,7,10-tetraazacyclododecane-1,4,7-triacetic acid (Compound 7) (in Formula (II), $R^1$ being —$CH_2OH$, $R^2$ being —$C_2H_5$, $X^1$ being a group represented by the formula -$L^1$-$A^1$-, Z being 1,4-phenylene, $L^1$ being —NH—C(=O)—$CH_2$—, $A^1$ being —NH—, and $R^4$ being as follows)

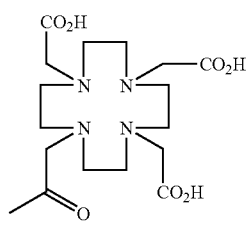

[Chemical Formula 235]

Compound 7 described above was produced according to Scheme 12 below.

Scheme 12

[Chemical Formula 236]

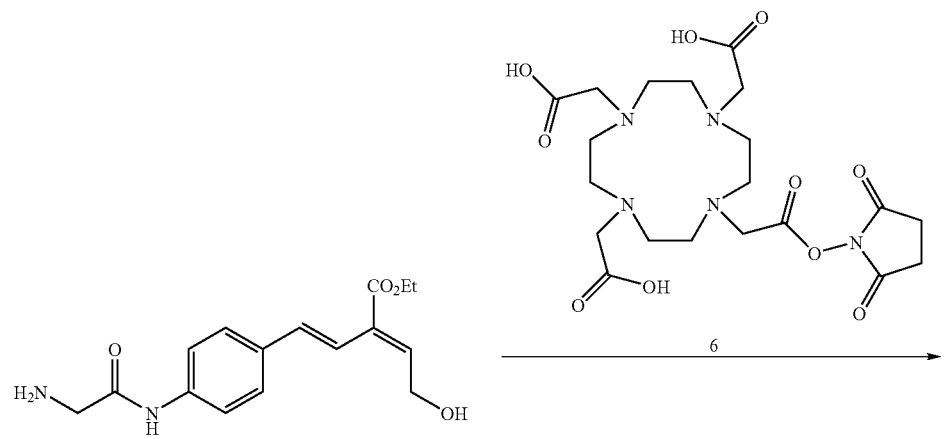

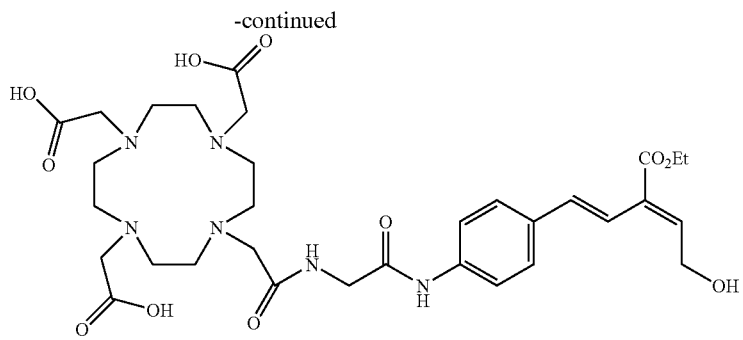

7

1,4,7,10-Tetraazacylcododecane-1,4,7,10-tetraacetic acid succinimidyl ester (DOTA-NHS) (Compound 6) (4.3 mg, 8.6 μmol) and triethylamine (10 μl, 78 μmol) were added to a DMF (0.2 ml) solution of Compound 5 described above (2.4 mg, 7.8 mmol) at room temperature, and stirred for 4 hours. The reaction mixture was concentrated in vacuo, and the residue was subjected to gel filtration using LH20 in of $CHCl_3$:MeOH:$H_2O$=1:1:0.1), thereby giving the titled Compound 7 (3.1 mg, 58%).

ESI-MS m/z: 691.26 $[M+H]^+$, 713.24 $[M+Na]^+$

EXAMPLE 3

Production of 10-(2-(2-(4-((1E,3E)-3-ethoxycarbonyl-5-oxopenta-1,3-dienyl)-phenylamino)-2-oxoethylamino)-2-oxoethyl)-1,4,7,10-tetraazacyclododecane-1,4,7-triacetic acid (Compound 8) (in Formula (II), $R^1$ being —CHO, $R^2$ being —$C_2H_5$, $X^1$ being a group represented by the formula -$L^1$-$A^1$-, Z being 1,4-phenylene, $L^1$ being —NH—C(=O)—$CH_2$—, $A^1$ being —NH—, and $R^4$ being as follows)

[Chemical Formula 237]

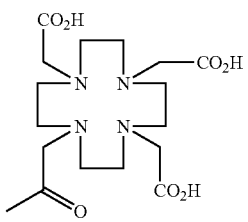

Compound 8 described above was produced according to Scheme 13 below.

Scheme 13

[Chemical Formula 238]

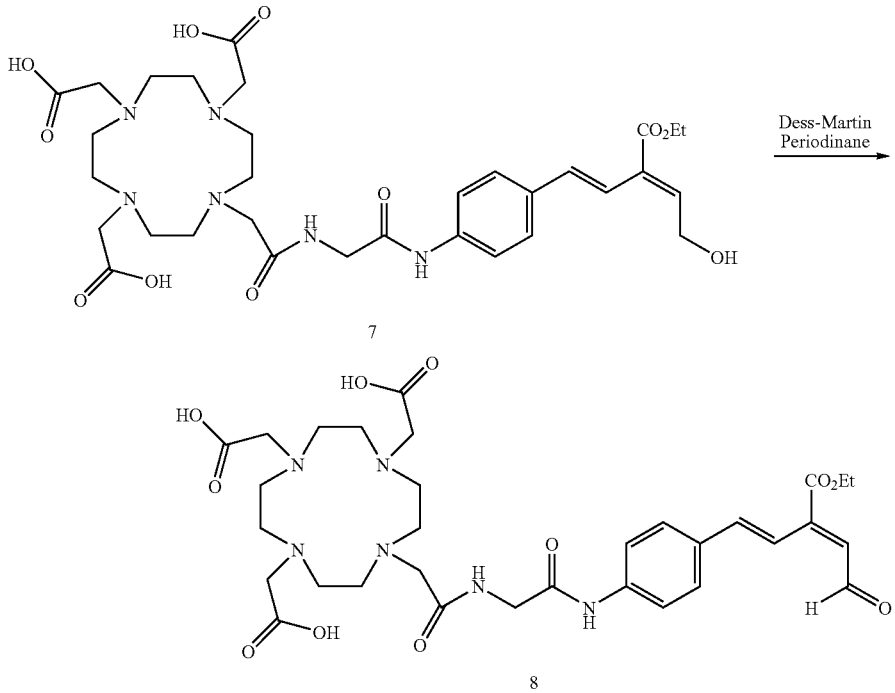

A Dess-Martin periodinane reagent (1.8 mg, 4.3 µmol) was added to a mixed DMF (0.09 ml) and $CH_2Cl_2$ (0.2 ml) solution of Compound 7 described above (1.5 mg, 2.1 µmol at room temperature and stirred for 20 minutes. The reaction mixture was subjected to gel filtration using LH20 (mixture of $CHCl_3$:MeOH:$H_2O$=1:1:0.1), thereby giving a DMF solution (40 µl) of the titled Compound 8.

ESI-MS m/z: 689.11 [M+H]$^+$

EXAMPLE 4

Production of ethyl (E,E)-4-hydroxy-2-(4-(2-(6-(tetramethylrhodamine-5-(and -6)-carboxamido)hexaneamide)acetamide)styryl)but-2-enoate (Compound 13) (in Formula (II), $R^1$ being —$CH_2OH$, $R^2$ being —$C_2H_5$, $X^1$ being a group represented by the formula -$L^1$-$A^1$-, Z being 1,4-phenylene, $L^1$ being —NH—C(=O)—$CH_2$—, $A^1$ being —NH—, and $R^4$ being as follows)

[Chemical Formula 239]

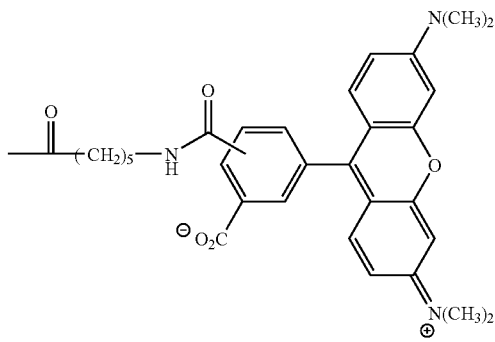

Compound 13 described above was produced according to Scheme 14 below.

Scheme 14

[Chemical Formula 240]

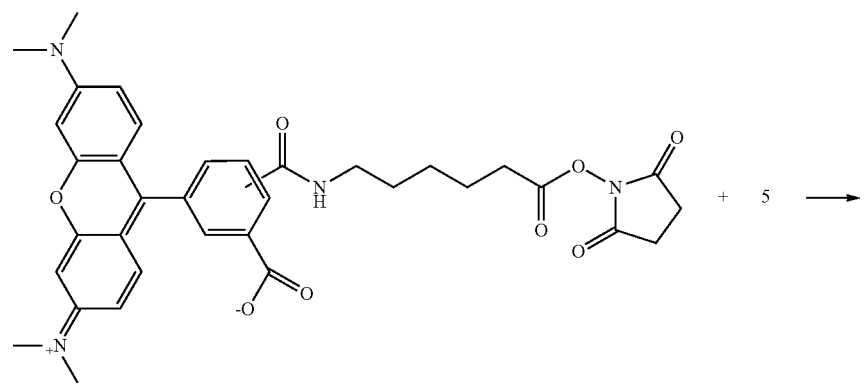

12

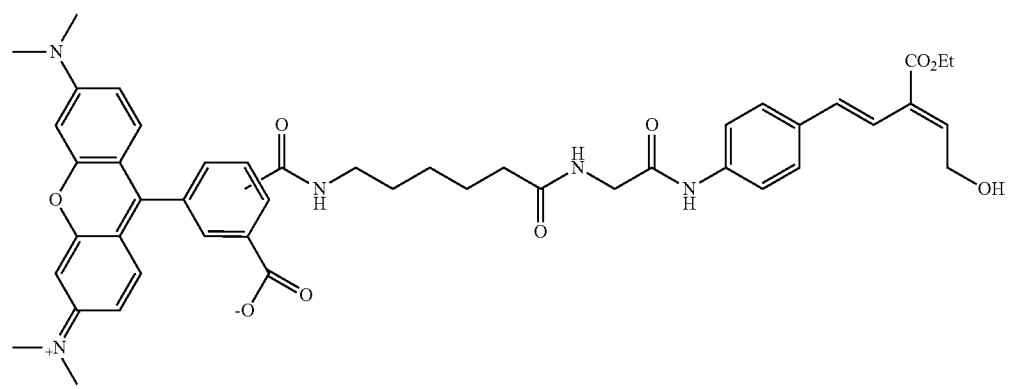

13

6-(Tetramethylrhodamine-5-(and -6)-carboxamido)hexanoic acid succinimidyl ester (TAMRA-OSu) (Compound 12) (0.42 mg, 0.65 µmol) was added to a mixed DMF (25 µl) and $CH_2Cl_2$ (25 µl) solution of Compound 5 described above (0.2 mg, 0.65 µmol), and stirred at room temperature for 30 minutes. The reaction mixture was purified by preparative thin-layer chromatography, thereby giving the titled Compound 13 (0.62 mg, quantitative).

ESI-MS m/z: 830.37 [M+H]$^+$

EXAMPLE 5

Production of ethyl (E,E)-4-oxo-2-(4-(2-(6-(tetramethyl-rhodamine-5-(and -6)-carboxamido)hexaneamide)acetamide)styryl)but-2-enoate (Compound 15) (in Formula (II), $R^1$ being —CHO, $R^2$ being —$C_2H_5$, $X^1$ being a group represented by the formula -$L^1$-$A^1$-, Z being 1,4-phenylene, $L^1$ being —NH—C(=O)—$CH_2$—, $A^1$ being —NH—, and $R^4$ being as follows)

[Chemical Formula 241]

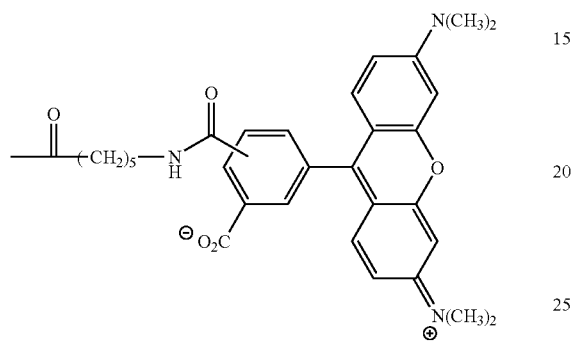

Compound 15 described above was produced according to Scheme 15 below.

Scheme 15

[Chemical Formula 242]

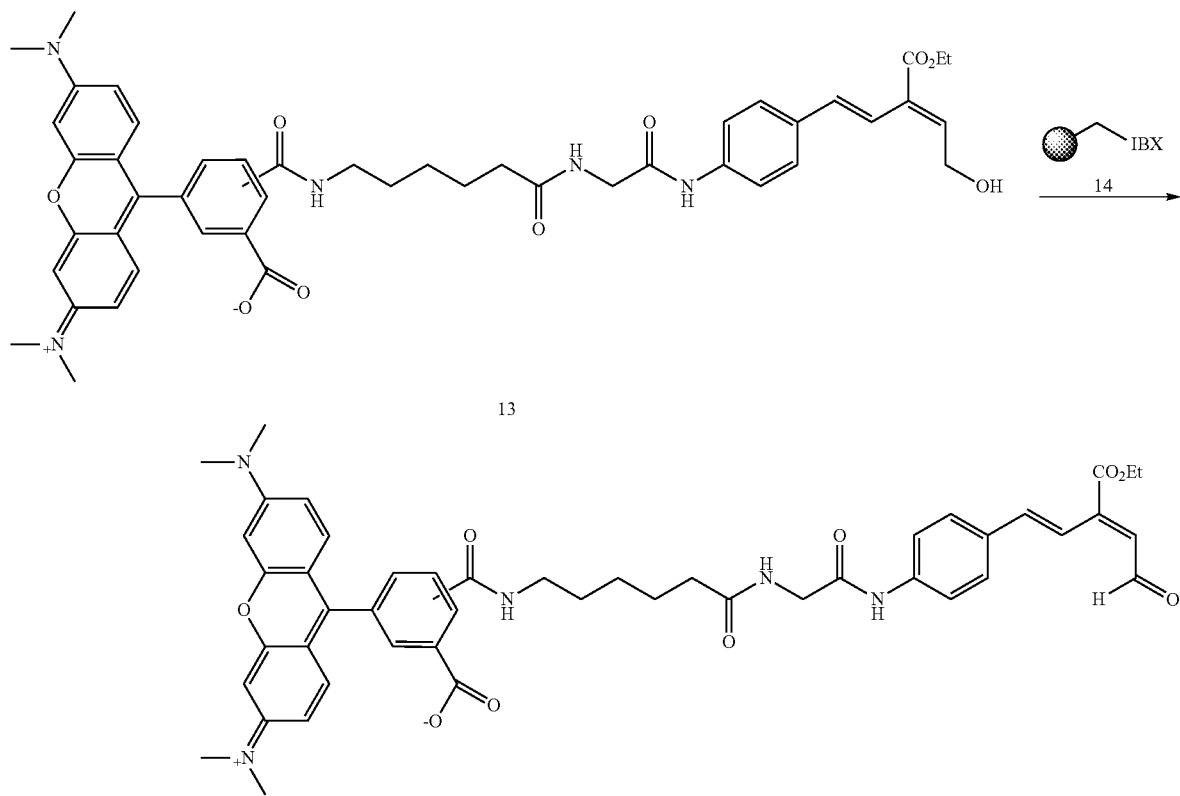

IBX resin (manufactured by Merck KGaA) (Compound 14) (1.3 mg, 1.2 µmol) was added to a mixed DMF (25 µl) and CH$_2$Cl$_2$ (25 µl) solution of Compound 13 described above (0.5 mg, 0.60 µmol), and gently stirred at room temperature for 1 hour. The reaction mixture was filtered, and CH$_2$Cl$_2$ in the filtrate was concentrated in vacuo, thereby giving a DMF solution of the titled Compound 15.

ESI-MS m/z: 830.37 [M+H]$^+$

EXAMPLE 6

Production of ethyl (E,E)-4-hydroxy-2-(4-aminostyryl)but-2-enoate (Compound 30) (R$^1$ being —CH$_2$OH, R$^2$ being —C$_2$H$_5$, R$^3$ being a group represented by the formula -L$^1$-A$^1$-M$^1$, Z being 1,4-phenylene, L$^1$ being a bond, A$^1$ being —NH—, and M$^1$ being H in Formula (I))

Compound 30 described above was produced according to Scheme 16 below.

Scheme 16

[Chemical Formula 243]

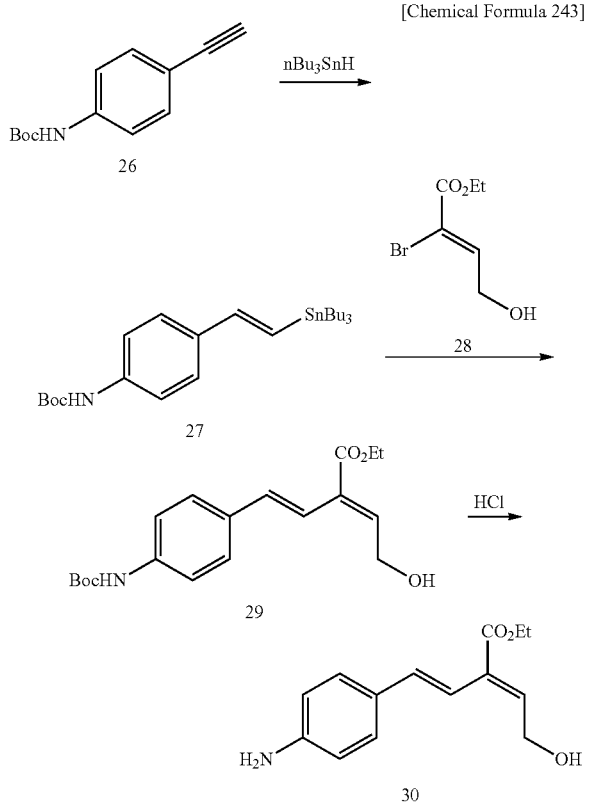

6.1 Production of (E)-tert-butyl-4-(2-(tri-n-butylstannyl)vinyl)phenylcarbamate (Compound 27)

AIBN (13 mg, 0.084 mmol) and Bu$_3$SnH (742 µl, 2.75 mmol) were added at room temperature to a benzene (10 ml) solution of 4-ethynyl-tert-butoxycarbonylaniline (Compound 26) (500 mg, 2.30 mmol). This mixture was heated to 90° C., stirred for 50 minutes, and then concentrated in vacuo. The residue thus obtained was purified by alumina chromatography (10% ethyl acetate in n-hexane), thereby giving the titled Compound 27 (0.97 g, 84%).

$^1$H NMR (CDCl$_3$) δ: 7.31 (dd, J=14.95, 8.70 Hz, 4H), 6.80 (d, J=19.53 Hz, 2H), 6.70 (d, J=19.53 Hz, 2H), 6.46 (s, 1H), 1.58-1.48 (m, 20H), 1.32 (td, J=14.69, 7.27 Hz, 6H), 0.94 (t, J=8.09 Hz, 3H), 0.88 (t, J=7.32 Hz, 9H).

6.2 Production of ethyl (E,E)-4-hydroxy-2-(4-N-tert-butoxycarbonylaminostyryl)but-2-enoate (Compound 29)

Pd$_2$(dba)$_3$ (16 mg, 0.018 mmol) and P(2-furyl)$_3$ (17 mg, 0.073 mmol) were added to a DMF (2 ml) solvent, and the mixture was stirred at room temperature for 10 minutes. Next, a DMF (8 ml) solution of Compound 27 described above (456 mg, 0.89 mmol) and ethyl (Z)-2-bromo-4-hydroxy-2-butenoate (Compound 28) (225 mg, 1.08 mmol) was added to the mixture at room temperature, and then LiCl (76 mg, 1.79 mmol) was added. The reaction mixture was heated to 110° C., stirred for 45 minutes, and introduced into an Erlenmeyer flask charged with ethyl acetate and 10% aqueous ammonia for extraction with ethyl acetate. The organic layer was washed with saturated brine, dried over magnesium sulfate and concentrated in vacuo. The residue thus obtained was purified by silica gel column chromatography (10% to 20% ethyl acetate in n-hexane), thereby giving the titled Compound 29 (278 mg, 89%).

$^1$H NMR (CDCl$_3$) δ: 7.37 (d, J=8.85 Hz, 2H), 7.34 (d, J=8.85 Hz, 2H), 6.80 (t, J=6.18 Hz, 1H), 6.78 (d, J=17.09 Hz, 1H), 6.74 (d, J=16.33 Hz, 1H), 6.52 (s, 1H), 4.56 (d, J=6.10 Hz, 2H), 4.12 (q, J=7.17 Hz, 2H), 1.52 (s, 9H), 0.92 (t, J=7.32 Hz, 3H).

6.3 Production of ethyl (E,E)-4-hydroxy-2-(4-aminostyryl)but-2-enoate (Compound 30)

A THF (2 ml) solution of Compound 29 described above (23 mg, 0.066 mmol) was cooled to 0° C., and 6 N hydrochloric acid (1 ml) was added dropwise. The mixture was stirred at 0° C. for 10 minutes, and then warmed to room temperature and stirred overnight. Saturated aqueous sodium hydrogencarbonate was added to the reaction mixture for neutralization and then extracted using chloroform. The chloroform extract was washed with saturated brine, dried over anhydrous magnesium sulfate, and then concentrated in vacuo. The residue thus obtained was purified by silica gel column chromatography (3% to 10% CHCl$_3$ in MeOH), thereby giving the titled Compound 30 (14 mg, 88%).

$^1$H NMR (CDCl$_3$) δ: 7.60 (d, J=8.54 Hz, 2H), 7.41 (d, J=8.70 Hz, 2H), 6.82 (t, J=6.26 Hz, 3H), 6.81 (d, J=15.72 Hz, 3H), 6.77 (d, J=16.48 Hz, 3H), 4.57 (d, J=6.10 Hz, 2H), 4.28 (q, J=7.12 Hz, 2H), 1.34 (t, J=7.10 Hz, 3H).

ESI-MS m/z: 384.21, [M+Na]$^+$

EXAMPLE 7

Production of ethyl (E,E)-4-hydroxy-2-(4-(7-diethylaminocoumarin-3-carboxamide)styryl)but-2-enoate (Compound 32) (in Formula (II), R$^1$ being —CH$_2$OH, R$^2$ being —C$_2$H$_5$, X$^1$ being a group represented by the formula -L$^1$-A$^1$-, Z being 1,4-phenylene, L$^1$ being a bond, A$^1$ being —NH—, and R$^4$ being as follows)

[Chemical Formula 244]

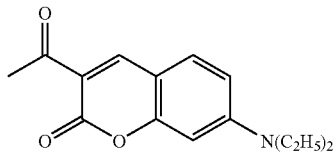

Compound 32 described above was produced according to Scheme 17 below.

Scheme 17

[Chemical Formula 245]

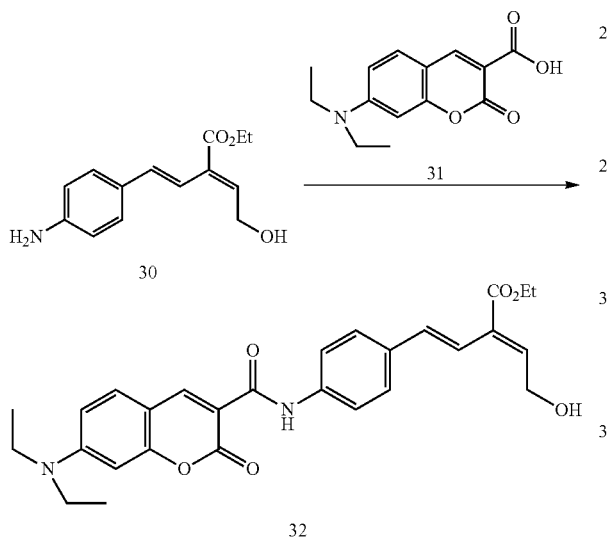

7-Diethylaminocoumarin-3-carboxylic acid succinimidyl ester (coumarin) (Compound 31) (18 mg, 0.68 mmol), EDC (15 mg, 0.078 mmol) and DMAP (9.8 mg, 0.08 mmol) were added to a CH$_2$Cl$_2$ (200 μl) solution of Compound 30 described above (16 mg, 0.065 mmol), and stirred at room temperature for 5 hours. The reaction mixture was purified by preparative thin-layer chromatography (3% CHCl$_3$ in MeOH), thereby giving the titled Compound 32 (10 mg, 32%).

ESI-MS m/z: 491 [M+H]$^+$, 513 [M+Na]$^+$

EXAMPLE 8

Production of ethyl (E,E)-4-hydroxy-2-((4-hexahydro-2-oxo-1H-thieno[3,4-d]imidazole-4-pentanamide)styryl)but-2-enoate (Compound 34) (in Formula (II), R$^1$ being —CH$_2$OH, R$^2$ being —C$_2$H$_5$, X$^1$ being a group represented by the formula -L$^1$-A$^1$-, Z being 1,4-phenylene, L$^1$ being a bond, A$^1$ being —NH—, and R$^4$ being as follows)

[Chemical Formula 246]

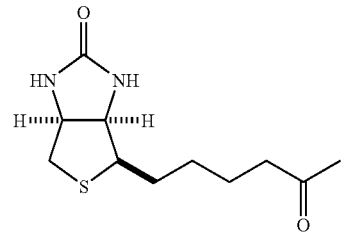

Compound 34 described above was produced according to Scheme 18 below.

Scheme 18

[Chemical Formula 247]

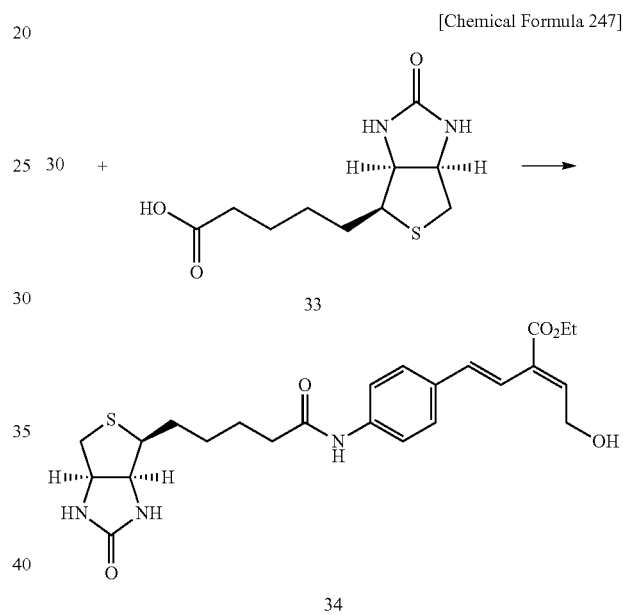

Biotin (Compound 33) (1 mg, 4 μmol), HBTU (1.5 mg, 4 μmol) and triethylamine (0.8 μl, 6 μmol) were added to a DMF (1 ml) solution of Compound 30 described above (1 mg, 4 μmol), and stirred at room temperature for 9 hours. The reaction mixture was purified by preparative thin-layer chromatography (13% CHCl$_3$ in MeOH), thereby giving the titled Compound 34 (1.2 mg, 65%).

ESI-MS m/z: 495.96 [M+Na]$^+$

EXAMPLE 9

Production of ethyl (E,E)-4-hydroxy-2-(4-(6-((4,4-difluoro-5,7-dimethyl-4-bora-3a,4a-diaza-s-indacene-3-propionylamino) dodecanamide)styryl)but-2-enoate (Compound 38) (in Formula (II), R$^1$ being —CH$_2$OH, R$^2$ being —C$_2$H$_5$, X$^1$ being a group represented by the formula -L$^1$-A$^1$-, Z being 1,4-phenylene, L$^1$ being a bond, A$^1$ being —NH—, and R$^4$ being as follows)

137

[Chemical Formula 248]

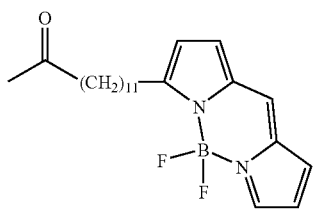

Compound 38 described above was produced according to Scheme 19 below.

Scheme 19

[Chemical Formula 249]

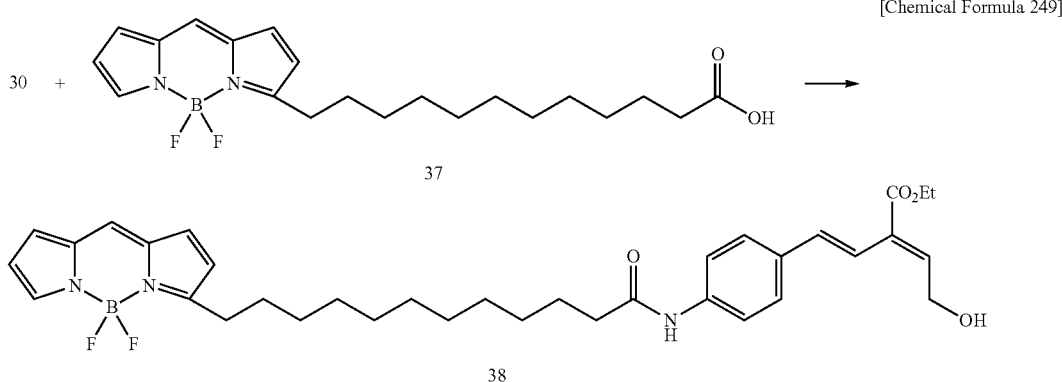

6-((4,4-Difluoro-5,7-dimethyl-4-bora-3a,4a-diaza-s-indacene-3-propionyl)amino)dodecanoic acid (BODIPY) (Compound 37) (0.1 mg, 0.2 µmol), HBTU (0.1 mg, 0.2 µmol) and triethylamine (0.05 µl, 0.3 µmol) were added to a DMF solution of Compound 30 described above (0.06 mg, 0.2 µmol), and stirred at room temperature for 10 hours. The reaction mixture was purified by preparative thin-layer chromatography (6% CHCl$_3$ in MeOH), thereby giving the titled Compound 36.

ESI-MS m/z: 656.39 [M+Na]$^+$

138

EXAMPLE 10

Production of ethyl (E,E)-4-hydroxy-2-(4-(2-(6-(N-(7-nitrobenz-2-oxa-1,3-diazol-4-yl)amino)hexanamide)styryl)but-2-enoate (Compound 36) (in Formula (II), $R^1$ being —CH$_2$H$_5$, $R^2$ being —C$_2$H$_5$, $X^1$ being a group represented by the formula -L$^1$-A$^1$-, Z being 1,4-phenylene, L$^1$ being a bond, A$^1$ being —NH—, and $R^4$ being as follows)

[Chemical Formula 250]

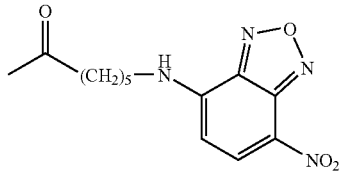

Compound 36 described above was produced according to Scheme 20 below.

Scheme 20

[Chemical Formula 251]

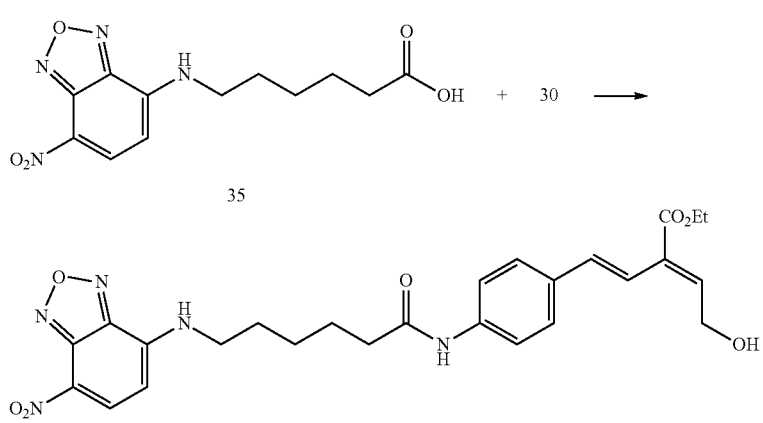

6-(N-(7-nitrobenz-2-oxa-1,3-diazol-4-yl)amino)hexanoic acid (Compound 35), (1.2 mg, 4 μmol), HBTU (1.5 mg, 4 μmol) and triethylamine (0.8 μl, 6 μmol) were added to a DMF (1 ml) solution of Compound 30 described above (1 mg, 4 μmol), and stirred at room temperature for 9 hours. The reaction mixture was purified by preparative thin-layer chromatography (6% $CHCl_3$ in MeOH), thereby giving the titled Compound 36 (0.2 mg, 10%).

ESI-MS m/z: 546.17 $[M+Na]^+$

EXAMPLE 11

Production of ethyl (E,E)-4-oxo-2-(4-(2-(6-(N-(7-nitrobenz-2-oxa-1,3-diazol-4-yl)amino)hexanamide)styryl) but-2-enoate (Compound 39) (in Formula (II), $R^1$ being —CHO, $R^2$ being —$C_2H_5$, $X^1$ being a group represented by the formula -$L^1$-$A^1$-, Z being 1,4-phenylene, $L^1$ being a bond, $A^1$ being —NH—, and $R^4$ being as follows)

[Chemical Formula 252]

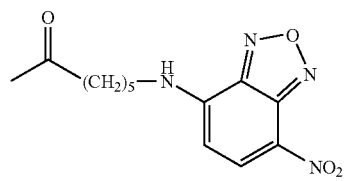

Compound 39 described above was produced according to Scheme 21 below.

Scheme 21

[Chemical Formula 253]

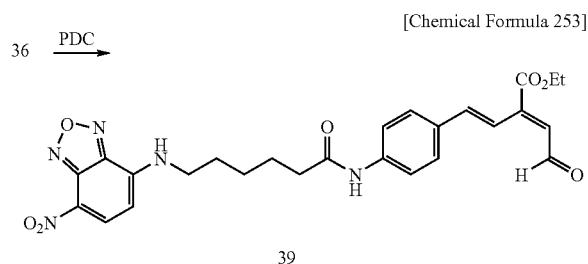

PDC (1 mg, 2.7 μmol) was added to a $CH_2Cl_2$ solution of Compound 36 described above (0.1 mg, 0.2 μmol, and stirred at room temperature for 10 minutes. The reaction mix was purified by silica gel chromatography (6% $CHCl_3$ in MeOH), thereby giving the titled Compound 39.

EXAMPLE 12

Production of 2-(2-N-tert-butoxycarbonylaminoethoxy) ethyl (E,E)-4-(tert-butyldiphenylsilyloxy)-2-styrylbut-2-enoate (Compound 45) (in Formula (I), $R^1$ being —$CH_2$OTBDPS, $R^2$ being —$C_2H_5$, $X^1$ being a group represented by the formula -$L^1$-$A^1$-, Z being 1,4-phenylene, $L^1$ being a bond, $A^1$ being —NH—, and $R^4$ being H)

Compound 45 described above was produced according to Scheme 22 below.

Scheme 22

[Chemical Formula 254]

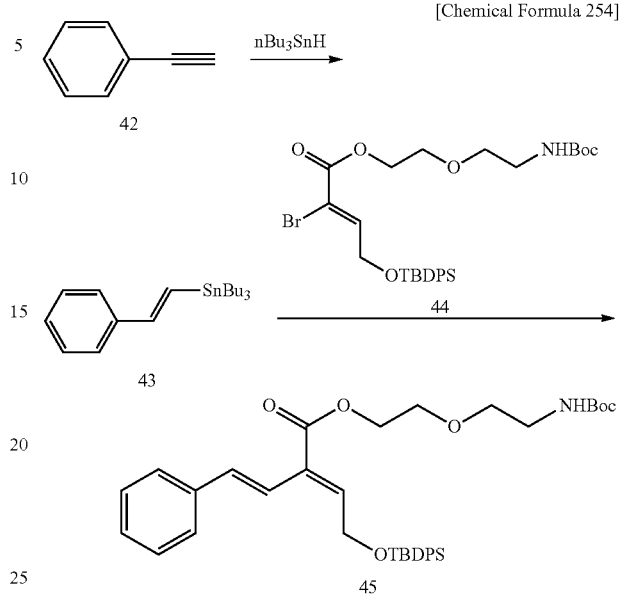

12.1 Production of (E)-β-styryltributyltin (Compound 43)

AIBN (19 mg, 0.118 mmol) and $Bu_3SnH$ (1 ml, 3.82 mmol) were added at room temperature to a benzene (6 ml) solution of phenylacetylene (Compound 42) (300 mg, 2.94 mmol). This mix was heated to 90° C., stirred for 40 minutes, and then concentrated in vacuo. The residue thus obtained was purified by alumina column chromatography (n-hexane), thereby giving the titled Compound 43 (989 mg, 86%).

$^1$H NMR (500 M, $CDCl_3$) δ ppm: 7.41 (d, J=7.5 Hz, 2H), 7.31 (t, J=7.5 Hz, 2H), 7.22 (t, J=6 Hz, 1H), 6.88 (d, J=19.5 Hz, 1H), 6.84 (d, J=19.5 Hz, 1H), 1.55 (m, J=7.5 Hz, 6H), 1.34 (m, J=7 Hz, 6H), 0.972 (t, J=6 Hz, 6H), 0.904 (t, J=6 Hz, 9H).

12.2 Production of 2-(2-N-tert-butoxycarbonylaminoethoxy)ethyl (E,E)-4-oxo-2-styrylbut-2-enoate (Compound 45)

$Pd_2(dba)_3$ (9.0 mg, 0.01 mmol) and P(2-furyl)$_3$ (9.1 mg, 0.04 mmol) were added to a DMF (1 ml) solvent and stirred at room temperature for 10 minutes. ADMF (3 ml) solution of Compound 43 described above (232 mg, 0.591 mmol) and 2-(2-N-tert-butoxycarbonylaminoethoxy)ethyl (Z)-2-bromo-4-(tert-butyldiphenylsilanyloxy)-2-butenoate (Compound 44) (300 mg, 0.492 mmol) was added to the mixture dropwise at room temperature, and then LiCl (42 mg, 0.985 mmol) was added. The reaction mixture was heated to 115° C., stirred for 30 minutes, and introduced into an Erlenmeyer flask charged with ethyl acetate and 10% aqueous ammonia for extraction with ethyl acetate. The organic layer thus obtained was washed with saturated brine, dried over magnesium sulfate, and then concentrated in vacuo. The residue thus obtained was purified by silica gel chromatography (n-hexane:EtOAc=9:1 to 1:1), thereby giving the titled Compound 45 (223 mg, 72%).

$^1$H NMR (500 MHz, $CDCl_3$) δ ppm: 7.66 (m, 4H), 7.55 (s, 1H), 7.45-7.20 (m, 11H), 6.85 (t, J=6 Hz, 1H), 6.66 (d, J=16.3

Hz, 1H), 6.56 (d, J=16.3 Hz, 1H), 4.54 (d, J=6 Hz, 2H), 4.35 (t, J=5 Hz, 1H), 3.73 (t, J=5 Hz, 2H), 3.55 (t, J=5 Hz, 2H), 3.31 (d, J=5 Hz, 2H), 1.52 (s, 9H), 1.43 (s, 9H), 1.08 (s, 9H).

EXAMPLE 13

Production of 2-(2-(7-diethylaminocoumarin)-3-carbonylaminoethoxy)ethyl (E,E)-4-hydroxy-2-styrylbut-2-enoate (Compound 49) (in Formula (III), $R^1$ being —$CH_2OH$, $R^8$ being H, $X^2$ being a group represented by the formula -$L^2$-$A^2$-$L^3$-, Z being 1,4-phenylene, $L^2$ being —$(CH_2)_2$—O—$(CH_2)_2$—, $A^2$ being —NH—, $L^3$ being a bond, and $R^5$ being as follows)

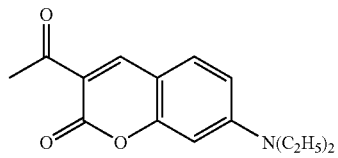

Compound 49 described above was produced according to Scheme 23 below.

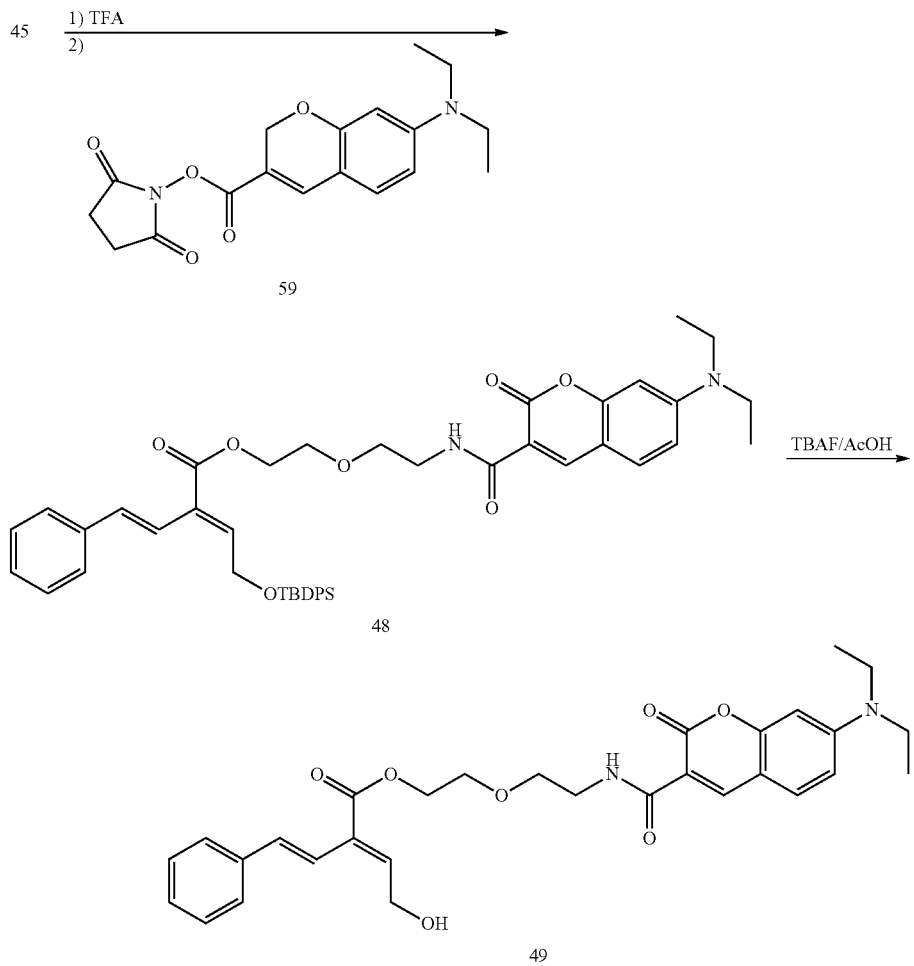

13.1 Production of 2-(2-(7-diethylaminocoumarin)-3-carbonylaminoethoxy)ethyl (E,E)-4-(tert-butyl-diphenylsilanyloxy)-2-styrylbut-2-enoate (Compound 48)

TFA (145 μl) was added to a $CH_2Cl_2$ (0.6 ml) solution of Compound 45 above (5.3 mg, 8.37 μmol) and stirred at 0° C. for 20 minutes. The reaction solution was neutralized with aqueous 1 N NaOH and then extracted with ethyl acetate. The organic layer thus obtained was dried over magnesium sulfate and concentrated in vacuo. No purification was performed, and the residue thus obtained was dissolved in anhydrous $CH_2Cl_2$ (1 ml) under an Ar atmosphere. 7-Diethylaminocoumarin-3-carboxylic acid succinimidyl ester (Compound 59) (2.1 mg, 586 µmol) was added to the solution, and stirred at room temperature for 1 hour. The reaction solution was concentrated, and the residue was purified by silica gel chromatography (n-hexane:EtOAc=9:1 to 1:1), thereby giving the titled Compound 48 (4.0 mg, 62%, in 2 steps).

ESI-MS (positive) m/z: 773.7 [M+H]$^+$.

13.2 Production of 2-(2-(7-diethylaminocoumarin)-3-carbonylaminoethoxy)ethyl (E,E)-4-hydroxy-2-styrylbut-2-enoate (Compound 49)

A 1 M TBAF solution (2.59 µl) in THF and a 1 M acetic acid solution (2.49 µl) in THF were added to a THF (500 µl) solution of Compound 48 described above (2.0 mg, 2.59 µmol at 0° C., and stirred for 2 hours. The reaction mixture was extracted with CHCl$_3$. The organic layer thus obtained was dried over magnesium sulfate and concentrated in vacuo, and the residue thus obtained was purified by preparative thin-film silica gel chromatography (CHCl$_3$:MeOH=15:1), thereby giving the titled Compound 49 (0.5 mg, 36%).

ESI-MS (positive) m/z: 535.3 [M+H]$^+$

EXAMPLE 14

Production of 2-(2-(7-diethylaminocoumarin)-3-carbonylaminoethoxy)ethyl (E,E)-4-oxo-2-styrylbut-2-enoate (Compound 50) (in Formula (III), R$^1$ being —CHO, R$^3$ being H, X$^2$ being a group represented by the formula -L$^2$-A$^2$-L$^3$-, Z being 1,4-phenylene, L$^2$ being —(CH$_2$)$_2$—O—(CH$_2$)$_2$—, A$^2$ being —NH—, L$^3$ being a bond, and R$^5$ being as follows)

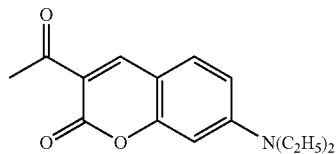

Compound 50 described above was produced according to Scheme 24 below.

Scheme 24

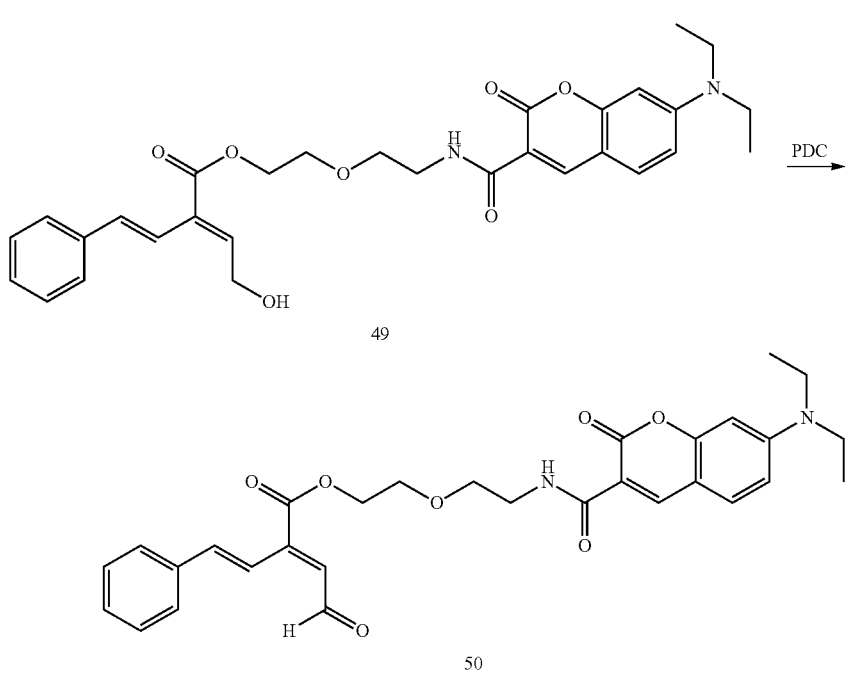

PDC (2 mg, 5.32 µmol) was added to a CH$_2$Cl$_2$ (200 µl) solution of Compound 49 described above (0.2 mg, 0.374 µmol) and stirred for 10 minutes. The reaction solution was subjected to silica gel chromatography (CHCl$_3$:MeOH=90:1 to 70:1) for purification, thereby giving the titled Compound 50 (140 µg, 70%).

ESI-MS (positive) m/z: 533.2 [M+H]$^+$

EXAMPLE 15

Production of 2-(2-N-tert-butoxycarbonylaminoethoxy) ethyl (E,E)-4-(tert-butyldiphenylsilanyloxy)-2-(4-N-tert-butoxycarbonylaminostryryl)but-2-enoate (Compound 46) (R$^1$ being —CH$_2$OTBDPS, R$^2$ being a group represented by the formula -L$^2$-A$^2$-M$^2$, R$^3$ being a group represented by the formula -L$^1$-A$^1$-M$^1$, Z being 1,4-phenylene, L$^1$ being a bond, A$^1$ being —NH—, M$^1$ being BOC, L$^2$ being —(CH$_2$)$_2$—O—(CH$_2$)$_2$—, A$^2$ being —NH—, and M$^2$ being BOC in Formula (I))

Compound 46 described above was produced according to Scheme 25 below.

Scheme 25

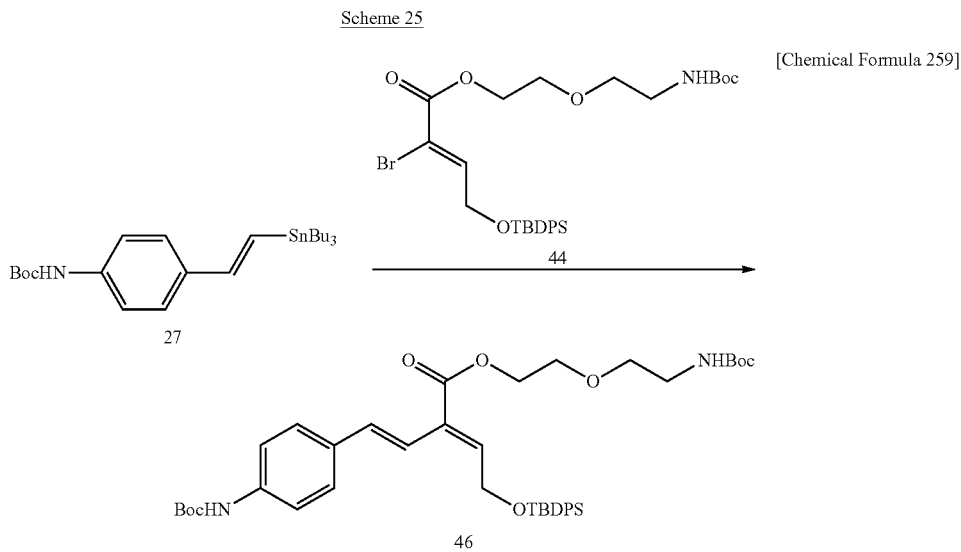

[Chemical Formula 259]

Pd$_2$(dba)$_3$ (2.1 mg, 0.003 mmol) and P(2-furyl)$_3$ (2.1 mg, 0.012 mmol were added to a DMF (1 ml) solvent and stirred at room temperature for 15 minutes. A DMF (3 ml) solution of (E)-tert-butyl-4-(2-(tri-n-butylstannyl)vinyl)phenylcarbamate (Compound 27) (80 mg, 0.158 mmol and Compound 44 described above (80 mg, 0.132 mmol) was added to the mixture dropwise at room temperature, and then LiCl (11 mg, 0.263 mmol) was added. The reaction mixture was heated to 115° C., stirred for 30 minutes, introduced into an Erlenmeyer flask charged with ethyl acetate and 10% aqueous ammonia for extraction with ethyl acetate. The organic layer thus obtained was washed with saturated brine, dried over magnesium sulfate, and then concentrated in vacuo. The residue thus obtained was purified by silica gel chromatography (n-hexane:EtOAc=9:1 to 1:1), thereby giving the titled Compound 46 (42 mg, 41%).

$^1$H NMR (500 MHz, CDCl$_3$) δ ppm: 7.68 (m, 4H), 7.45-7.10 (m, 11H), 6.89 (t, J=6 Hz, 1H), 6.72 (d, J=16.3 Hz, 1H), 6.66 (d, J=16.3 Hz, 1H), 4.56 (d, J=6 Hz, 2H), 4.36 (t, J=5 Hz, 1H), 3.74 (t, J=5 Hz, 2H), 3.56 (t, J=5 Hz, 2H), 3.31 (d, J=5 Hz, 2H), 1.43 (s, 9H), 1.07 (s, 9H).

EXAMPLE 16

Production of 2-(2-(7-diethylaminocoumarin)-3-carbonylaminoethoxy)ethyl (E,E)-4-(tert-butyldiphenylsilanyloxy)-2-(4-aminostyryl)but-2-enoate (Compound 51) ($R^1$ being —CH$_2$OTBDPS, $R^3$ being —NH$_2$, $R^5$ being as follows:

[Chemical Formula 260]

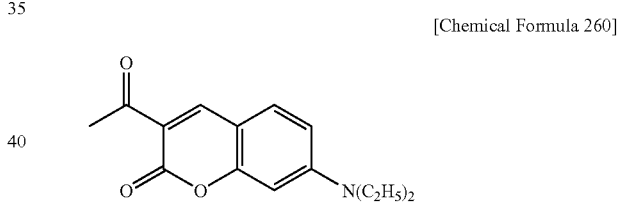

Z being 1,4-phenylene, $X^2$ being -$L^2$-$A^2$-$L^3$-, $L^2$ being —(CH$_2$)$_2$—O—(CH$_2$)$_2$—, $A^2$ being —NH—, and $L^3$ being a bond in Formula (III))

Compound 51 described above was produced according to Scheme 26 below.

Scheme 26

[Chemical Formula 261]

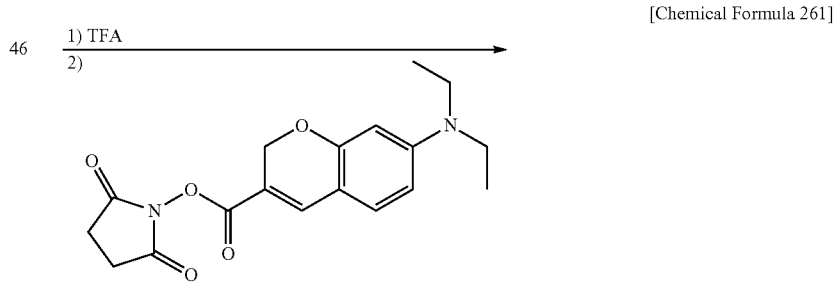

-continued

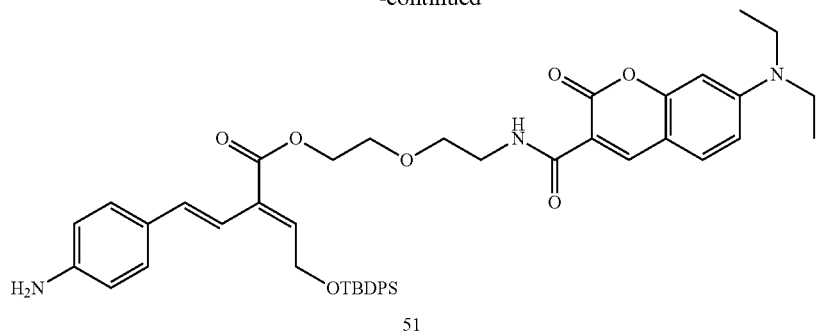

51

TFA (145 μl) was added to a CH$_2$Cl$_2$ (0.6 ml) solution of Compound 46 described above (6.2 mg, 8.37 μmol) and stirred at 0° C. for 20 minutes. This mixture was neutralized with aqueous 1 N NaOH and then extracted with ethyl acetate. The organic layer thus obtained was dried over magnesium sulfate and concentrated in vacuo. No purification was performed, and the residue thus obtained was dissolved in anhydrous CH$_2$Cl$_2$ (1 ml). Compound 59 (2.1 mg, 5.86 μmol) was added to this solution under an Ar atmosphere, and stirred at room temperature for 1 hour. The reaction solution was concentrated and the residue thus obtained was purified by silica gel chromatography (10% to 50% ethyl acetate in n-hexane), thereby giving the titled Compound 51 (4.0 mg, 62%, in 2 steps).

ESI-MS (positive) m/z: 788.5 [M+H]$^+$

EXAMPLE 17

Production of 2-(2-(7-diethylaminocoumarin)-3-carbonylaminoethoxy)ethyl (E,E)-4-(tert-butyldiphenylsilanyloxy)-2-((4-hexahydro-2-oxo-1H-thieno[3,4-d]imidazole-4-pentanamide)styryl)but-2-enoate (Compound 52) (R$^1$ being —CH$_2$OTBDPS, R$^4$ being as follows:

[Chemical Formula 262]

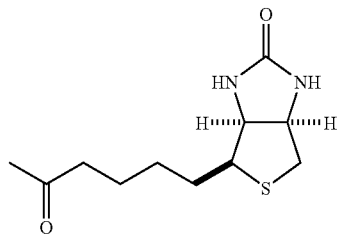

R$^5$ being as follows:

[Chemical Formula 263]

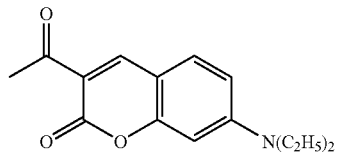

Z being 1,4-phenylene, X$^1$ being -L$^1$-A$^1$-, X$^2$ being -L$^2$-A$^2$-L$^3$-, L$^1$ being a bond, A$^1$ being —NH—, L$^2$ being —(CH$_2$)$_2$—O—(CH$_2$)$_2$—, A$^2$ being —NH—, and L$^3$ being a bond in Formula (IV))

Compound 52 described above was produced according to Scheme 27 below.

Scheme 27

[Chemical Formula 264]

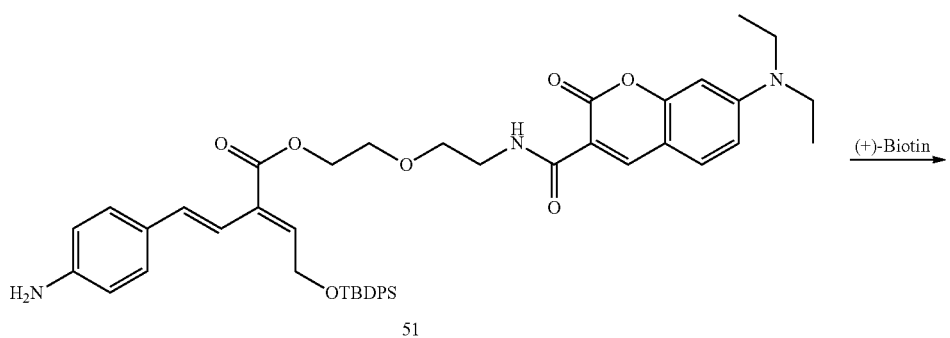

51

(+)-Biotin →

-continued

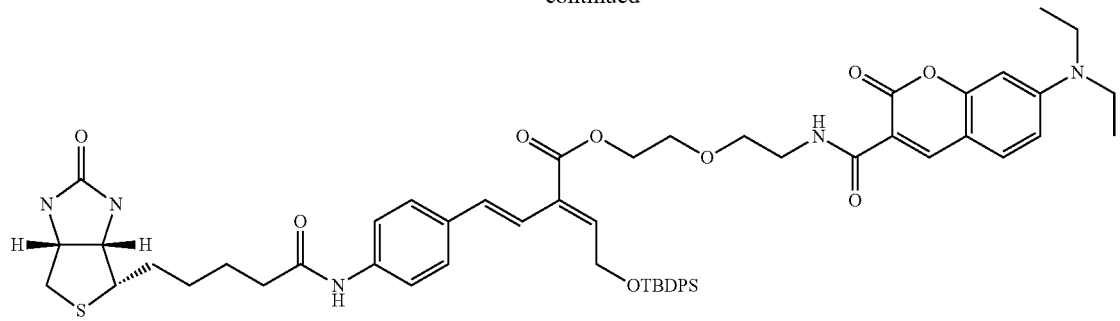

52

HBTU (3.54 mg, 9.33 μmol) and biotin (Compound 33) (1.82 mg, 7.46 μmol) were added to an anhydrous DMF (1 ml) solution of Compound 51 described above (4.9 mg, 6.21 μmol) under an Ar atmosphere, and stirred at room temperature for 20 minutes. Thereafter, triethylamine (1.73 μl, 12.4 μmol) was added to the mixture and stirred overnight. After concentrating the reaction solution in vacuo, the residue thus obtained was purified by preparative thin-layer silica gel chromatography (CHCl$_3$:MeOH=7:1), thereby giving the titled Compound 52 (4.1 mg, 65%).

ESI-MS (positive) m/z: 1014.4 [M+H]$^+$

EXAMPLE 18

Production of 2-(2-(7-diethylaminocoumarin)-3-carbonylaminoethoxy)ethyl (E,E)-4-hydroxy-2-((4-hexahydro-2-oxo-1H-thieno[3,4-d]imidazole-4-pentanamide)styryl)but-2-enoate (Compound 53) (R$^1$ being —CH$_2$OH, R$^4$ being as follows:

[Chemical Formula 265]

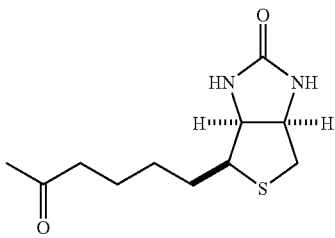

R$^5$ being as follows:

[Chemical Formula 266]

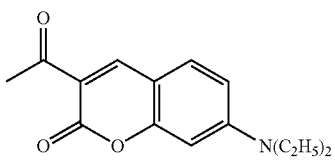

Z being 1,4-phenylene, X$^1$ being -L$^1$-A$^1$-, X$^2$ being -L$^2$-A$^2$-L$^3$-, L$^1$ being a bond, A$^1$ being —NH—, L$^2$ being —(CH$_2$)$_2$—O—(CH$_2$)$_2$—, A$^2$ being —NH—, and L$^3$ being a bond in Formula (IV))

Compound 53 described above was produced according to Scheme 28 below.

Scheme 28

[Chemical Formula 267]

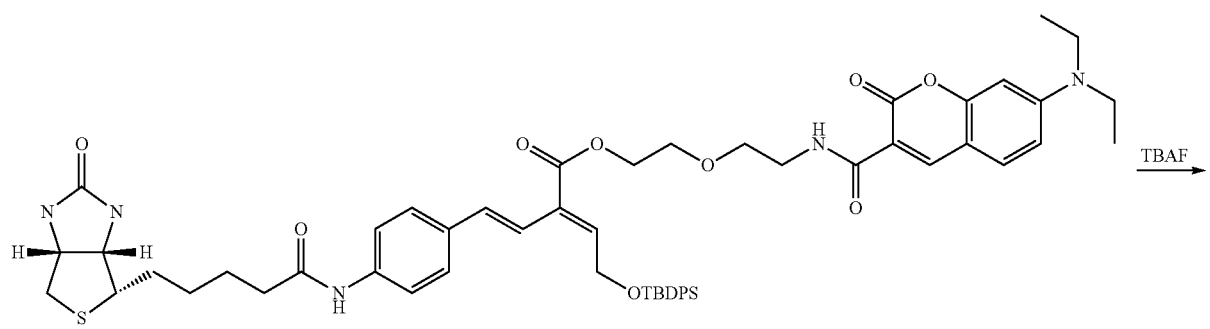

52

TBAF

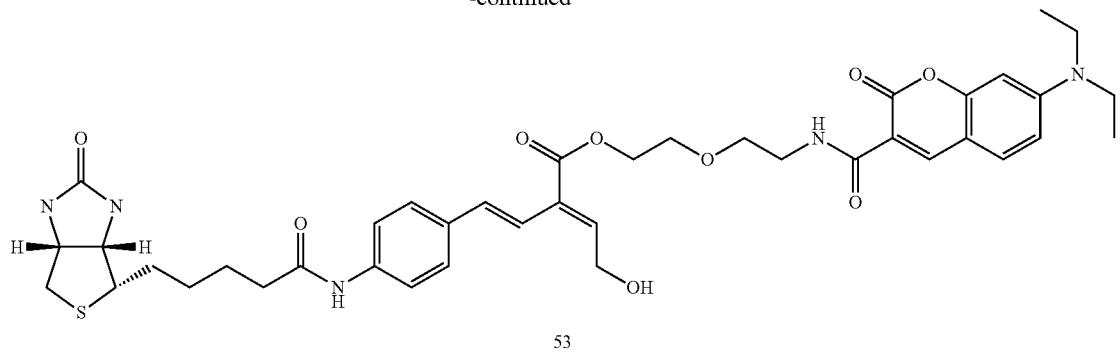

53

A 1 M TBAF solution (2.59 μl) in THF and an 1 M acetic acid solution (2.49 μl) in THF were added to a THF (1 ml) solution of Compound 52 described above (4.1 mg, 4.04 μmol) at room temperature, and stirred for 2 hours. The reaction mixture was extracted with $CHCl_3$. The organic layer thus obtained was dried over magnesium sulfate and concentrated in vacuo. The residue thus obtained was purified by preparative thin-layer silica gel chromatography ($CHCl_3$: MeOH=10:1), thereby giving the titled Compound 53 (0.5 mg, 16%).

ESI-MS (positive) m/z: 776.5 $[M+H]^+$

EXAMPLE 19

Production of 2-(2-(7-diethylaminocoumarin)-3-carbonylaminoethoxy)ethyl (E,E)-4-(tert-butyldiphenylsilanyloxy)-

[Chemical Formula 269]

Z being 1,4-phenylene, $X^1$ being $-L^1-A^1-$, $X^2$ being $-L^2-A^2-L^3-$, $L^1$ being a bond, $A^1$ being —NH—, $L^2$ being —$(CH_2)_2$—O—$(CH_2)_2$—, $A^2$ being —NH—, and $L^3$ being a bond in Formula (IV))

Compound 54 described above was produced according to Scheme 29 below.

Scheme 29

51 →(NBD-X)→

[Chemical Formula 270]

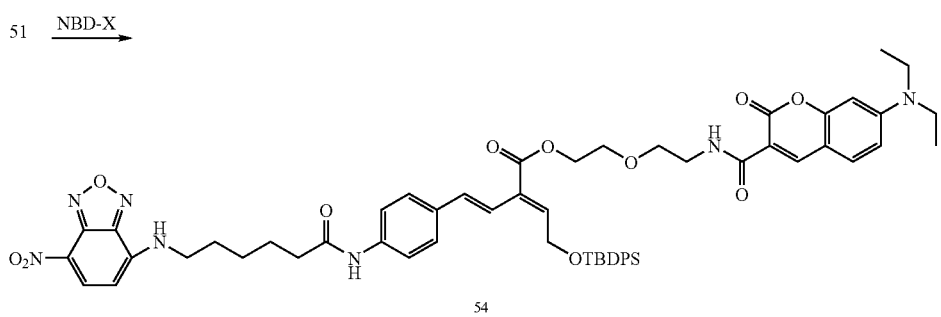

54

2-((6-(N-(7-nitrobenz-2-oxa-1,3-diazol-4-yl)amino)hexanamide) styryl)but-2-enoate (Compound 54) ($R^1$ being —$CH_2OTBDPS$, $R^4$ being as follows:

[Chemical Formula 268]

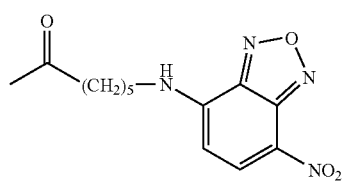

$R^5$ being as follows:

HBTU (1.80 mg, 4.76 μmol) and 6-(N-(7-nitrobenz-1,3-diazol-4-yl)amino)hexanoic acid (NBD-X) (1.12 mg, 3.81 μmol) were added to an anhydrous DMF (1 ml) solution of Compound 51 described above (2.5 mg, 3.71 μmol) under an Ar atmosphere, and stirred at room temperature for 20 minutes. Thereafter, triethylamine (0.88 μl, 6.35 μmol) was added and stirred overnight. After concentrating the reaction solution in vacuo, the residue thus obtained was purified by preparative thin-layer silica gel chromatography ($CHCl_3$: MeOH=20:1), thereby giving the titled Compound 54 (1.3 mg, 39%).

ESI-MS (positive) m/z: 1064.6 $[M+H]^+$

EXAMPLE 20

Production of 2-(2-(7-diethylaminocoumarin)-3-carbonylaminoethoxy)ethyl (E,E)-4-hydroxy-2-((6-N-(7-nitrobenz- 2-oxa-1,3-diazol-4-yl)amino)hexanamide)styryl)but-2-enoate (Compound 55) (R¹ being —CHOH, R⁴ being as follows:

[Chemical Formula 271]

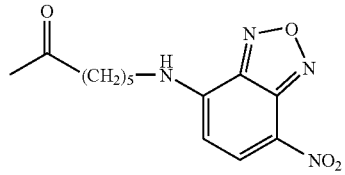

R⁵ being as follows:

[Chemical Formula 272]

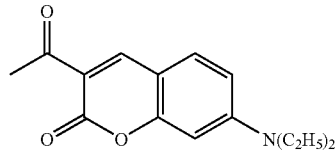

Z being 1,4-phenylene, X¹ being -L¹-A¹-, X² being -L²-A²-L³-, L¹ being a bond, A¹ being —NH—, L² being —(CH₂₂—O—(CH₂)₂—, A² being —NH—, and L³ being a bond in Formula (IV))

Compound 55 described above was produced according to Scheme 30 below.

A 1 M TBAF solution (1.22 µl) in THF and a 1 M acetic acid solution (1.17 µl) in THF were added to a THF (500 µl) solution of Compound 54 described above (1.3 mg, 1.22 µmol) at 0° C., and stirred for 2 hours. The reaction mixture was extracted with CHCl₃. The organic layer thus obtained was dried over magnesium sulfate and concentrated in vacuo. The residue thus obtained was purified by preparative thin-layer silica gel chromatography (CHCl₃:MeOH=15:1), thereby giving the titled Compound 55 (1.2 mg, 90%).

ESI-MS (positive) m/z: 826.4 [M+H]⁺

EXAMPLE 21

Production of 2-(2-(7-diethylaminocoumarin)-3-carbonylaminoethoxy)ethyl (E,E)-4-oxo-2-((6-(N-(7-nitrobenz-2-oxa-1,3-diazol-4-yl)amino)hexanamide)styryl)but-2-enoate (Compound 56) (R¹ being —CHO, R⁴ being as follows:

[Chemical Formula 274]

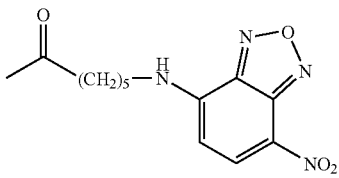

R⁵ being as follows:

Scheme 30

[Chemical Formula 273]

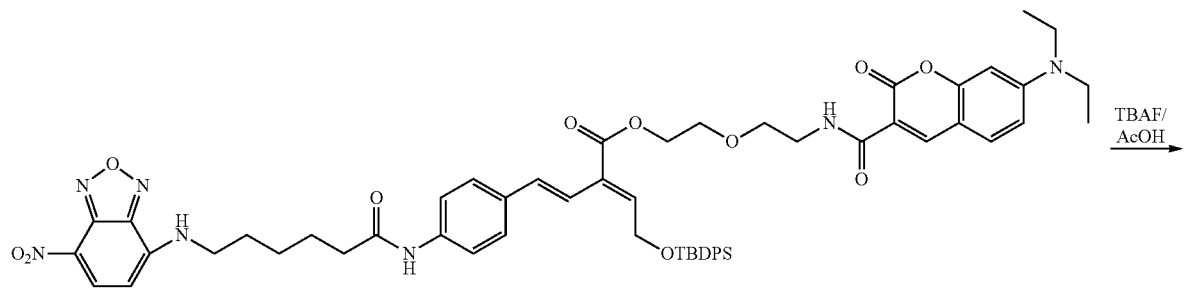

54

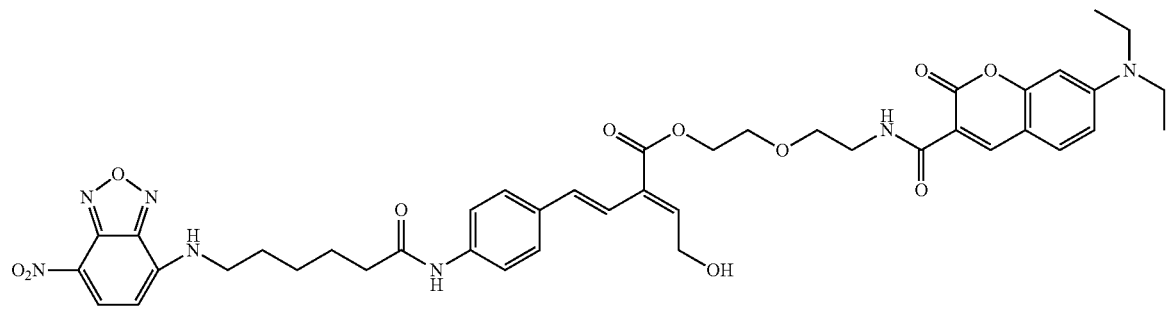

55

[Chemical Formula 275] lp;2p

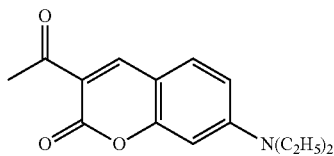

Z being 1,4-phenylene, $X^1$ being $L^1$-$A^1$-, $X^2$ being -$L^2$-$A^2$-$L^3$-, $L^1$ being a bond, $A^1$ being —NH—, $L^2$ being —(CH$_2$)$_2$—O—(CH$_2$)$_2$—, $A^2$ being —NH—, and $L^3$ being a bond in Formula (IV))

Compound 56 described above was produced according to Scheme 31 below.

[Chemical Formula 277]

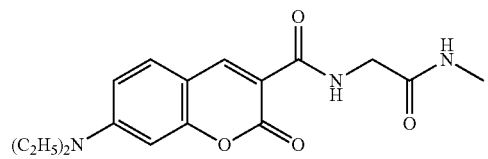

and Z being a 1,4-phenylene group in Formula (II))

Scheme 31

[Chemical Formula 276]

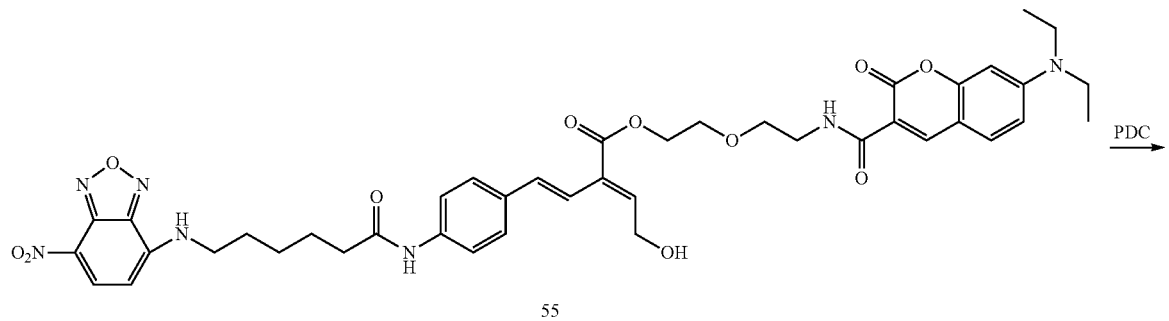

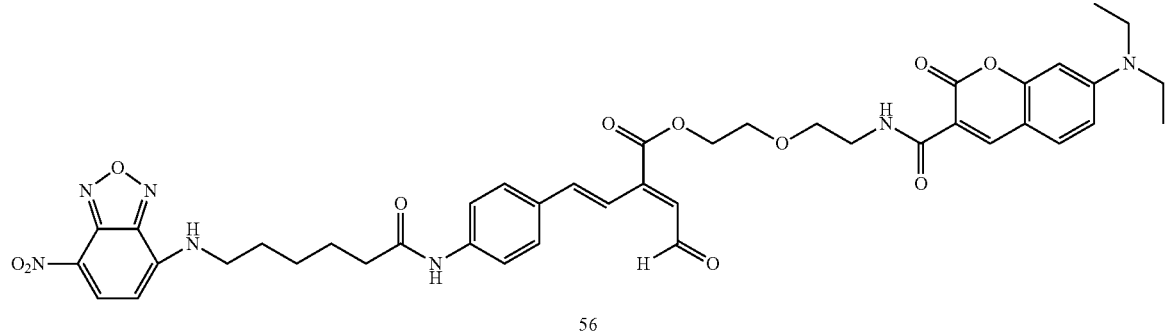

PDC (2 mg, 5.32 μmol) was added to a CH$_2$Cl$_2$ (200 μl) solution of Compound 55 described above (0.9 mg, 1.09 μmol), and stirred for 10 minutes. The reaction solution was subjected as-is to silica gel chromatography (1% to 1.5% MeOH in CHCl$_3$) for purification, thereby giving the titled Compound 56 (630 μg, 70%).

ESI-MS (positive) m/z: 824.3 [M+H]$^+$

EXAMPLE 22

Production of ethyl (E,E)-4-hydroxy-2-(4-(2-(7-diethylaminocoumarin-3-carboxamido)acetamide)styryl)but-2-enoate (Compound 17) ($R^1$ being a group represented by —CH$_2$OH, $R^2$ being an ethyl group, $R^4$—$X^1$— being a group represented by the formula:

Compound 17 described above was produced according to Scheme 32 below.

Scheme 32

[Chemical Formula 278]

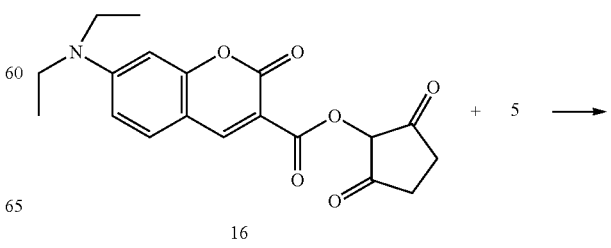

157

-continued

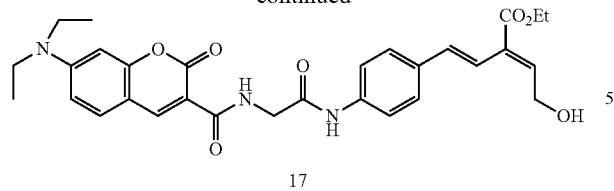

17

Coumarin-OSu (Compound 16) (0.23 mg, 0.65 μmol) was added to a $CH_2Cl_2$ (200 μl) solution of Compound 5 described above (0.2 mg, 0.65 μmol), and stirred at room temperature for 1 hour. The reaction mixture was purified by preparative thin-layer chromatography, thereby giving the titled Compound 17 (0.24 mg, 68%).

ESI-MS m/z: 548.37 $[M+H]^+$

EXAMPLE 23

Production of ethyl (E,E)-4-oxo-2-(4-(2-(7-diethylaminocoumarin-3-carboxamido)acetamide)styryl)but-2-enoate (Compound 18) ($R^1$ being a group represented by —CHO,

158

$R^2$ being an ethyl group, $R^4$—$X^1$— being a group represented by the formula:

[Chemical Formula 279]

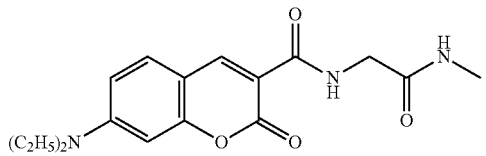

and Z being a 1,4-phenylene group in Formula (II))

Compound 17 described above was produced according to Scheme 33 below.

Scheme 33

[Chemical Formula 280]

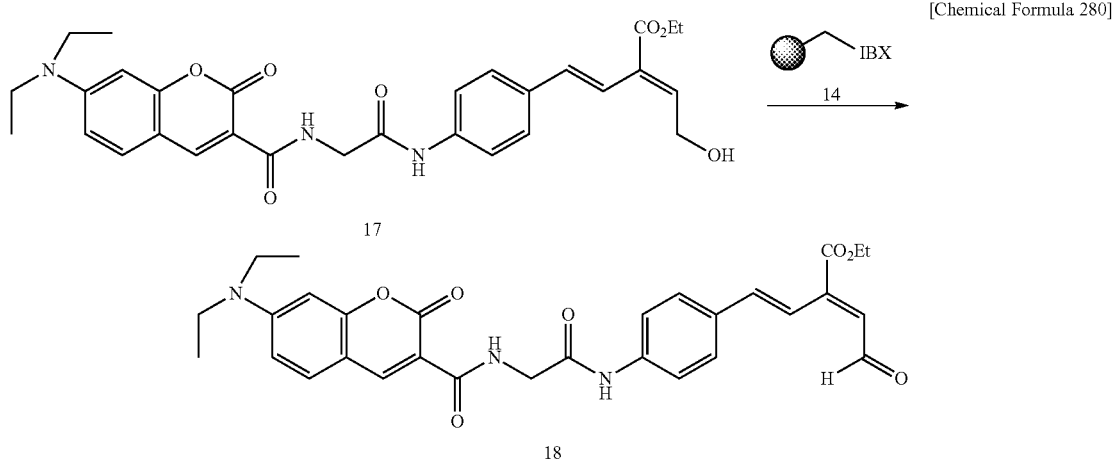

IBX-resin (Compound 14) (0.97 mg, 0.87 mmol) was added to a mixed DMF (50 μl) and $CH_2Cl_2$ (50 μl) solution of Compound 17 described above (0.5 mg, 0.60 μmol), and gently stirred at room temperature for 1 hour. The reaction mixture was filtered and the $CH_2Cl_2$ of the filtrate was concentrated in vacuo, thereby giving a DMF solution of the titled Compound 18.

ESI-MS m/z: 546.31 $[M+H]^+$

EXAMPLE 24

Molecular Labeling with a Compound Represented by Formula (II)

The labeling of somatostatin was investigated using Compound 7 produced in Example 2. See Scheme 34 below for the method for this labeling.

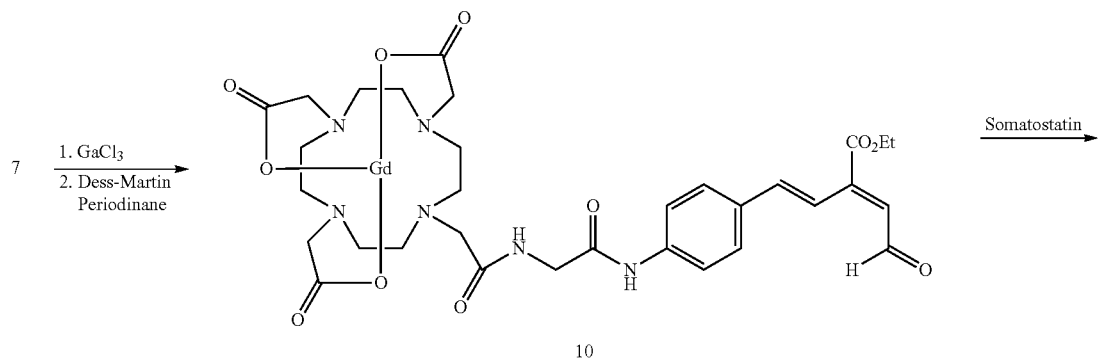

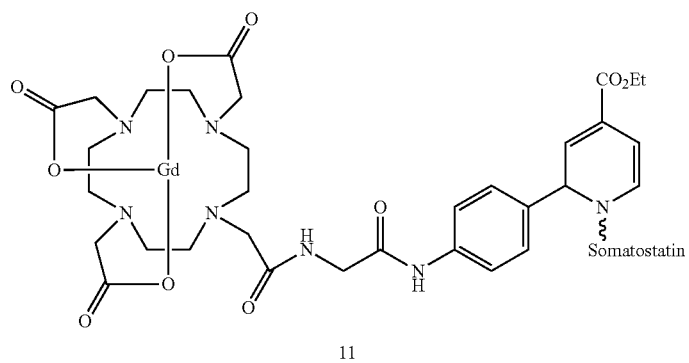

22.1 Production of Gadolinium (β)-10-(2-(2-(4-((1E, 3E)-3-ethoxycarbonyl-5-oxopenta-1,3-dienyl)-phenyl)-2-oxoethylamino)-2-oxoethyl)-1,4,7,10-tetraazacyclododecane-1,4,7-triacetate (Compound 10)

A 0.1 M $GdCl_3$ solution was added to a distilled water (0.1 ml) solution of Compound 7 produced in Example 2 (0.5 mg, 0.72 μmol), and then stirred for 1 minute and concentrated in vacuo. The residue thus obtained was dissolved in a mixed solvent of DMF (0.03 ml) and $CH_2Cl_2$ (0.1 ml), and a Dess-Martin periodinane reagent (0.6 mg, 1.4 μmol) was added to the solution thus obtained and then stirred at room temperature for 20 minutes. The reaction mixture was purified by gel filtration using LH20 ($CHCl_3$:MeOH:$H_2O$=1:1:0.1), thereby giving a DMF solution of the titled Compound 10 (25 μl)
ESI-MS m/z: 844.15, [M+H]$^+$.

22.2 Production of Gd-DOTA-2-amino-6-(2-(4-(2-aminoacetamido)phenyl)-4-(ethoxycarbonyl)-ε-N-pyridin-1(2H)-yl)-lysine-somatostatin (Compound 11)

Somatostatin (0.032 mg, 19 nmol) was dissolved in Otsuka distilled water (28 μl); a DMF solution (25 μl) of Compound 10 described above (0.59 μmol) was added to this solution; and the solution was put into a vortex generator. The reaction mixture was left to stand at room temperature for 30 minutes and then lyophilized, thereby giving the titled Compound 11.
MALDI-TOF-MS m/z: 2475.7 [M+H]$^+$

EXAMPLE 25

Molecular Labeling with a Compound Represented by Formula (II)

The labeling of human serum albumin (HSA) was investigated using Compound 8 produced in Example 3. See Scheme 35 below for the method for this labeling.

[Chemical Formula 282]

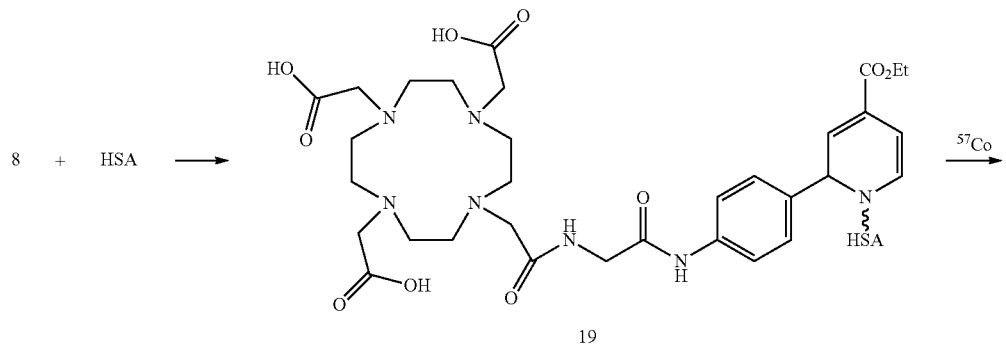

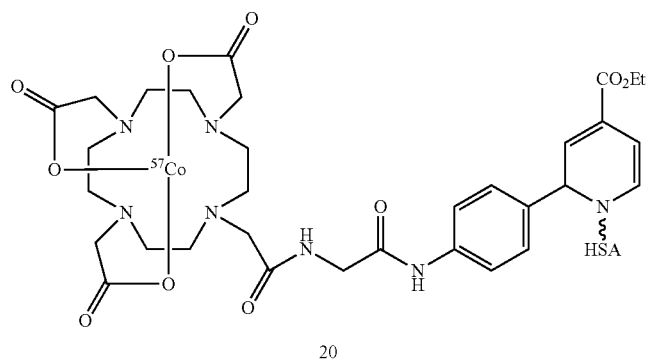

23.1 Production of DOTA-2-amino-6-(2-(4-(2-aminoacetamido)phenyl)-4-(ethoxycarbonyl)-ε-N-pyridin-1(2H)-yl)-lysine-HSA (Compound 19) and $^{57}$Co-DOTA-2-amino-6-(2-(4-(2-aminoacetamido)phenyl)-4-(ethoxycarbonyl)-ε-N-pyridin-1(2H)-yl)-lysine-HSA (Compound 20)

HSA (0.5 mg, 7.5 nmol was dissolved in a PBS buffer solution (1.5 ml) to prepare a 5 μM HSA solution. 320 μl (1.6 nmol) of the HSA solution was introduced into each of 3 Eppendorf tubes. 1.2 μl (40 nmol), 2.3 μl (80 nmol) and 11.8 μl (0.4 μmol) of a DMF solution (3.38×10$^{-2}$M) of Compound 8 described above were added to the respective Eppendorf tubes. 160 μl (0.8 nmol) of the 5 μM HSA solution was added to each of the Eppendorf tubes, and 11.8 μl (0.4 μmol) of a DMF solution (3.38×10$^{-2}$M) of Compound 8 described above was added to each tube. The reaction mixtures all were left to stand at room temperature for 30 minutes. Purification was performed using a filter with a 30000 molecular weight cut off manufactured by Millipore, followed by concentration. The protein concentration in the contents of each Eppendorf tube was measured, 5 μl of the contents of each Eppendorf tube were added to other Eppendorf tubes, and a 0.25 M ammonium acetate buffer solution (15 μl) and a 400 μM $^{57}$Co solution (10 μl) were added thereto. The reaction mixtures were incubated at 41° C. for 3 hours. 10 μl of a 0.01 M 1,4,7,10-tetraazacyclododecane-1,4,7,10-tetraacetic acid (DOTA) solution was added to each reaction mixture, and incubation was performed at 41° C. for 10 minutes. 1 μl of each reaction mixture was applied to a silica gel plate and developed with a developing solvent (MeOH:H$_2$O=1:1). The silica gel plates were cut in half lengthwise, and gamma rays were counted with a gamma ray counter using the plates. The results are shown in FIG. 1.

The aforementioned Compound 8 is a compound represented by Formula (II) wherein $R^1$ is a group represented by —CHO, and the aforementioned HSA is a compound containing an amino group. It was verified that, as shown in FIG. 1, Compound 8 promptly reacts with somatostatin and somatostatin can be labeled with Compound 8.

EXAMPLE 26

Molecular Labeling with a Compound Represented by Formula (II)

The labeling of green fluorescence protein (anti-GFP antibody) was investigated using Compound 8 produced in Example 3. See Scheme 36 below for the method for this labeling.

[Chemical Formula 283]

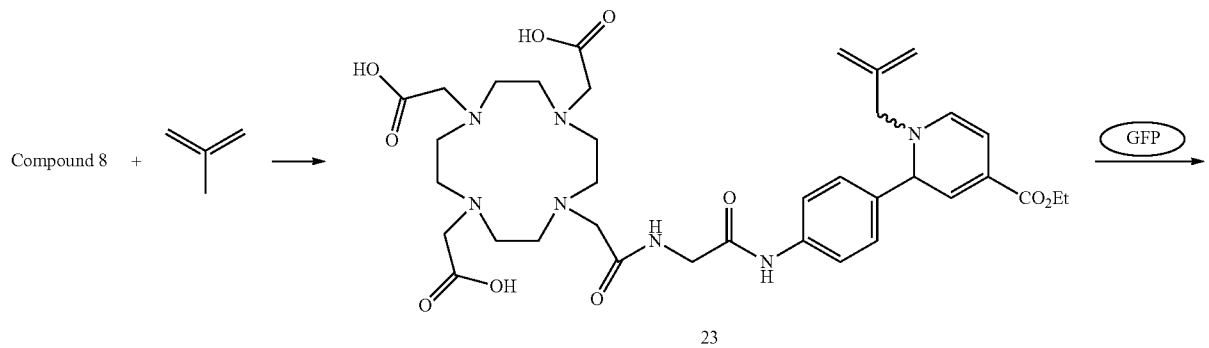

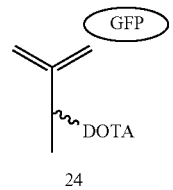

To a PBS buffer solution (81 µl) was added 27 µl of an anti-GFP antibody (20 µg/µl, PBS buffer solution, manufactured by Nacalai Tesque, Inc.) for dilution. The diluted anti-GFP solution was added to 4 Eppendorf tubes each in an amount of 3.3 µM, 8 µl, 2.6×10$^{-11}$ mol, and Compound 8 was added in a proportion of 10 equivalents (24 µM, 5 µl, 2.6×10$^{-10}$ mol), 50 equivalents (0.12 mM, 5 µl, 1.3×10$^{-9}$ mol), 250 equivalents (0.61 mM, 5 µl, 6.6×10$^{-9}$ mol) and 1250 equivalents (12 mM, 2.7 µl, 3.3×10$^{-8}$ mol) relative to the anti-GFP antibody. The mires were left to stand for 10 minutes at room temperature, and then a GFP antigen (cultured from *Escherichia coli*, PBS buffer solution, 1000 µl) was added and reacted at 4° C. for 1 hour. Thereafter, Protein G (500 µg, manufactured by GE Healthcare Ltd.) was added to the mixtures and left to stand at the same temperature for 30 minutes. Then, labeled anti-GFP (Compound 24) was purified by subjecting the mixtures to immune precipitation. GFP fluorescence measurement (excitation: 395 nm, emission: 509 nm) was performed on each anti-GFP. The results are shown in FIG. 2.

The aforementioned Compound 8 is a compound represented by Formula (II) wherein $R^1$ is a group represented by —CHO, and the aforementioned anti-GFP antibody is a compound containing an amino group. It was verified that, as shown in FIG. 2, Compound 8 promptly reacts with the anti-GFP antibody and the anti-GFP antibody can be labeled with Compound 8.

EXAMPLE 27

Measurement of the Biodistribution of a Compound Represented by Formula (II) in a Living Body It was investigated whether the distribution of AGCKNFF-WKTFTSC (somatostatin) can be measured using Compound 8 produced in Example 3. See Scheme 37 below for the measurement method.

Scheme 37

[Chemical Formula 284]

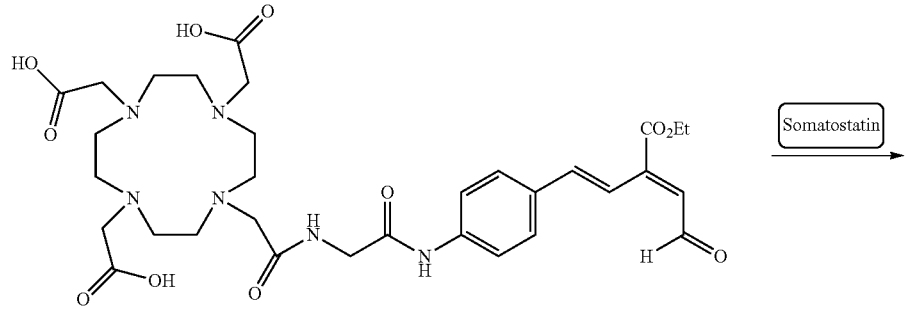

-continued

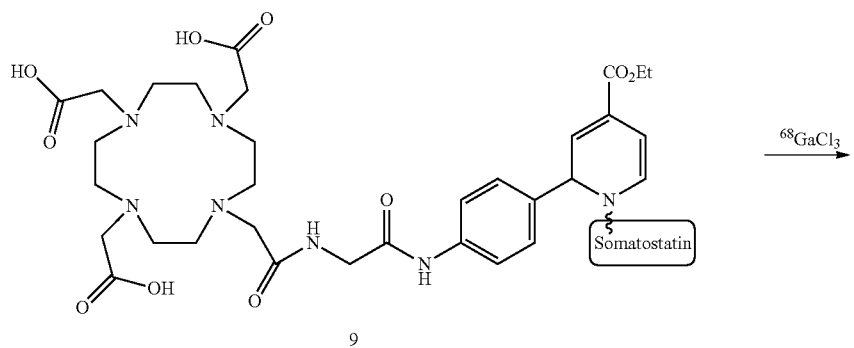

9

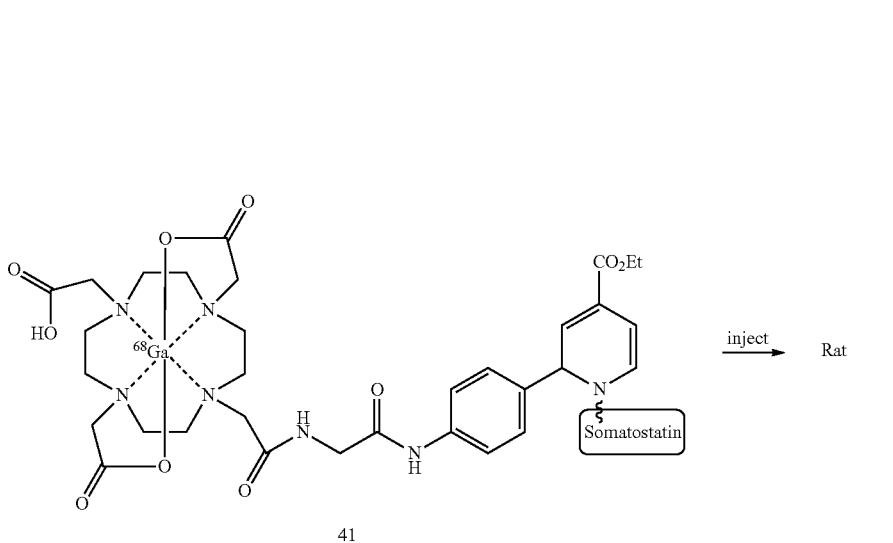

41

25.1 Production of DOTA-2-amino-6-(2-(4-(2-aminoacetamido)phenyl)-4-(ethoxycarbonyl)-ϵ-N-pyridin-1(2H-yl)-lysine-somatostatin (Compound 9)

A DMF solution (40 μl) of Compound 8 produced in Example 3 described above was added to a solution of somatostatin (0.17 mg, 0.10 μmol) in Otsuka distilled water (154 μl) and put into a vortex generator. The reaction mixture was left to stand at room temperature for 30 minutes and then lyophilized, thereby giving the titled Compound 9.
MALDI-TOF-MS m/z: 2307.4 [M]$^+$.

25.2 Production of $^{68}$Ga-DOTA-2-amino-6-(2-(4-(2-aminoacetamido)phenyl)-4-(ethoxycarbonyl)-ϵ-N-pyridin-1(2H-yl)-lysine-somatostatin (Compound 41)

A 1 N hydrochloric acid solution (400 μl) of $^{68}$GaCl$_3$ eluted from a $^{68}$Ga/$^{68}$Ge generator was purified, neutralized with aqueous 4 N NaOH and then added to Compound 9 described above. After incubation at 40° C. for 10 minutes, it was injected into a rat (Wistar rat 8W, male, 235 g) (1.68 mCi). Propofol was administered continuously at a rate of 40 g/kg into the tail vein of the rat for tranquilization, and a PET tracer was administered into the tail vein of the rat. A PET image of the rat is shown in FIG. 3. The picture of the PET imaging shows the amount accumulated from 3 minutes to 7 minutes after administration.

As shown in FIG. 3, it was verified that somatostatin was distributed across the heart of the rat.

EXAMPLE 28

Molecular Labeling with a Compound Represented by Formula (II)

The labeling of anti-GFP (green fluorescence protein) (anti-GFP antibody) was investigated using Compound 15 produced in Example 5. See Scheme 38 below for the measurement method.

Scheme 38

[Chemical Formula 285]

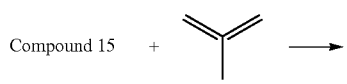

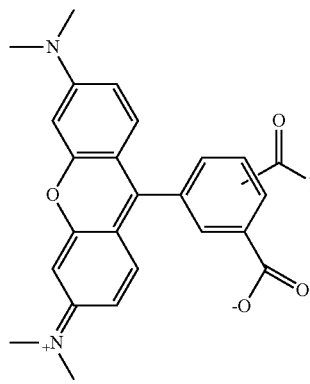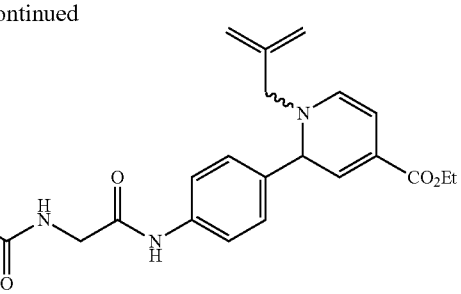

23

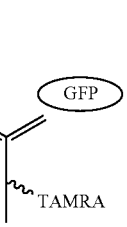

24

A PBS buffer solution (81 μl) was added to 27 μl of an anti-GFP antibody (20 μg/μl, PBS buffer solution, manufactured by Nacalai Tesque, Inc.) for dilution. The diluted anti-GFP solution thus obtained was added to 4 Eppendorf tubes each in an amount of 3.3 μM, 8 μl, $2.6 \times 10^{-11}$ mol, and Compound 15 described above was added in a proportion of 10 equivalents (24 μM, 5 μl, $2.6 \times 10^{-10}$ mol), 50 equivalents (0.12 mM, 5 μl, $1.3 \times 10^{-9}$ mol), 250 equivalents (0.61 mM, 5 μl, $6.6 \times 10^{-9}$ mol) and 1250 equivalents (12 mM, 2.7 μl, $3.3 \times 10^{-8}$ mol) relative to the anti-GFP antibody. The mixtures were left to stand for 30 minutes at room temperature, and then a GFP antigen (cultured from *Escherichia coli*, PBS buffer solution, 1000 μl) was added and reacted at 4° C. for 1 hour. Thereafter, Protein G (500 μg, manufactured by GE Healthcare Ltd.) was added to the mixtures and left to stand at the same temperature for 30 minutes. Then, anti-GFP-labeling TAMRA-GFP (Compound 22) was purified by subjecting the mixtures to immune precipitation. GFP fluorescence measurement was performed on Compound 22 (excitation: 395 nm, emission: 509 nm) as well as fluorescence measurement being performed on Compound 21 (excitation: 522 nm, emission: 574 nm). The results are shown in FIG. 4.

As shown in FIG. 4, the aforementioned Compound 15 is a compound represented by Formula (II) wherein $R^1$ is a group represented by —CHO, and the aforementioned anti-GFP antibody is a compound containing an amino group. It was verified that, as shown in FIG. 4, Compound 15 promptly reacts with the anti-GFP antibody and the anti-GFP antibody can be labeled with Compound 15.

EXAMPLE 29

Molecular Labeling with a Compound Represented by Formula (II)

The labeling of human serum albumin (HSA) was investigated using Compound 15 produced in Example 5. See Scheme 39 below for the measurement method.

[Chemical Formula 286]

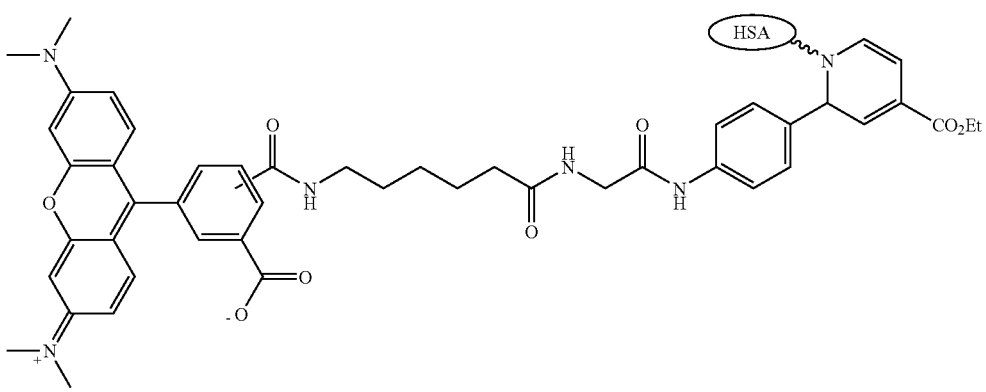

HSA (1.5 mg, 0.22 nmol) was dissolved in a PBS buffer solution (1000 μl). This solution was added to 6 Eppendorf tubes each in an amount of 0.22 μM, 8 μl, $1.8 \times 10^{-10}$ mol, and Compound 15 described above was added in a proportion of 10 equivalents (1.6 mM, 0.82 μl, $1.3 \times 10^{-9}$ mol), 20 equivalents (1.6 mM, 1.6 μl, $2.6 \times 10^{-9}$ mol), 50 equivalents (1.6 mM, 4.1 μl, $6.6 \times 10^{-9}$ mol), 100 equivalents (16 mM, 0.82 μl, $1.3 \times 10^{-8}$ mol), 250 equivalents (16 mM, 2.0 μl, $3.2 \times 10^{-8}$ mol) and 500 equivalents (16 mM, 4.0 μl, $6.4 \times 10^{-8}$ mol) relative to the HSA. The mixtures were left to stand for 30 minutes at room temperature and then subjected to gel filtration using a NAP column (manufactured by GE Healthcare Ltd.). Protein G (10 μl, manufactured by GE Healthcare Ltd.) and a PSB buffer solution were added and the mixtures were left to stand at 40° C. for 30 minutes. Then, the mixtures were subjected to immune precipitation, thereby purifying HSA-labeling TAMRA-2-amino-6-(2-(4-(2-aminoacetamido)phenyl)-4-(ethoxycarbonyl)-ε-N-pyridin-1(2-yl)-lysine -HSA (Compound 25). Fluorescence measurement (excitation: 522 nm, emission: 576 nm) was performed on each Compound 25. The results are shown in FIG. 5.

As shown in FIG. 5, the aforementioned Compound 15 is a compound represented by Formula (II) wherein $R^1$ is a group represented by —CHO, the aforementioned HSA is a compound containing an amino group. It was verified that, as shown in FIG. 5, Compound 15 promptly reacts with HSA and HSA can be labeled with Compound 15.

EXAMPLE 30

Molecular Labeling with a Compound Represented by Formula (II)

The labeling of ELYENKPRRPYIL (neurotensin) was investigated using Compound 39 produced in Example 11. See Scheme 40 below for the measurement method.

[Chemical Formula 287]

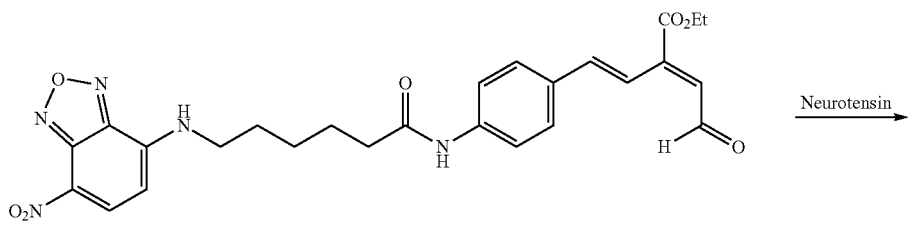

39

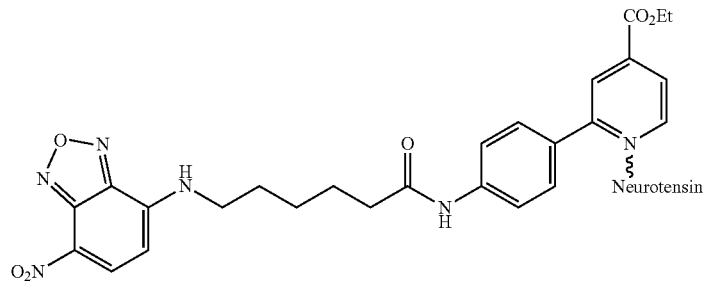

40

A dioxan solution (5 μl) of Compound 39 (100 μg, 0.19 μmol) was added to an aqueous solution (100 μl) of neurotensin (0.32 mg, 0.2 nmol), and the mixture was left to stand at room temperature for 2 hours, thereby giving Compound 40.

ESI-MS m/z: 1098 $[M+NH_4^+ +H]^{2+}$

EXAMPLE 31

Molecular Labeling with a Compound Represented by Formula (III)

The labeling of human serum albumin (HSA) was investigated using Compound 50 produced in Example 14. See Scheme 41 below for the measurement method.

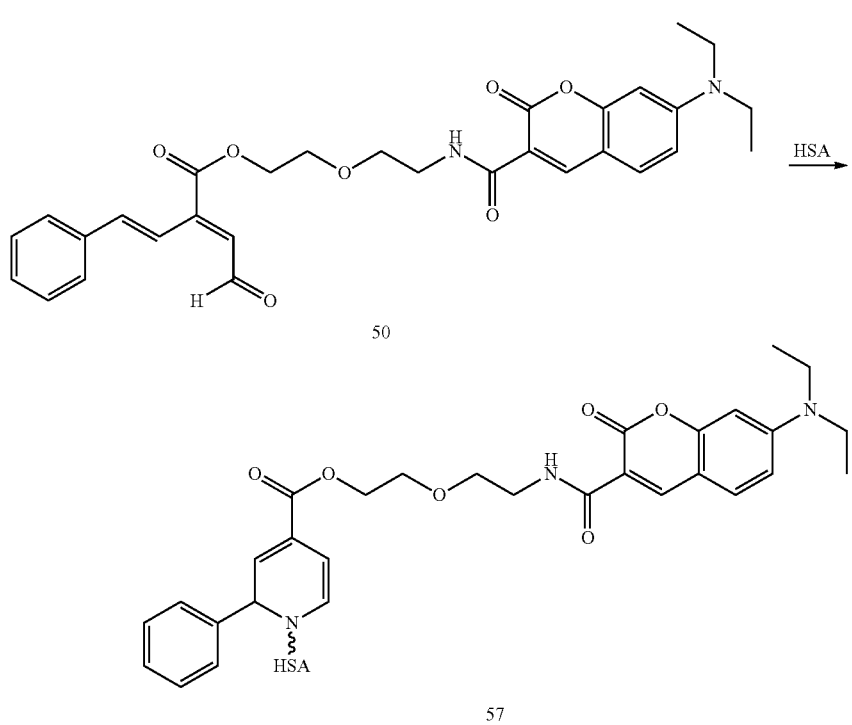

[Chemical Formula 288]

HSA was dissolved in a phosphate buffer (0.1 M, pH 7.4) to adjust the concentration to $5.0 \times 10^{-5}$ M. 20 μl of a phosphate buffer (0.1 M, pH 7.4) was added to 200 μl of the solution for dilution, and the mixture was pre-incubated at 40° C. for 5 minutes. A 1,4-dioxane (20 μl) solution of Compound 50 (50 μg, 0.1 μmol) was added to the mixture, and the mixture was incubated at 40° C. for 1 hour. 300 μl of 1% acetic acid was added to the reaction solution to quench the reaction, and the reaction solution was purified by gel filtration and lyophilized.

When the reaction product of the aforementioned Compound 50 and HSA was irradiated with 420 nm excitation light for the measurement of a fluorescence spectrum, intense fluorescence was observed near 460 nm, which is a fluorescence characteristic of coumarin. Accordingly, the formation of Compound 57 was confirmed.

EXAMPLE 32

Molecular Labeling with a Compound Represented by Formula (IV)

The labeling of human serum albumin (HSA) was investigated using Compound 56 produced in Example 21. See Scheme 42 below for the measurement method.

Scheme 42

[Chemical Formula 289]

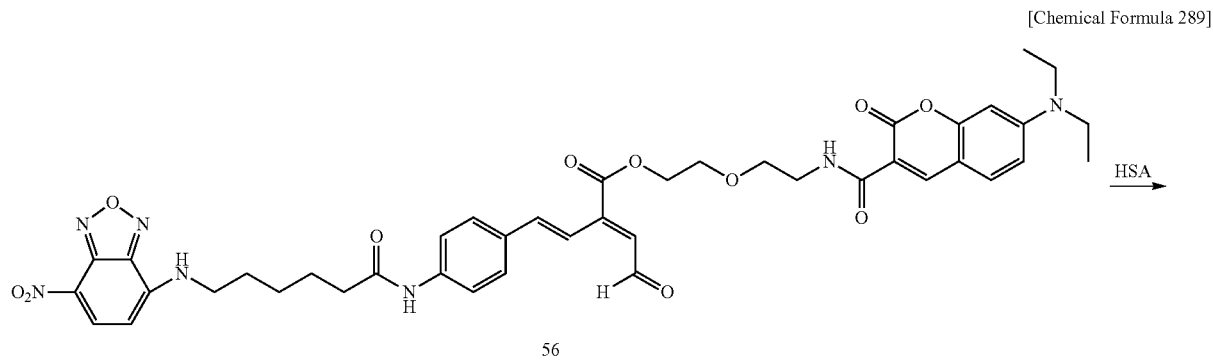

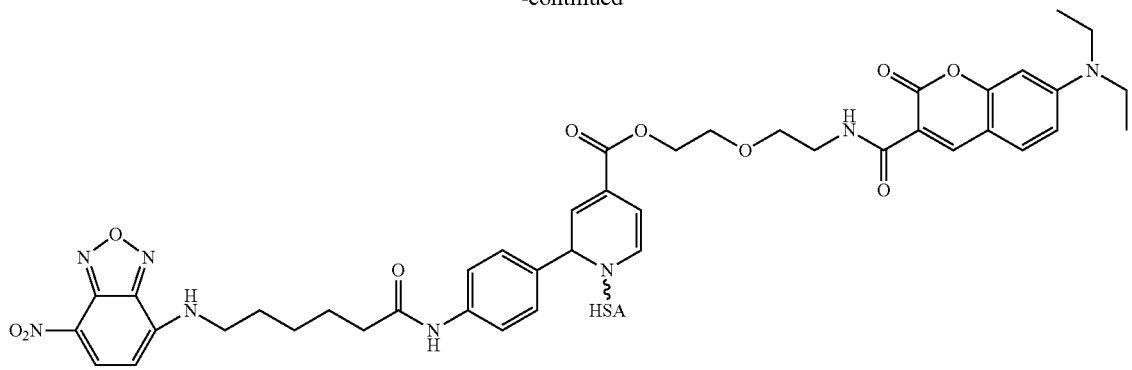

58

HSA was dissolved in a phosphate buffer solution (0.1 M, pH 7.4) to adjust the concentration to 5.0×10$^{-5}$ M. 20 μl of a phosphate buffer solution (0.1 M, pH 7.4) was added to 200 μl of the solution for dilution, and the mixture was pre-incubated at 40° C. for 5 minutes. A 1,4-dioxane (20 μl) solution of Compound 56 (50 μg, 0.1 μmol) was added to the mixture, and the mixture was incubated at 40° C. for 1 hour. 300 μl of 1% acetic acid was added to the reaction solution to quench the reaction, and the reaction solution was purified by gel filtration and lyophilized.

When the reaction product of the aforementioned Compound 56 and HSA was irradiated with 420 nm excitation light for the measurement of a fluorescence spectrum, intense fluorescence was observed near 460 nm, which is a fluorescence characteristic of coumarin. Accordingly, the formation of Compound 58 was confirmed.

INDUSTRIAL APPLICABILITY

The hexatriene-β-carbonyl compound of the present invention is useful for, for example, PET.

Figure 1:
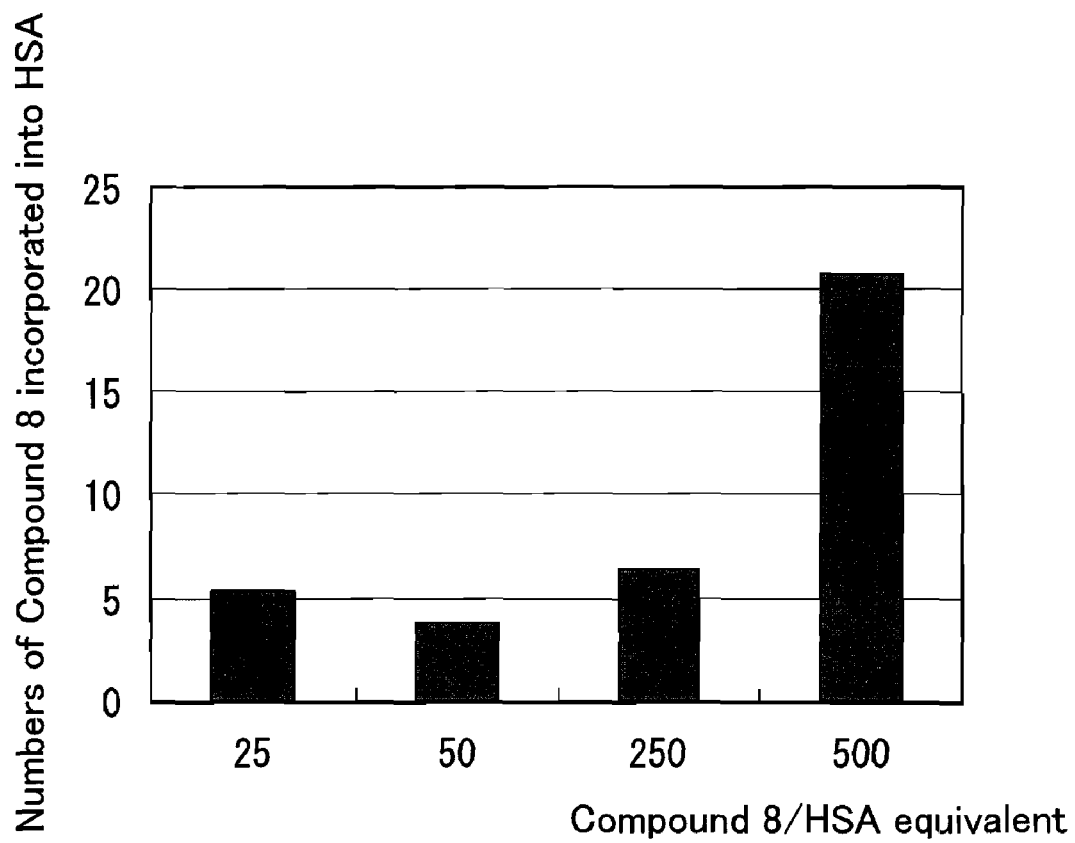
FIG. 1 is a bar chart showing incorporation into HSA in Example 25.
Figure 2:
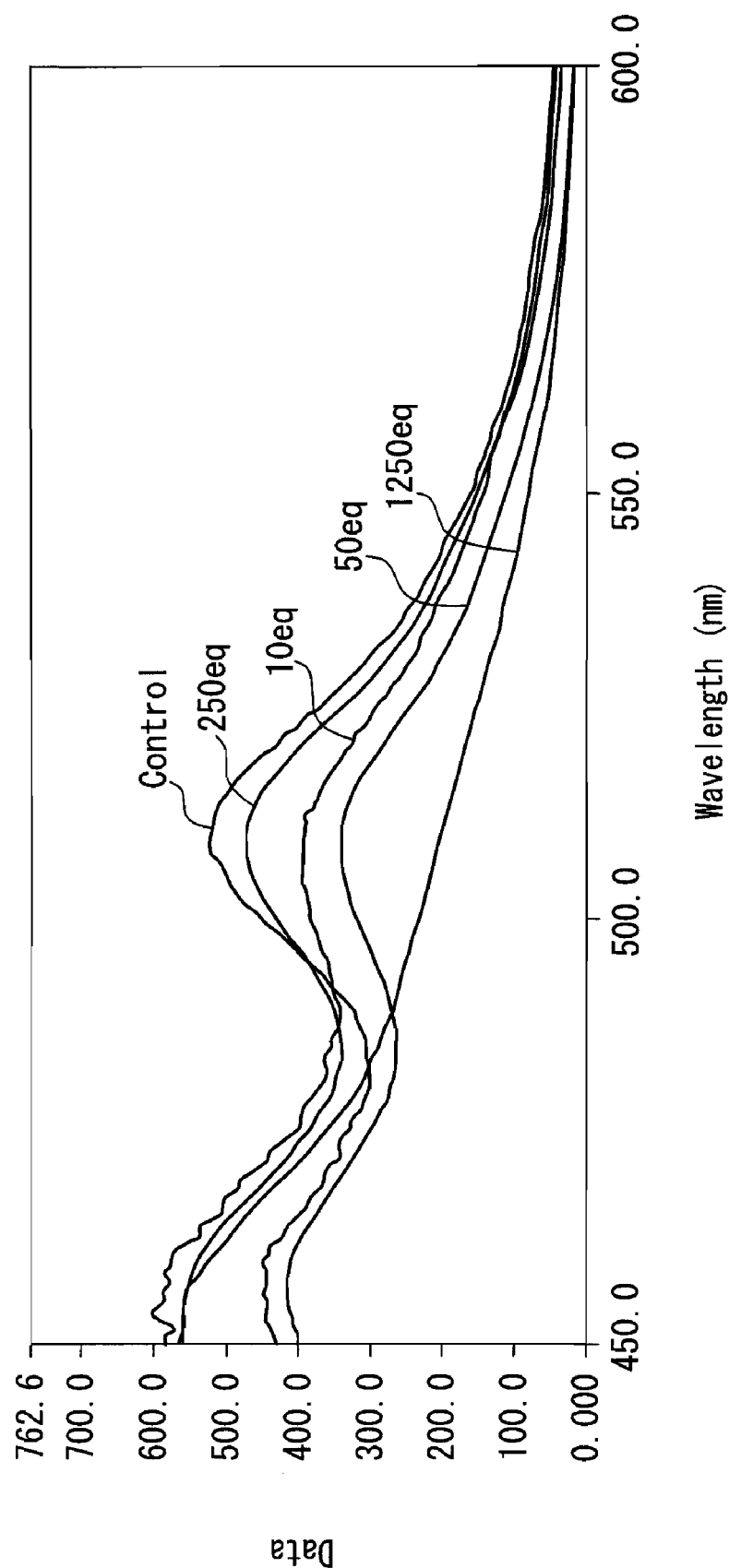
FIG. 2 is a graph showing incorporation into an antibody in Example 26.
Figure 3:
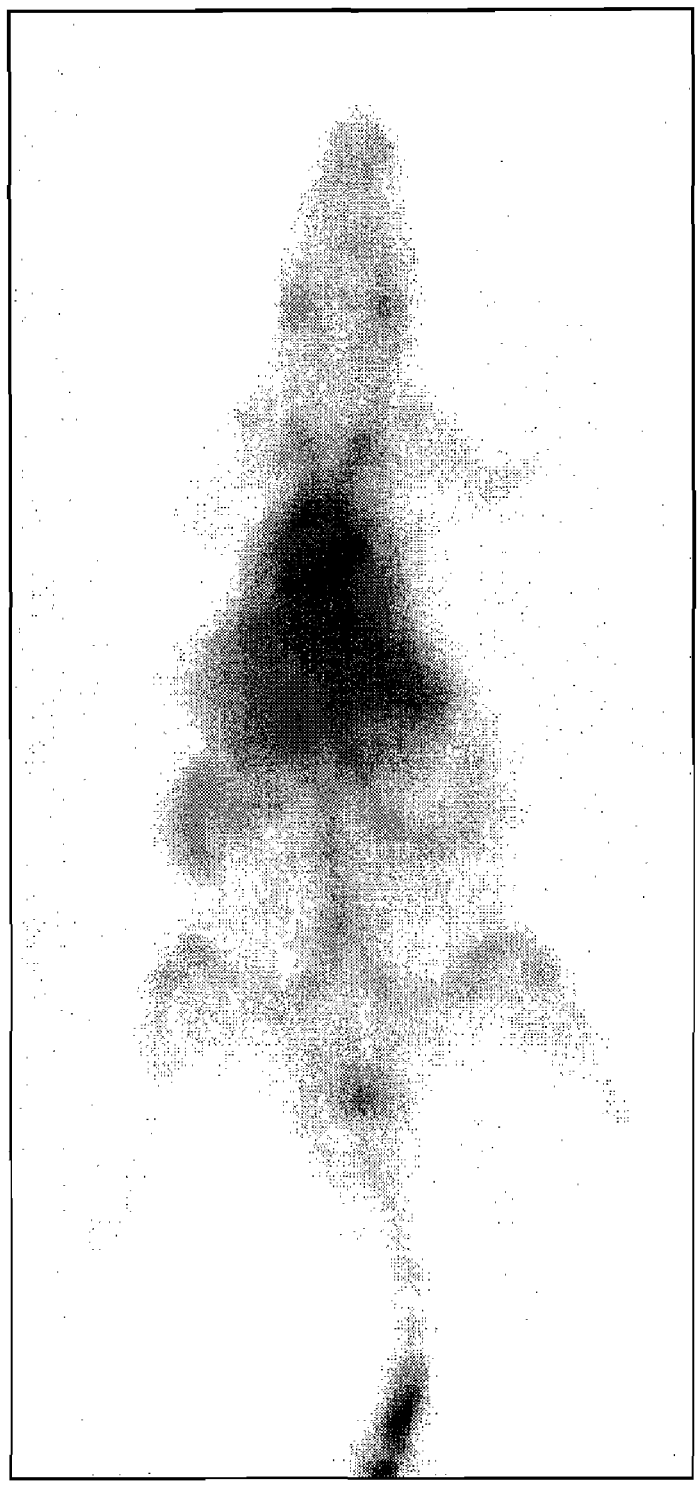
FIG. 3 is a PET image in Example 27.
Figure 4:
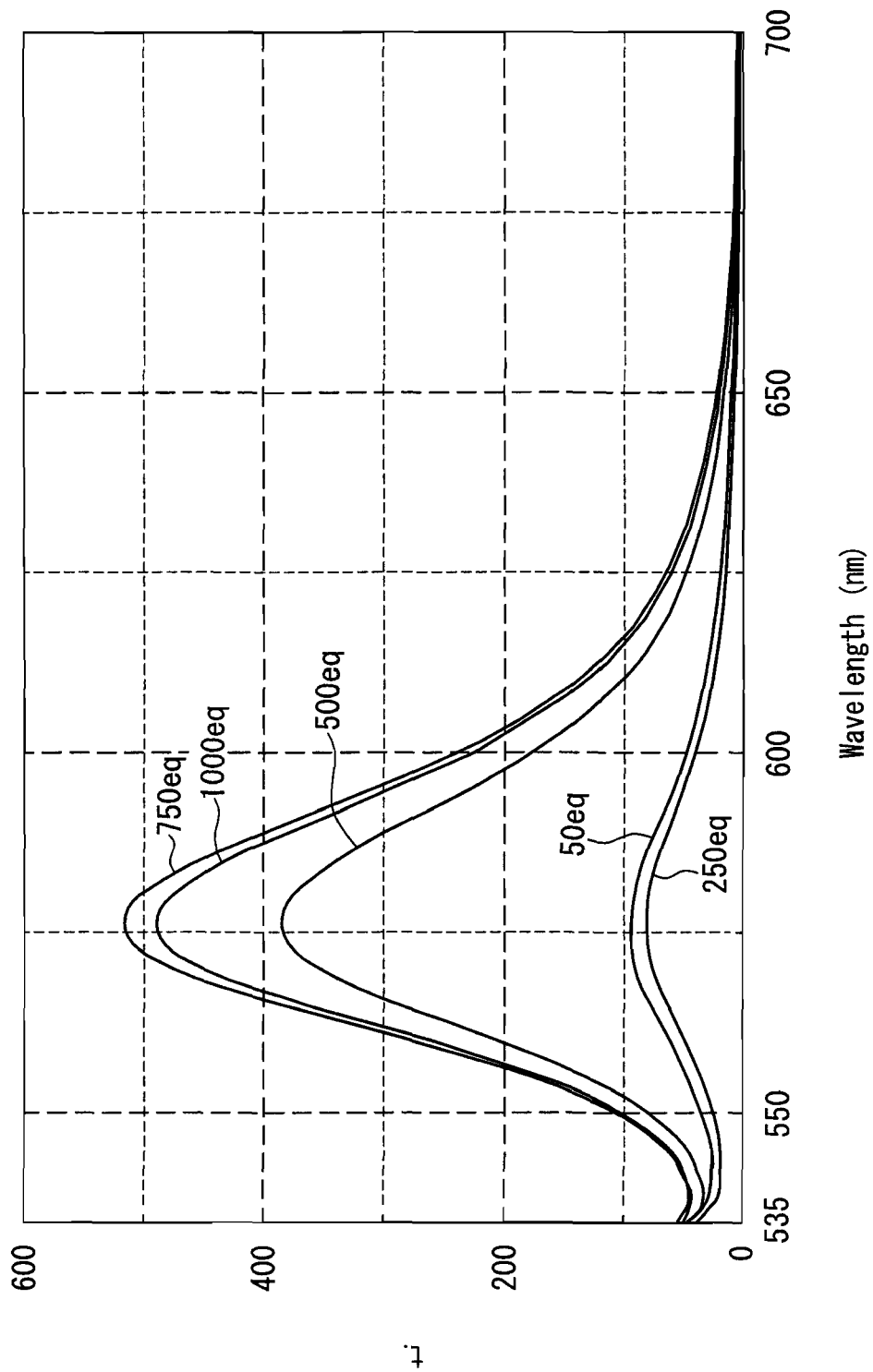
FIG. 4 is a graph showing incorporation into an antibody in Example 28.
Figure 5:
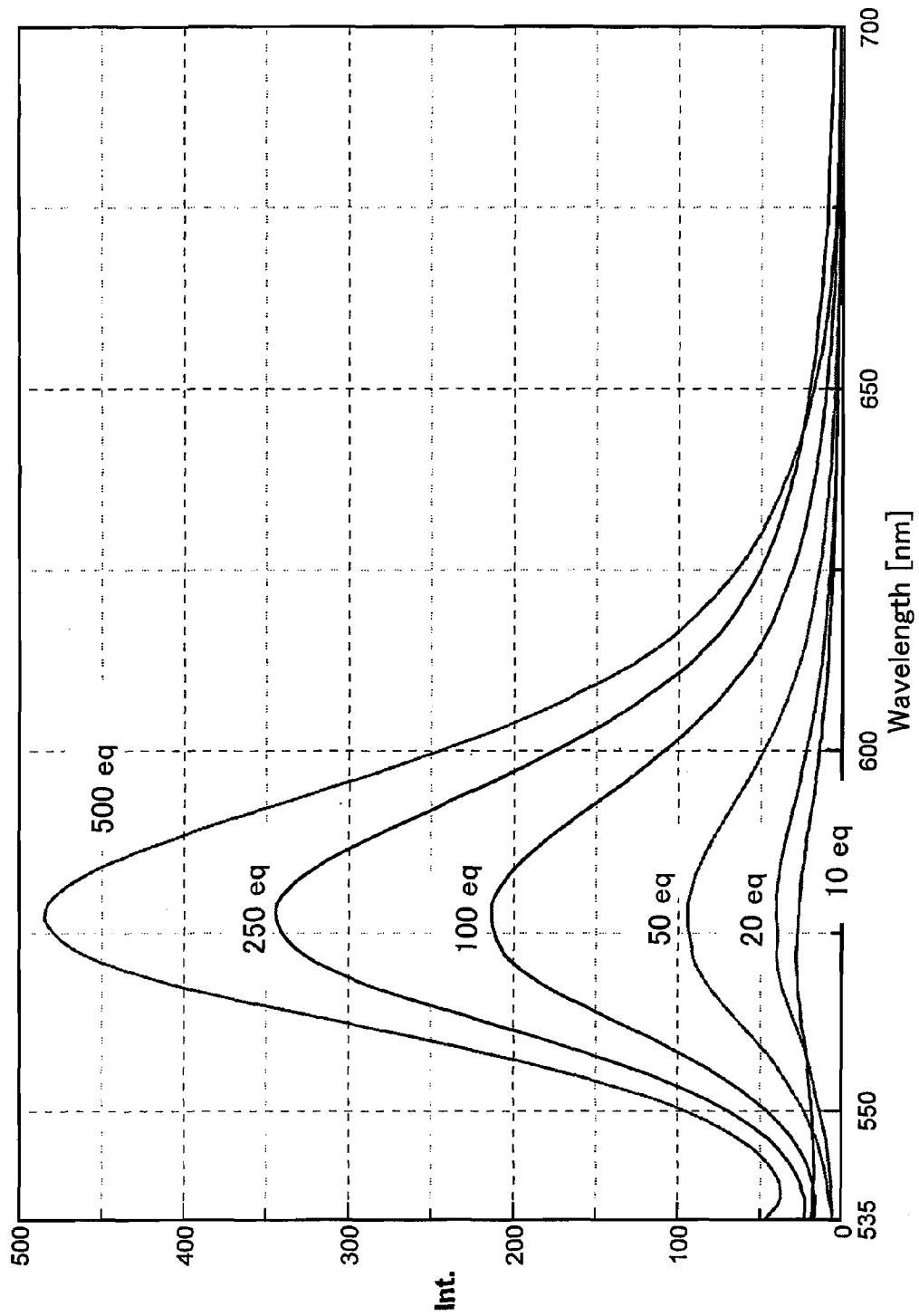
FIG. 5 is a graph showing incorporation into an antibody in Example 29.

The invention claimed is:
1. A compound represented by formula (I):

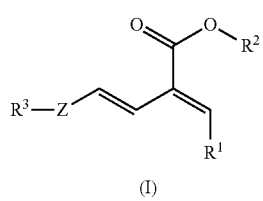

(I)

wherein,
R$^1$ is a group represented by —CH$_2$OH or —CH$_2$—OR$^{11}$,
R$^2$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by a formula: -L$^2$-A$^2$-M$^2$,
R$^3$ is a hydrogen atom, a lower alkyl group, a lower alkyl group substituted with one or more substituents, an ar(lower)alkyl group, an ar(lower)alkyl group substituted with one or more substituents, an aryl group, an aryl group substituted with one or more substituents, a heteroaryl group, a heteroaryl group substituted with one or more substituents, or a group represented by a formula: -L$^1$-A$^1$-M$^1$, a formula: -L$^1$-N$_3$, or a formula:

-L$^1$-C≡CH, wherein, when R$^2$ is the hydrogen atom, the lower alkyl group, the lower alkyl group substituted with one or more substituents, the ar(lower)alkyl group, the ar(lower)alkyl group substituted with one or more substituents, the aryl group, the aryl group substituted with one or more substituents, the heteroaryl group, or the heteroaryl group substituted with one or more substituents, R$^3$ is the group represented by the formula: -L$^1$-A$^1$-M$^1$, the formula: -L$^1$-N$_3$, or the formula -L$^1$-C≡CH, and
when R$^2$ is a group represented by the formula -L$^2$-A$^2$-M$^2$, R$^3$ is the hydrogen atom, the lower alkyl group, the lower alkyl group substituted with one or more substituents, the ar(lower)alkyl group, the ar(lower)alkyl group substituted with one or more substituents, the aryl group, the aryl group substituted with one or more substituents, the heteroaryl group, or the heteroaryl group substituted with one or more substituents, and
Z is
a divalent group derived from an aromatic hydrocarbon; and
in the formulae above,
L$^1$ is a group represented by a formula: —(CH$_2$)$_n$—, a formula: —(CH$_2$)$_n$—O—(CH$_2$)$_m$—, a formula: —(CH$_2$)$_n$—CONH—, or a formula: —CONH—(CH$_2$)$_n$—,
wherein n and m each independently represent an integer of 1 to 20,
A$^1$ is a group represented by —NH—,
L$^2$ is a bond or a group represented by —(CH$_2$)$_n$—O—(CH$_2$)$_m$— wherein n and m each independently represent an integer of 1 to 20, $A^2$ is a group represented by —O—, —$CO_2$—, —S—, or —NH—, $M^1$ is a hydrogen atom, $M^2$ is a hydrogen atom or a protecting group for a group represented by —OH, —$CO_2H$, —SH or —$NH_2$, $R^{11}$ is a protecting group for a hydroxyl group, $R^{12}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents, and $R^{13}$ is a hydrogen atom, a lower alkyl group, a lower alkyl group substituted with one or more substituents, a lower alkoxy group, a lower alkoxy group substituted with one or more substituents, an ar(lower)alkyl group, an ar(lower)alkyl group substituted with one or more substituents, an ar(lower)alkoxy group, an ar(lower)alkoxy group substituted with one or more substituents, an aryl group, an aryl group substituted with one or more substituents, a heteroaryl group or a heteroaryl group substituted with one or more substituents.

2. The compound according to claim 1, wherein in the formula (I), $R^1$ refers to a group represented by —$CH_2OH$ or —$CH_2$—$OSi(t-Bu)Ph_2$, $R^2$ refers to a lower alkyl group or a group represented by a formula: -$L^2$-$A^2$-M, $R^3$ refers to a hydrogen atom or a group represented by a formula: -$L^1$-$A^1$-$M^1$, a group represented by the formula -$L^1$-$N_3$, or a group represented by the formula: -$L^1$-C≡CH, wherein, when $R^2$ is the lower alkyl group, $R^3$ is the group represented by the formula: -$L^1$-$A^1$-$M^1$, the formula: -$L^1$-$N_3$, or the formula -$L^1$-C≡CH, and when $R^2$ is a group represented by the formula -$L^2$-$A^2$-M, $R^3$ is the hydrogen atom, and Z refers to a divalent group derived from an aromatic hydrocarbon; and, in the formulae above, $L^1$ is a group represented by —$(CH_2)_n$—CONH— or —CONH—$(CH_2)_n$—, wherein n represents an integer of 1 to 20, $A^1$ is a group represented by —NH—, $L^2$ is a bond or a group represented by —$(CH_2)_n$—O—$(CH_2)_m$—, wherein n and m each independently represent an integer of 1 to 20, $A^2$ is a group represented by —O—, —$CO_2$—, —S—, or —NH—, M refers to a hydrogen atom or an acyl group, and $M^1$ is a hydrogen atom.

\* \* \* \* \*